(12) United States Patent
Tubert et al.

(10) Patent No.: US 8,999,948 B2
(45) Date of Patent: Apr. 7, 2015

(54) VECTORS AND SEQUENCES FOR THE TREATMENT OF DISEASES

(75) Inventors: Fátima Bosch Tubert, Cerdanyola del Valles (ES); Éduard Ayuso López, Olesa de Montserrat (ES); Albert Ruzo Matías, Barcelona (ES)

(73) Assignees: Laboratorios del Dr. Esteve, S.A., Barcelona (ES); Universidad Autonoma de Barcelona, Barcelona (ES)

( * ) Notice: Subject to any disclaimer, the term of this patent is extended or adjusted under 35 U.S.C. 154(b) by 0 days.

(21) Appl. No.: 13/703,179

(22) PCT Filed: Jun. 10, 2011

(86) PCT No.: PCT/EP2011/059678
§ 371 (c)(1),
(2), (4) Date: Feb. 20, 2013

(87) PCT Pub. No.: WO2011/154520
PCT Pub. Date: Dec. 15, 2011

(65) Prior Publication Data
US 2013/0158104 A1  Jun. 20, 2013

(30) Foreign Application Priority Data

Jun. 10, 2010 (EP) .................................... 10382169

(51) Int. Cl.
*C12N 15/52* (2006.01)
*A61K 48/00* (2006.01)
*C12N 9/14* (2006.01)
*C12N 15/86* (2006.01)
*C12N 15/864* (2006.01)

(52) U.S. Cl.
CPC .............. *A61K 48/0066* (2013.01); *C12N 9/14* (2013.01); *C12N 15/86* (2013.01); *C12N 2750/14143* (2013.01); *C12N 2830/008* (2013.01); *C12N 2830/48* (2013.01); *C12N 2840/105* (2013.01); *C12N 15/52* (2013.01); *C12N 15/8645* (2013.01)

(58) Field of Classification Search
CPC . A61K 48/00; A61K 48/0066; C12Y 310/00; C12N 2840/105
See application file for complete search history.

(56) References Cited

U.S. PATENT DOCUMENTS 8,227,212 B2 * 7/2012 von Figura et al. .......... 435/70.1

FOREIGN PATENT DOCUMENTS

WO    WO 2008/124724    10/2008

OTHER PUBLICATIONS

Brio et al., The BlastNP: A novel, sensitive Sequence Similarity Searching Method using Overlappingly Translated Sequences. Proceedings of the 26th Annual International Conference of the IEEE EMBS, San Francisco, CA, USA o Sep. 1-5, 2004. p. 2777-2780.*

Entelechon Corp. Nov 1, 2008. Codon Optimization Tool, http:www.entelechon.com/2008/10/backtranslation-tool/.*

Waldman et al., Translation efficiency in humans: tissue specificity, global optimization and differences between developmental stages. Nucleic Acids Research, 2010, vol. 38, No. 9 p. 2964-2974.*

Royo et al., Specific AAV Serotypes Stably Transduce Primary Hippocampal and Cortical Cultures with High Efficiency and Low Toxicity. Brain Res. Jan. 23, 2008; 1190: 15-22.*

Fraldi Alessandro et al: "Functional correction of CNS lesions in an MPS-IIIA mouse model by intracerebral AAV-mediated delivery of sulfamidase and SUMF1 genes.", Human Molecular Genetics, vol. 16, No. 22, Nov. 15, 2007, pp. 2693-2702, XP002601850, ISSN: 0964-6906.

Foster Helen et al: "Codon and mRNA sequence optimization of microdystrophin transgenes improves expression and physiological outcome in dystrophic mdx mice following AAV2/8 gene transfer.", Molecular Therapy : The Journal of the American Society of Gene Therapy, vol. 16, No. 11, Nov. 2008, pp. 1825-1832, XP002601851, ISSN: 1525-0024, abstract, p. 1826-1827, p. 1829, figure 2.

Shi Shuiliang et al: "Production of recombinant AAV vectors encoding insulin-like growth factor I is enhanced by interaction among AAV rep regulatory sequences.", Virology Journal, vol. 6, No, 3. 2009, pp. 1-11, XP002622828, ISSN: 1743-422X, abstract.

Michelfelder Stefan et al: "Adeno-associated viral vectors and their redirection to cell-type specific receptors", Advances in Genetics, Academic Press, XX, vol. 67, Jan. 1, 2009, pp. 29-60, XP009137628, ISSN: 0065-2660, paragraph [0005], paragraph [0006].

Ponder Katherine P: "Gene therapy for hemophilia.", Current Opinion in Hematology Sep. 2006 LNKD-PUBMED:16888433, vol. 13, No. 5, Sep. 2006, pp. 301-307, XP002650093, ISSN: 1065-6251, table 2.

Davidoff et al: "Comparison of the ability of adeno-associated viral vectors pseudotyped with serotype 2, 5, and 8, capsid proteins to mediate efficient transduction of the liver in murine and nonhuman primate models", Molecular Therapy, Academic Press, San Diego, CA, US, vol. 11, No. 6, Jun. 1, 2005, pp. 875-888, XP005002707, ISSN: 1525-0016, DOI: 0.1016/J,YMTHE.2004.12.022, p. 887.

Donsante et al: "237. Evaluation of Low-Level, Constitutive Expression of beta-glucuronidase on the Clinical Manifestations of Mucopolysaccharidosis Type VII", Molecular Therapy, Academic Press, San Diego, CA, US, vol. 11, Aug. 15, 2005, pp. 93-94, XP005015576, ISSN: 1525-0016, abstarct.

Valstar MJ et al: "Sanfilippo syndrome: A mini-review", Journal of Inherited Metabolic Disease, vol. 31, No. 2, Apr. 4, 2008, pp. 240-252, XP019600529, Kluwer Academic Publishers, DO ISSN: 1573-2665, the whole document.

Meikle P, et al., JAMA 1999; 281: 249-254.

Neufeld E, Muenzer J, "The mucopolysaccharidoses" in Scriver C, et al., Eds., "The metabolic and molecular basis of inherited disease" (McGraw-Hill Publishing Co., New York, N.Y., US, 2001, pp. 3421-3452).

(Continued)

*Primary Examiner* — Scott Long
*Assistant Examiner* — Arthur S Leonard
(74) *Attorney, Agent, or Firm* — Leason Ellis LLP

(57) ABSTRACT

The present invention provides new sequences, gene constructions, vectors and pharmaceutical compositions for the treatment of diseases and specially, for the treatment of mucopolysaccharidoses.

21 Claims, 17 Drawing Sheets

(56) References Cited

OTHER PUBLICATIONS

Sivakumur P, Wraith J, J. Inherit. Metab. Dis. 1999; 22:849-850.
Harmatz P, et al., J. Mol. Genet. Metab. 2008; 94:469-475.
Muenzer J, et al., Genet. Med. 2006; 8:465-473.
Wraith J, et al., J. Pediatr. 2004; 144:581-588.
Enns G, Huhn S, Neurosurg. Focus 2008; 24:El2.
Vogler C, et al., Proc. Natl. Acad. Sci. USA 2005; 102: 14777-14782.
Hemsley K, et al., Genes BrainBehav. 2008; 7: 740-753.
Savas P, et al., Mol. Genet. Metab. 2004; 82:273-285.
Daya S, Berns K, Clin. Microbiol. Rev. 2008; 21:583-593.
McIntyre C, et al., Mol. Genet. Metab. 2008; 93:411-418.
"SGSH N-sulfoglucosamine Sulfohydrolase [*Homo sapiens* (human)]." NCBI. N.p., Aug. 26, 2013. Web.

\* cited by examiner

VECTORS AND SEQUENCES FOR THE TREATMENT OF DISEASES

FIELD OF THE INVENTION

The present invention relates to vectors useful for the expression of proteins of interest and their utilization in gene therapy. The present invention also relates to vectors and nucleic acid sequences helpful for the treatment of mucopolysaccharidoses (MPS), and in particular, for the treatment of mucopolysaccharidoses type III or Sanfilippo syndrome.

BACKGROUND OF THE INVENTION

The lysosome is an organelle founded in the cytoplasm of eukaryotic cells, which serves as storage for many hydrolytic enzymes and as a center for degrading and recycling cellular components. This organelle contains several types of hydrolytic enzymes, including proteases, nucleases, glycosidases, lipases, phospholipases, phosphatases and sulfatases. All enzymes are acid hydrolases.

Lysosomal storage diseases (LSDs) are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis.

LSDs are individually rare, although as a group these disorders are relatively common in the general population. The combined prevalence of LSDs is approximately 1 per 5,000 live births. See Meikle P, et al., JAMA 1999; 281:249-254. However, some groups within the general population are particularly afflicted by a high occurrence of LSDs. For instance, the prevalence rates of the Gaucher and Tay-Sachs diseases in descendants from Jewish Central and Eastern European (Ashkenazi) individuals is 1 per 600 and 1 per 3,900 births, respectively. The Finnish population is also afflicted by an uncommonly high LSDs prevalence rate.

Type III mucopolysaccharidoses (MPSIII), known collectively as Sanfilippo syndrome, are LSDs caused by a deficiency in one of the enzymes involved in the degradation of heparan sulfate, leading to its pathological accumulation. MPSIII is classified into four subtypes depending on the enzyme deficiency. Loss of sulfamidase activity causes subtype IIIA and has been reported to be the most severe, with the earliest disease onset and shortest survival. Symptoms of MPSIIIA occur in the first years of life, and are characterized by severe neurodegeneration that leads to deep mental retardation, aggressiveness, hyperactivity, and sleep alterations. Patients progressively lose the capacity of speech, swallow, and basic motor coordination. In addition to the neurological symptoms, MPSIIIA patients suffer non-neurological alterations, including hepato- and splenomegaly, skeletal and joint malformations, as well as frequent diarrhoea and respiratory tract infections. The progressive worsening of symptoms results in the death of the patient during adolescence. See Neufeld E, Muenzer J, "The mucopolysaccharidoses" in Scriver C, et al., Eds., "The metabolic and molecular basis of inherited disease" (McGraw-Hill Publishing Co., New York, N.Y., US, 2001, pp. 3421-3452).

There is no cure for MPSIIIA currently and, therefore, existing treatments are aimed at controlling symptoms of the disease in order to improve the poor quality of life of the patients. MPS disorders can be treated by bone marrow transplantation or enzyme replacement therapy (ERT). Both approaches rely in the endocytosis of lysosomal enzymes from extracellular medium and their targeting to lysosomes via the mannose-6-phosphate receptor (M6PR) present at the cell membrane. Nevertheless, bone marrow transplantation has demonstrated to be inefficient in the treatment of MPSIII patients. See Sivakamur P, Wraith J, J. Inherit. Metab. Dis. 1999; 22:849-850. ERT has been extensively proven to be effective in counteracting the non-neurological accumulation in other lysosomal storage diseases, including MPSI, II and VI. See Harmatz P, et al., J. Mol. Genet. Metab. 2008; 94:469-475; Muenzer J, et al., Genet. Med. 2006; 8:465-473 and Wraith J, et al., J. Pediatr. 2004; 144:581-588. In addition to the high cost of these treatments, it has been shown that ERT does not result in correction or preservation of neuronal function due to the insufficient delivery of the exogenously provided enzyme through the blood-brain barrier (BBB). See Enns G, Huhn S, Neurosurg. Focus 2008; 24:E12. More recently, it has been demonstrated that high-dose ERT is partially successful in clearing CNS storage in MPS VII, possibly due to the saturation of M6PR and mannose receptors that lead to a longer half-life of the protein in circulation. See Vogler C, et al., Proc. Natl. Acad. Sci. USA 2005; 102: 14777-14782. This study demonstrates that high levels of the enzyme in circulation during long periods of time correlate with a better correction of the pathology. Intracerebral and intra-CSF delivery of the enzyme have also been proved to be efficient in reducing CNS pathology in MPS IIIA mice. See Hemsley K, et al., Genes Brain Behav. 2008; 53(2):161-8 and Saves P, et al., Mol. Genet. Metab. 2004; 82:273-285. However, this approach is highly invasive due to the need for multiple repeated injections and could increase the risk of damage and/or infections in the brain.

Given the limitations of current therapeutic options for MPSIII, alternative approaches are needed. Gene transfer could provide the means to achieve a permanent production of the missing enzyme from a single intervention. Adeno-associated vectors (AAV) are rapidly emerging as the vector of choice for many gene therapy applications, due to their high transduction efficiency and their lack of pathogenicity. AAV vectors efficiently transduce post-mitotic cells and several pre-clinical and clinical studies demonstrated the potential of AAV vector-mediated gene transfer to efficiently drive sustained expression of therapeutic transgenes for a variety of diseases. See Daya S, Berns K, Clin. Microbiol. Rev. 2008; 21:583-593.

It has been shown that the administration of an AAV5 vector co-expressing sulfamidase and the sulfatase activator SUMF1 in lateral ventricles of newborn MPSIIIA mice is able to correct many neurological and behavioral alterations. See Fraldi A, et al., Hum. Mol. Genet. 2007; 16:2693-2702. However, this proposed course of action has several shortcomings. First, the CMV promoter utilized has been reported to silence. Second, the long term effects of the co-expression of sulfamidase and SUMF1 have not been assessed yet. It is not clear if the co-expression of SUMF is even necessary and provides any additional permanent benefits in comparison to the treatment with sulfamidase only. Third, AAV5 vectors have a low distribution within the parenchyma, and more importantly, the delivery of sulfamidase into the brain by using these vectors does not result in any transduction of the cerebral tissue, thus, no correction of somatic phenotype is achieved by following this approach. Finally, Fraldi, 2007, supra demonstrated the efficacy of gene transfer in only newborn MPSIIIA mice. No experiments were reported in older mice. Since MPSIIIA is usually diagnosed after 3-4 years of age, the newborn animal model is not adequate for predicting the effects of this treatment in human beings.

In view of the difficulties for diagnosing MPSIIIA at birth, the development of therapeutic interventions starting in early adulthood has been proposed. It has been reported that the intravenous delivery of a lentiviral vector expressing sulfamidase in adult mice resulted in little amelioration of the CNS phenotype, likely due to the relatively poor transduction performance of these vectors in vivo. See McIntyre C, et al., Mol. Genet. Metab. 2008; 93:411-418. Thus, the use of viral vectors with higher transduction efficacy in vivo, such as AAV vectors, may provide higher circulating levels of sulfamidase, which could potentially ameliorate or correct the neurological pathology.

The treatment of MPSIIIA via gene therapy requires more efficient vectors and sulfamidase coding sequences. Therefore, there is a long-felt need for an effective treatment of MPSIIIA. There is also the need for novel approaches to the treatment of this disease that would have enhanced security features. MPSIIIA is a rare disease and is therefore an orphan disease. The pharmaceutical agents developed specifically to treat this rare medical condition will be orphan drugs.

SUMMARY OF THE INVENTION

The present invention provides a new nucleotide sequence for the treatment of diseases, preferably for the treatment of mucopolysaccharidoses (MPS). Therefore, the first aspect of the invention refers to a nucleotide sequence that is a codon optimized sequence of human sulfamidase that allows the transcription of a more stable mRNA. This sequence is transcribed at higher rates, and therefore, produces higher yields of the sulfamidase enzyme. The sequence has a better expression profile and is more effective therapeutically than other attempts to codon optimize the sulfamidase nucleotide sequence. These increased levels in the enzyme expression are followed by an increase in the serum sulfamidase activity, allowing the reduction of the glyocosaminoglycan (GAG) accumulation that causes the disease. Said sequence is SEQ ID NO: 1 or a sequence having at least 85% sequence identity to SEQ ID NO: 1 that codifies for the protein SEQ ID NO: 2.

In a second aspect, the invention relates to a gene construction comprising the nucleotide sequence of the first aspect of the invention.

The present invention also provides new AAV vectors with serotype 9 that are capable of passing across the blood-brain barrier (BBB) and show more tropism for different brain structures. This allows the sulfamidase activity to be increased specifically in the brain, reducing the GAG accumulation and therefore improving the neurological symptoms of MPS. The AAV serotype 9 shows also an unexpectedly high tropism for heart, pancreas and muscle tissue, thus potentiating the overall therapeutic benefits of the invention.

For example, after administrating AAV serotypes 8 and 9 (AAV8 and AAV9) vectors to adult MPSIIIA mice by intravenous (iv) injection, to target the liver, or by intramuscular (im) injection, to target the skeletal muscle, or intracisternally (ic), to target the central nervous system, the levels of sulfamidase expression achieved with im-vector delivery were not therapeutic. The intracisternal administration was able, not only to increase the level of circulating sulfamidase, but also, to revert the somatic phenotype of MPSIIIA in several types of tissue, including brain tissue. The liver-directed approach was also able to produce high levels of circulating sulfamidase activity, which surprisingly corrected the somatic storage phenotype of MPSIIIA in full and significantly the neuropathology associated with the disease. These results provide evidence of the efficacy of AAV-mediated gene transfer of sulfamidase in adult MPSIIIA mice, a disease model closely resembling a human clinical setting. The inventors were able to completely correct both somatic and neurological alterations of MPSIIIA.

The gene constructions of the present invention may further comprise adequate promoters, such the CAG or hAAT promoters, to control and potentiate the expression of sulfamidase. For instance, the CAG promoter is more stable than the CMV promoter, and is thus more amenable to induce the expression of sulfamidase for longer periods of time. On the other hand, the safety and efficacy of the hAAT promoter make it an ideal vehicle for delivering follow-up or maintenance doses of sulfamidase. The control of the expression of SEQ ID NO: 1 by the CAG or hAAT promoters has potentiated significantly its therapeutic effects.

Also, the AAV vectors of the present invention increase the sulfamidase activity, which reduces the GAG accumulation and improves the clinical outcome of individuals suffering from MPS. Only one administration may be sufficient because the promoter and the nucleotide sequence of the sulfamidase, located between the inverted terminal repeats (ITR) are incorporated in the genome of the cells of the individual. Therefore, a single parenteral administration is enough to get a long-term effect.

In a third aspect, the invention relates to a pharmaceutical composition comprising the nucleotide sequence of the first aspect of the invention, the gene construction or the expression vector of the invention.

In a fourth aspect, the invention relates to the nucleotide sequence, the gene construction, the expression vector or the pharmaceutical composition of the invention for use as a medicament. The medicament may be used for increasing the sulfamidase activity in the body, for enzyme replacement therapy, for gene therapy or for the treatment of MPS.

In a fifth aspect, the invention relates to a method for the production of the expression vectors of the first and second aspect of invention.

In a sixth aspect, the invention relates to a method for manufacturing the pharmaceutical compositions of the third aspect of the invention.

In a seventh aspect, the invention relates to a method for treating a subject having mucopolysaccharidosis type IIIA with the first, second and third aspects of the invention.

The present invention also relates to the use of a nucleotide sequence, gene construction, expression vector or pharmaceutical compositions of the invention in the manufacture of a medicament for increasing the sulfamidase activity in the body, for enzyme replacement therapy, for gene therapy or for the treatment of mucopolysaccharidoses or mucopolysaccharidosis type IIIA.

DEPOSIT OF MICROORGANISMS

Figure 1:
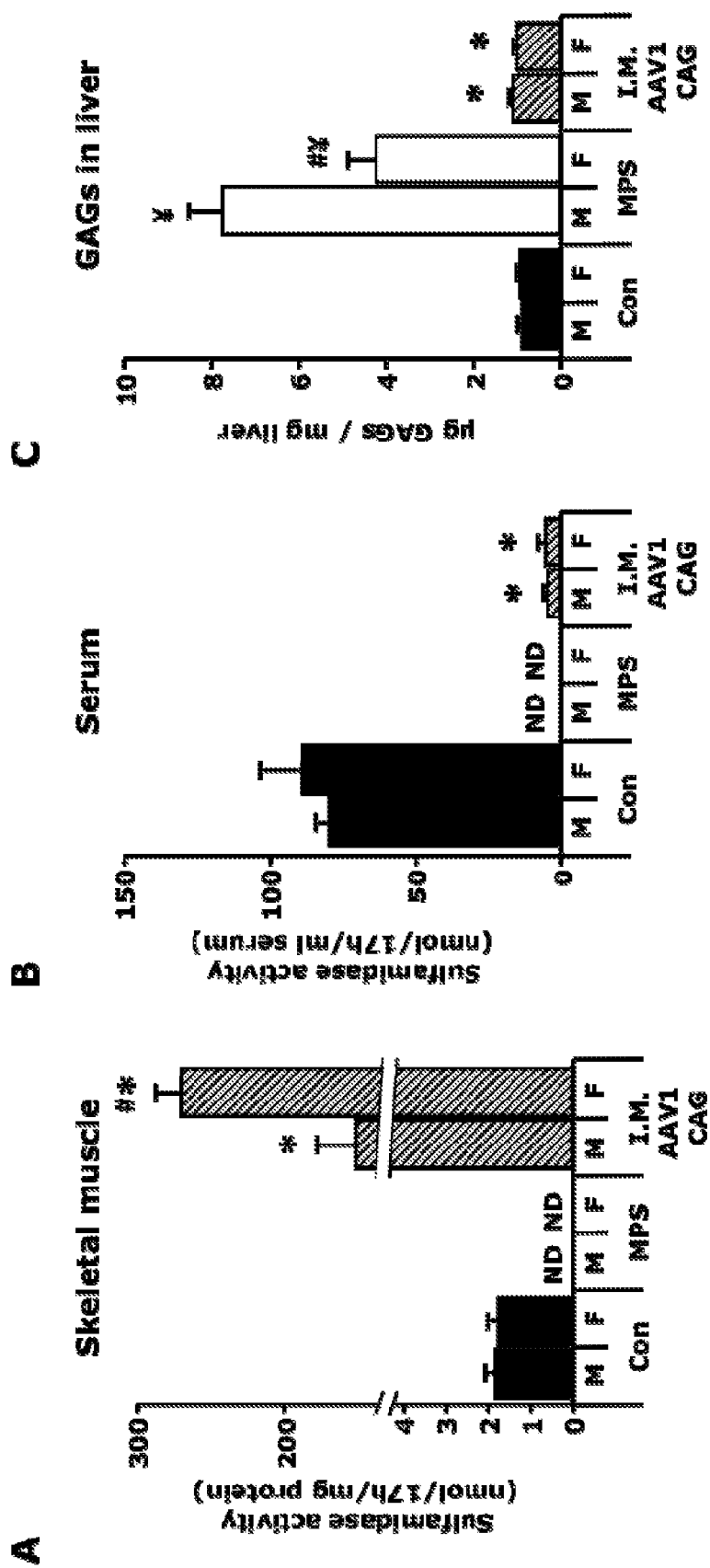
FIG. 1. Intramuscular delivery of AAV1-CAG-mu-SFMD-WPRE. (A) Sulfamidase activity in skeletal muscle of control, MPS and treated mice. (B) Sulfamidase activity in serum of control, MPS and treated mice. (C) Glycosaminoglycan (GAG) quantification in liver of control, MPS and treated mice. Values are means±SEM of 4 to 8 mice per group. ¥P<0.05 vs. control, #P<0.05 vs. males, * P<0.05 vs. untreated MPS. ND: not detected.

The plasmid pAAV-CAG-co-hu-SFMD was deposited on May 16, 2011, under access number DSM 24817 at the DSMZ—Deutsche Sammlung von Mikroorganismen und Zellkulturen, Inhoffenstraβe 7 B, D-38124 Braunschweig, Federal Republic of Germany.

The plasmid pAAV-CAG-mu-SFMD was deposited on May 16, 2011, under access number DSM 24818 at the DSMZ—Deutsche Sammlung von Mikroorganismen und Zellkulturen, Inhoffenstraβe 7 B, D-38124 Braunschweig, Federal Republic of Germany.

The plasmid pGG2-hAAT-mu-SFMD was deposited on May 16, 2011, under access number DSM 24819 at the DSMZ—Deutsche Sammlung von Mikroorganismen und Zellkulturen, Inhoffenstraβe 7 B, D-38124 Braunschweig, Federal Republic of Germany.

DEFINITIONS

The term "nucleotide sequence" refers to a nucleic acid molecule, either DNA or RNA, containing deoxyribonucleotides or ribonucleotides. The nucleic acid may be double stranded, single stranded, or contain portions of both double stranded or single stranded sequence.

The term "% sequence identity" refers to the percentage of nucleotides of a candidate sequence that are identical to the nucleotides in SEQ ID NO: 1, after aligning the sequences to achieve the maximum % sequence identity. The % sequence identity can be determined by any methods or algorithms established in the art, such as the ALIGN, BLAST and BLAST 2.0 algorithms. See Altschul S, et al., Nuc. Acids Res. 1977; 25:3389-3402 and Altschul S, et al., J. Mol. Biol. 1990; 215:403-410.

Herein, the % sequence identity is calculated dividing the number of nucleotides that are identical after aligning SEQ ID NO: 1 and the candidate sequence, by the total number of nucleotides in SEQ ID NO: 1 and multiplying the result by 100.

The term "codify" refers to the genetic code that determines how a nucleotide sequence is translated into a polypeptide or a protein. The order of the nucleotides in a sequence determines the order of amino acids along a polypeptide or a protein.

The term "protein" refers to a linear chain of amino acids or a polypeptide that is folded into a globular form. Proteins can suffer post-translational modifications, like the conversion of a cysteine residue to 3-oxoalanine, glycosylation or metal binding. Glycosilation of a protein is the addition of different carbohydrates that are linked covalently to the amino acid chain.

The term "effective amount" refers to an amount of a substance sufficient to achieve the intended purpose. For example, an effective amount of an expression vector to increase sulfamidase activity is an amount sufficient to reduce glycosaminoglycan accumulation. A "therapeutically effective amount" of an expression vector to treat a disease or disorder is an amount of the expression vector sufficient to reduce or remove the symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "individual" refers to an arbitrary animal, preferably human or non-human mammal, more preferably mouse, rat, other rodents, rabbit, dog, cat, pig, cow, horse or primate, further more preferably human.

The term "operably linked" refers to the functional relation and the location of the promoter sequence with respect to the gene of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

The term "tropism" refers to the way in which different viruses have evolved to preferentially target specific host species, or specific cell types within those species.

The term "gene therapy" refers to the transfer of genetic material (e.g. DNA or RNA) of interest into a host to treat or prevent a genetic or acquired disease or condition. The genetic material of interest encodes a product (e.g. a protein polypeptide, peptide or functional RNA) whose production in vivo is desired. For example, the genetic material of interest can encode an enzyme, hormone, receptor, or polypeptide of therapeutic value.

The term "CAG promoter" refers to the combination formed by the cytomegalovirus early enhancer element and chicken β-actin promoter (i.e. SEQ ID NO: 3). See Alexopoulou A, et al., BMC Cell Biology 2008; 9(2): 1-11.

The term "hATT promoter" refers to the human alpha1-antitrypsin promoter (i.e. SEQ ID NO: 4). See Hafenrichter H, et al., Blood 1994; 84: 3394-3404.

The term "viral vector particle" refers to the genetically modified virus used for the delivery of genes into an organism. The viral vector particles carry the viral genome. The viral genome comprises the nucleotide sequence that is located between the ITRs in the expression vector used for the production of the viral vector particles. The adeno-associated viral vector particles are called AAV. The term "AAV vector" refers to the adeno-associated viral vector particles.

DETAILED DESCRIPTION OF THE INVENTION

In a preferred embodiment, the sequence of the first aspect of the invention has at least 85%, sequence identity to SEQ ID NO: 1 that codifies for the protein SEQ ID NO: 2. Preferably, the sequence identity is at least 87%. More preferably, the sequence identity is at least 90%. Much more preferably, the sequence identity is at least 95%. Even more preferably, the sequence identity is at least 98%. Most preferably, the sequence identity is at least 99%. In a more preferred embodiment, the sequence of the first aspect of the invention is nucleotide sequence SEQ ID NO: 1. In another embodiment, the invention relates to a nucleotide sequence SEQ ID NO: 1 or a biologically active variant of this sequence. A biologically active variant includes a molecule having the same biological activity as SEQ ID NO: 1 and at least 85% sequence identity. Biological activity refers to the fact that the nucleotide sequence SEQ ID NO: 1 can be transcribed into a messenger RNA that has increased stability and therefore presents high translation rates, therefore allowing the expression of high levels of active human sulfamidase.

In a preferred embodiment of the second aspect, the gene construction comprises a nucleotide sequence having at least 85%, preferably 87%, 90%, 95%, 98%, 99% sequence identity to SEQ ID NO: 1. In a more preferred embodiment, the gene construction comprises nucleotide sequence SEQ ID NO: 1. A gene construction is nucleic acid molecule where different elements have been engineered in a specific and desired manner. These elements may be, among others, replicating sequences, control sequences, codifying sequences, multicloning sequences or recombination sequences. In a preferred embodiment, the gene construction is a vector. A vector is a nucleic acid molecule used to transfer genetic material into a cell. Apart form the said genetic material, a vector may also contain different functional elements that include control elements for transcription, like promoters or operators, transcription factor binding regions or enhancers, and control elements for the initiation or termination of translation. Vectors include, but are not limited to: plasmids, cosmids, viruses, phages, recombinant expression cassettes and transposons. The adeno-associated vectors (AAV) are the viral vector particles, therefore they are not a nucleic acid molecule but a genetically modified virus used for the delivery of genes into an organism.

In a preferred embodiment of the second aspect of the invention, the gene construction is a vector that is used for the translation and transcription of a gene of interest, usually controlled by a promoter. A promoter is a nucleotide sequence that controls the translation of the gene of interest. The promoter is operably linked to the gene of interest.

Another preferred vector is an adeno-associated vector. In a preferred embodiment, the adeno-associated vector is used to produce adeno-associated particles where the serotype is 1, 2, 5, 7, 8 or 9. In a more preferred embodiment, the serotype is 9. An adeno-associated vector is a vector derived from the genome of an adeno-associated virus (AAV) of the family Parvoviridae. The AAV genome is built of single-stranded deoxyribonucleic acid (ssDNA). AAV infect humans but are non-pathogenic (i.e. do not cause a disease). They can infect dividing and non-dividing cells, and their tropism changes depending on the serotype. The serotype is the classification of the viruses in groups, depending on their capsid antigens. The serotype of the AAV, determined by its capsid proteins, defines the virus tropism and allows its entry into a specific cell type. The production of the adeno-associated vector particles is described below.

In a first preferred embodiment of the second aspect, the expression vector comprises the CAG promoter operably linked to SEQ ID NO: 1.

A preferred vector is an expression vector comprising the CAG promoter, the promoter sequence being SEQ ID NO: 3. Therefore, one embodiment of the second aspect of the invention is an expression vector comprising CAG promoter, the promoter sequence being SEQ ID NO: 3 suitable for treating MPS.

In a second preferred embodiment of the second aspect, the expression vector comprises the liver-specific hAAT promoter operable linked to SEQ ID NO: 1.

A preferred vector is an expression vector comprising the liver-specific hAAT promoter, the promoter sequence being SEQ ID NO: 4. Therefore, one embodiment of the second aspect of the invention is an expression vector comprising the liver-specific hAAT promoter, the promoter sequence being SEQ ID NO: 4 suitable for treating MPS.

Another aspect of the present invention refers to a viral vector particle, also called expression vector, which carries the nucleotide sequences of the first aspect of the invention, or the gene construction or expression vector of the second aspect of the invention.

A preferred expression vector has serotype 1, 2, 5, 7, 8 or 9. A more preferred viral vector particle has serotype 9.

A preferred expression vector has serotype 9 and comprises a viral genome comprising a CAG promoter operably linked to SEQ ID NO: 1.

A preferred expression vector has serotype 8 or 9 and comprises a viral genome comprising a hAAT promoter operably linked to SEQ ID NO: 1.

A preferred expression vector has serotype 9 and comprises a viral genome comprising a hAAT promoter operably linked to SEQ ID NO: 1.

In a preferred embodiment, the expression vector is AAV-CAG-co-hu-SFMD and more preferably, AAV9-CAG-co-hu-SFMD.

In yet another preferred embodiment, the expression vector is AAV-hAAT-co-hu-SFMD, and more preferably, AAV8-hAAT-co-hu-SFMD or pAAV9-hAAT-co-hu-SFMD. The most preferred vector utilized when the hAAT promoter is used is AAV9-hAAT-co-hu-SFMD.

In a preferred embodiment of the third aspect, the pharmaceutical composition is administered by parenteral administration. Parenteral administration refers to the route of administration of a pharmaceutical composition as an injection or infusion. Examples of parenteral administration are intravenous, subcutaneous, intracisternal and intramuscular injections. Preferably, the pharmaceutical composition is administered by intravenous or intracisternal administration In another preferred embodiment, the pharmaceutical composition comprises a therapeutically effective amount of the nucleotide sequence, the gene construction, the viral vector particle or the expression vector of the invention.

In a preferred embodiment of the fourth aspect, the nucleotide sequence, the gene construction, the expression vector, the viral vector particle or the pharmaceutical composition of the invention are used as a medicament. In a preferred embodiment, they are used for increasing the sulfamidase activity in the body.

In another preferred embodiment, the nucleotide sequence, the gene construction, the expression vector, the viral vector particle or the pharmaceutical composition of the invention are used as a medicament for enzyme replacement or gene therapy, preferably gene therapy. The inventors propose a new gene therapy approach for the treatment of MPSIIIA therapeutic that is more efficacious than other known in the art. This approach is based on AAV vectors expressing sulfamidase. The enzyme replacement therapy (ERT) is a medical treatment that consists in replacing an enzyme in patients where a particular enzyme is deficient or absent. The enzyme is usually produced as a recombinant protein and administrated to the patient.

In a further embodiment, the nucleotide sequence, the gene construction, the expression vector, the viral vector particles or the pharmaceutical composition of the invention are preferably used for the treatment of mucopolysaccharidoses, more preferably of mucopolysaccharidosis type III or Sanfilippo syndrome, preferably through gene therapy. Within the mucopolysaccharidosis type III syndrome the subtype A is especially amenable to respond to treatment with the present invention.

In a preferred embodiment of the fifth aspect, a method for the production of the expression vectors of the invention is claimed. The process comprises the steps of:

i) providing a first vector comprising the SEQ ID NO: 1 interposed between a first AAV terminal repeat and a second AAV terminal repeat, a CAG or hAAT promoter operably linked to the SEQ ID NO: 1; a second vector comprising an AAV rep gene and a AAV cap gene; and a third vector comprising the adenovirus helper function gene;

ii) co-transfecting competent cells with the vectors of step i);

iii) culturing the transfected cells of step ii); and iv) purifying the expression vectors from the culture of step iii).

In a preferred embodiment, the AAV first and second terminal repeats of the first vector are ITRs from the AAV serotype 2. In another preferred embodiment, the AAV rep genes of the second vector are from the AAV serotype 2. In yet another preferred embodiment, the AAV cap genes of the second vector are from the AAV serotypes 1, 2, 5, 7, 8 or 9. More preferably, the AAV cap genes of the second vector are from the AAV serotype 9. In another preferred embodiment, the competent cells are HEK293 cells.

The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts.

In a preferred embodiment of the sixth aspect, a method for manufacturing the pharmaceutical compositions of the invention is claimed. This method comprises combining any of the nucleotide sequences, gene constructions, viral vector particles or expression vectors of the invention and a pharmaceutically acceptable vehicle or carrier to facilitate administration to yield the pharmaceutical compositions of the invention. The carrier is, for instance, water, or a buffered saline solution, with or without a preservative. The pharmaceutical compositions may be lyophilized for re-suspension at the time of administration or in solution.

In a preferred embodiment of the seventh aspect, a method for treating a subject having mucopolysaccharidosis type IIIA with the nucleotide sequences, gene constructions, viral vector particles, expression vectors or pharmaceutical compositions of the invention is claimed. Schedules and dosages for the administration of the nucleotide sequences, gene constructions, vectors, expression vectors or pharmaceutical compositions according to the present invention can be determined in accordance to dosage protocols known in the art. In a preferred embodiment, the nucleotide sequences, gene constructions, viral vector particles, expression vectors or pharmaceutical compositions according to the present invention are administered once.

In one additional embodiment, a pharmaceutical composition for gene therapy treatment of MPS consists in the parenteral administration of an expression vector comprising a nucleotide sequence having 90% sequence identity to SEQ ID NO: 1.

In another additional embodiment, a viral vector comprising the CAG promoter and a nucleotide sequence having 95% sequence identity to SEQ ID NO: 1 is used for gene therapy for the treatment of a lysosomal storage disease (LSD) by an intramuscular injection.

In another additional embodiment, an AAV vector with serotype 1 comprising the CAG promoter and a nucleotide sequence having 87% sequence identity to SEQ ID NO: 1 is used as a medicament to treat MPS and is administered intravenously.

In another additional embodiment, a pharmaceutical composition comprising a nucleotide sequence having 98% sequence identity to SEQ ID NO: 1 and an ubiquitous promoter is administered parenterally to treat a disease.

Having described the invention in general terms, it will be more easily understood by reference to the following examples which are presented as an illustration and are not intended to limit the present invention.

General Procedures

1. Recombinant AAV Vectors

The AAV vectors described herein were constructed by triple transfection. The materials required for making the vectors were: HEK293 cells (expressing E1 genes), helper plasmid providing adenovirus function, helper plasmid providing AAV rep genes from serotype 2 and cap genes from the desired serotype (i.e. AAV1, AAV2, AAV5, AAV7, AAV8, AAV9) and, finally, the backbone plasmid with ITRs and the construct of interest. To generate sulfamidase-expressing AAV vectors, the cDNA of murine sulfamidase was cloned into an AAV backbone plasmid under the control of the ubiquitous hybrid CAG promoter or the liver-specific hAAT promoter.

Vectors (viral vector particles) were generated by helper virus-free transfection of HEK293 cells using three plasmids with modifications. See Matsushita T, et al., Gene Ther. 1998; 5:938-945 and Wright J, et al., Mol. Ther. 2005; 12:171-178. Cells were cultured to 70% confluence in roller bottles (RB) (Corning, Corning, N.Y., US) in DMEM (Dulbeccos's Modified Eagle Medium) supplemented with 10% FBS (Foetal Bovine Serum) and then co-transfected with: 1) a plasmid carrying the expression cassette flanked by the viral ITRs (described above); 2) a helper plasmid carrying the AAV rep2 and the correspondent cap (cap1 and cap9 genes; and 3) a plasmid carrying the adenovirus helper functions. Vectors were purified by two consecutives cesium chloride gradients using either a standard protocol or an optimized protocol as previously described. See Ayuso E, et al., Gene Ther. 2010; 17:503-510. Vectors were dialyzed against PBS, filtered, titred by qPCR (quantitative Polymerase Chain Reaction) and stored at −80° C. until use.

a. Construction of pAAV-CAG-mu-SFMD-WPRE

Murine sulfamidase cDNA was utilized as starting material (Clone ID: D330015N16; Riken, Saitama, J P). The cDNA was received inside the plasmid pFLCI-Sgsh. High-fidelity PCR was performed to amplify the sulfamidase codifying region with primers that included MluI restriction sites at both ends. The sequences of the respective sense and antisense primers were: SEQ ID NO: 5 (Fw) CTTACTTATGACGCGTATGCACTGCCCGGGACTG and SEQ ID NO: 6 (Rv) TATCCTATCGACGCGTTCAGAGTTCATTGTGAAGCGGTC.

The backbone plasmid pAAV-CAG-WPRE was generated previously and contained both ITRs from the AAV2 genome, the CAG promoter, the WPRE element and the polyA signal of rabbit β-globin. The CAG promoter is a hybrid promoter composed of the CMV early/intermediate enhancer and the chicken β-actin promoter. This promoter is able to drive a potent expression ubiquitously. The woodchuck hepatitis virus post-transcriptional regulatory element (WPRE) is a hepadnavirus sequence that is widely used as a cis-acting regulatory module in various types of plasmid or viral gene vectors. When placed in the 3' untranslated region of gene transfer cassettes, the WPRE enhances the production of the transgene by increasing both nuclear and cytoplasmic mRNA levels. See Zanta-Boussif M, et al., Gene Ther. 2009; 16:605-619.

The PCR-amplified sulfamidase coding region was cloned into the MluI restriction site of the AAV backbone plasmid pAAV-CAG-WPRE, and the resulting plasmid was named pAAV-CAG-mu-SFMD-WPRE. See SEQ ID NO: 7.

b. Construction of pAAV-CAG-mu-SFMD

The WPRE element in the pAAV-CAG-mu-SFMD-WPRE plasmid is flanked by two EcoRI restriction sites. To generate the pAAV-CAG-mu-SFMD plasmid (accession number DSM 24818), the pAAV-CAG-mu-SFMD-WPRE plasmid was digested with EcoRI, to eliminate the WPRE sequence, and was then subsequently religated. See SEQ ID NO: 8.

c. Construction of pAAV-CAG-co-hu-SFMD

The pAAV-CAG-mu-SFMD plasmid was digested with MluI and EcoRI to remove the murine sulfamidase codifying region. Subsequently, the cDNA of the codon optimized human sulfamidase (co-hu-SFMD) was digested and cloned at the same restriction sites to generate the pAAV-CAG-co-hu-SFMD plasmid (accession number DSM 24817). See SEQ ID NO: 9.

d. Construction of pAAV9-CAG-hu-SFMD

The pAAV9-CAG-hu-SFMD vector was obtained by co-transfecting 293HEK cells with the pAAV-CAG-co-hu-SFMD plasmid, a plasmid encoding the adenovirus helper function and a plasmid encoding AAV2 rep and AAV9 cap genes.

e. Construction of pGG2-hAAT-mu-SFMD

The murine sulfamidase codifying region was excised from the pAAV-CAG-mu-SFMD-WPRE plasmid by digestion with MluI. This region was then cloned into the MluI site in the AAV backbone plasmid pGG2-hAAT to yield the pGG2-hAAT-mu-SFMD plasmid (accession number DSM 24819). See SEQ ID NO: 10.

f. Construction of pGG2-hAAT-co-hu-SFMD

The codon optimized human sulfamidase codifying region was excised from the pAAV-CAG-co-hu-SFMD plasmid (accession number DSM 24817) by digestion with MluI-EcoRI. The pGG2-hAAT-mu-SFMD plasmid (accession number DSM 24819) was digested with MluI to remove mu-SFMD gene and, afterwards, the codon optimized human sulfamidase codifying region was cloned in this site by blunt-end ligation. The resulting plasmid was named as pGG2-hAAT-co-hu-SFMD. See SEQ ID NO: 11.

The pGG2-hAAT-co-hu-SFMD plasmid contained both AAV2-ITRs, the hAAT promoter and the SV40-derived polyadenylation signal.

g. Construction of AAV9-hAAT-co-hu-SFMD and AAV8-hAAT-co-hu-SFMD

Vectors were generated by helper virus-free transfection of HEK293 cells using three plasmids with modifications. See Matsushita, 1998, supra and Wright, 2005, supra. Cells were cultured to 70% confluence in roller bottles (RB) (Corning, Corning, N.Y., US) in DMEM supplemented with 10% FBS and then co-transfected with: 1) a plasmid carrying the expression cassette flanked by the viral ITRs (pGG2-hAAT-co-hu-SFMD); 2) a helper plasmid carrying the AAV rep2 and the correspondent cap genes (cap8 or 9); and 3) a plasmid carrying the adenovirus helper functions. Vectors were purified by two consecutives cesium chloride gradients using either a standard protocol or an optimized protocol as previously described. See Ayuso, 2010, supra. Vectors were dialyzed against PBS, filtered, titred by qPCR and stored at −80° C. until use.

The pGG2-hAAT-mu-SFMD plasmid contained both AAV2-ITRs, the hAAT promoter and the SV40-derived polyadenylation signal. The hAAT promoter is a hybrid promoter composed of the 4 tandem repeats of the hepatocyte control region (HCR) enhancer from the apolipoprotein E and the human α-anti-trypsin promoter. Its expression is restricted to hepatocytes. See Mingozzi F, et al., J. Clin. Invest. 2003; 111:1347-1356.

The vectors of the present invention were constructed according to molecular biology techniques well known in the art. See Brown T, "Gene Cloning" (Chapman & Hall, London, GB, 1995); Watson R, et al., "Recombinant DNA", 2nd Ed. (Scientific American Books, New York, N.Y., US, 1992); Alberts B, et al., "Molecular Biology of the Cell" (Garland Publishing Inc., New York, N.Y., US, 2008); Innis M, et al., Eds., "PCR Protocols. A Guide to Methods and Applications" (Academic Press Inc., San Diego, Calif., US, 1990); Erlich H, Ed., "PCR Technology. Principles and Applications for DNA Amplification" (Stockton Press, New York, N.Y., US, 1989); Sambrook J, et al., "Molecular Cloning. A Laboratory Manual" (Cold Spring Harbor Laboratory Press, Cold Spring Harbor, N.Y., US, 1989); Bishop T, et al., "Nucleic Acid and Protein Sequence. A Practical Approach" (IRL Press, Oxford, GB, 1987); Reznikoff W, Ed., "Maximizing Gene Expression" (Butterworths Publishers, Stoneham, Mass., US, 1987); Davis L, et al., "Basic Methods in Molecular Biology" (Elsevier Science Publishing Co., New York, N.Y., US, 1986), Schleef M, Ed., "Plasmid for Therapy and Vaccination" (Wiley-VCH Verlag GmbH, Weinheim, Del., 2001).

2. Animals

A congenic C57Bl/6 sulfamidase-deficient mouse colony (MPSIIIA) was used. See Crawley A, et al., Brain Res. 2006; 1104:1-17. Affected MPSIIIA and healthy control mice were inbred from heterozygous founders. Genotype was determined by PCR analysis on genomic DNA from tail-clipped samples, which amplifies a sequence encompassing the mutation, and its subsequent digestion with MspA1I restriction enzyme, as previously described. See Bhattacharyya R, et al., Glycobiology 2001; 11:99-103. Mice were fed ad libitum with a standard diet (Panlab, Barcelona, ES) and maintained under a light-dark cycle of 12 h (lights on at 9:00 A.M.).

3. Vector Administration and Sample Collection

For intravenous delivery of AAV vectors, a total dose of $10^{12}$ vector genomes of the appropriate AAV vector were injected into 2-month-old MPSIIIA animals via tail vein. For intramuscular injection, 2-month-old MPSIIIA animals were anesthetized with a mixture of ketamine (100 mg/kg) and xylacine (10 mg/kg), and a total dose of $10^{12}$ vector genomes of the appropriate AAV vector were injected into 6 muscles of the hind limbs (quadriceps, gastrocnemius and tibialis anterior from both legs). At 10 months of age, mice were anesthetized and then transcardially perfused with 10 ml of PBS to completely clear blood from tissues. The entire brain and multiple somatic tissues (including liver, spleen, pancreas, kidney, lung, heart, skeletal muscle and testicles) were collected and either frozen in liquid nitrogen and stored at −80° C. or immersed in formalin for subsequent histological analyses.

4. RNA Analysis

Total RNA was obtained from skeletal muscle and liver samples by using TriPure Isolation Reagent (Roche Diagnostics, Barcelona, ES) and analyzed by Northern blot. Blots were hybridized with a murine sulfamidase probe, labeled with $^{32}$P-dCTP by random priming with Ready-to-Go DNA Labelling Beads (Amersham Biosciences, Piscataway, N.J., US).

5. Sulfamidase Activity and Glycosaminoglycan Quantification

Liver, skeletal muscle and brain samples were sonicated in water and sulfamidase activity was assayed in supernatants with a 4-methylumbelliferone-derived fluorogenic substrate (Moscerdam Substrates, Oegstgeest, NL) as described previously. See Karpova E, et al., J. Inherit. Metab. Dis. 1996; 19:278-285. Sulfamidase activity levels were normalized against the total amount of protein, quantified using the Bradford protein assay (Bio-Rad, Hercules, Calif., US).

For glycosaminoglycan (GAG) quantification, tissue samples were weighted and then digested with proteinase K and extracts were clarified by centrifugation and filtration. GAG levels in tissue extracts and urine were determined using Blyscan sulfated glycosaminoglycan kit (Biocolor, Carrickfergus, County Antrim, GB) with chondroitin 4-sulfate as the standard. GAG levels in tissues were normalized to wet tissue weight and in urine to creatinine concentration, measured with a specific kit (Horiba ABX, Irvine, Calif., US).

6. Histological Analyses

Tissues were fixed for 12-24 h in formalin, embedded in paraffin and sectioned followed by heat-induced epitope retrieval (citrate buffer, pH 6). For immunohistochemical detection of LAMP1, paraffin sections were incubated overnight at 4° C. with rat anti-LAMP1 antibody (1D4B; Santa Cruz Biotechnology, Santa Cruz, Calif., US) diluted at 1:100 and subsequently incubated with biotinylated rabbit anti-rat antibody (Dako, Glostrup, DK) at 1:300. LAMP1 signal was amplified by incubating sections with ABC-Peroxidase staining kit (Thermo Scientific, Waltham, Mass., US) at 1:100 and visualized by using 3,3-diaminobenzidine (Sigma-Aldrich, St. Louis, Mo., US) as a chromogen. Brightfield images were obtained with an optical microscope (Eclipse E800; Nikon, Tokyo, JP). For parvalbumin and calbindin immunostaining, paraffin sections were incubated overnight at 4° C. with rabbit anti-calbindin D28k (Swant, Marly, CH) diluted at 1:2000 or with rabbit anti-parvalbumin (Swant, Marly, CH) diluted at 1:100. Afterwards, samples were incubated with the biotinylated goat anti-rabbit IgG (Vector Labs., Burlingame, Calif., US), and then with streptavidin-Alexa 488 (1:100, Molecular Probes, Invitrogen, Carlsbad, Calif., US), and nuclei were stained with T#PRO-3. Images were obtained with a confocal microscope (Leica Microsystems, Heidelberg, Del.).

For double immunostaining LAMP1 and Mac2, sections were first incubated overnight at 4° C. with rat anti-LAMP1 antibody at 1:100, then with biotinylated rabbit anti-rat antibody at 1:300 followed by an incubation with streptavidin-Alexa 488 (1:300). Afterwards, sections were incubated with rabbit anti-Mac2 at 1:50, then with biotinylated goat anti-rabbit at 1:300 followed by incubation with streptavidin-Alexa 568 (1:300; Molecular Probes, Invitrogen, Carlsbad, Calif., US). Finally, nuclei were stained with Hoechst (1:100; Sigma-Aldrich, St. Louis, Mo., US).

7. Western Blot Analysis

Halves of cerebellum were homogenized in protein lysis buffer. Ten micrograms of protein were run on a 10% (wt/vol) SDS-PAGE, transferred to polyvinylidene difluoride membranes and probed overnight at 4° C. with primary antibodies against calbindin (Swant, Marly, CH) and α-tubulin (Abcam, Cambridge, Mass., US). Detection was performed using horseradish peroxidase-labelled swine anti-rabbit antibody (Dako, Glostrup, DK) and ECL Plus Western blotting detection reagent (Amersham Biosciences, Piscataway, N.J., US).

8. Transmission Electron Microscopic Analysis

Mice were sacrificed by an overdose of isofluorane (Isofluo, Labs. Esteve, Barcelona, ES) and perfused via inferior vena cava with 1 ml of 2.5% glutaraldehyde and 2% paraformaldehyde. A small portion (approximately 1 mm$^3$) of the lateral lobe of the liver and of the culmen of the cerebellum were sectioned and incubated for 2 hours at 4° C. in the same fixative. After washing in cold cacodylate buffer, the specimens were postfixed in 1% osmium tetroxide, stained in aqueous uranyl acetate, and then dehydrated through a graded ethanol series and embedded in epoxy resin. Ultrathin sections (600-800 Å) from the resin blocks were stained using lead citrate and examined in a transmission electron microscope (H-7000; Hitachi, Tokyo, JP).

9. Statistical Analysis

All results are expressed as mean±SEM. Statistical comparisons were made using either t-test or one-way ANOVA. Statistical significance was considered if P<0.05.

EXAMPLES

Example 1

Intramuscular Delivery of
AAV1-CAG-mu-SFMD-WPRE

A total dose of 10$^{12}$ vector genomes of the AAV1-CAG-mu-SFMD-WPRE vector was injected into 6 muscles of the hind limbs (quadriceps, gastrocnemius and tibialis anterior from both legs) of 2-month-old male and female MPSIIIA mice.

Eight months after the administration, the injected muscles displayed high levels of vector-derived sulfamidase expression and activity, but very low levels of sulfamidase activity were observed in serum (6-7% of control mice), suggesting low secretion efficiency from the skeletal muscle. See FIGS. 1A and 1B. In addition, very low but significant vector-derived sulfamidase expression was observed in the liver of these mice, indicating that, at the moment of injection, the vector leaked from the skeletal muscle into the circulation and transduced the liver. Even with the low levels of circulating sulfamidase activity achieved, correction of GAG accumulation was seen in liver, and a significant reduction in some other somatic tissues (spleen, heart, pancreas), but not in others (kidney, lung). See FIG. 1C. No reduction of the GAG storage was achieved in the brain.

Example 2

Intramuscular Delivery of
AAV8-CAG-mu-SFMD-WPRE

A total dose of 10$^{12}$ vector genomes of the AAV8-CAG-mu-SFMD-WPRE vector was injected into 6 muscles of the hind limbs (quadriceps, gastrocnemius and tibialis anterior from both legs) of 2-month-old male and female MPSIIIA mice.

Figure 2:
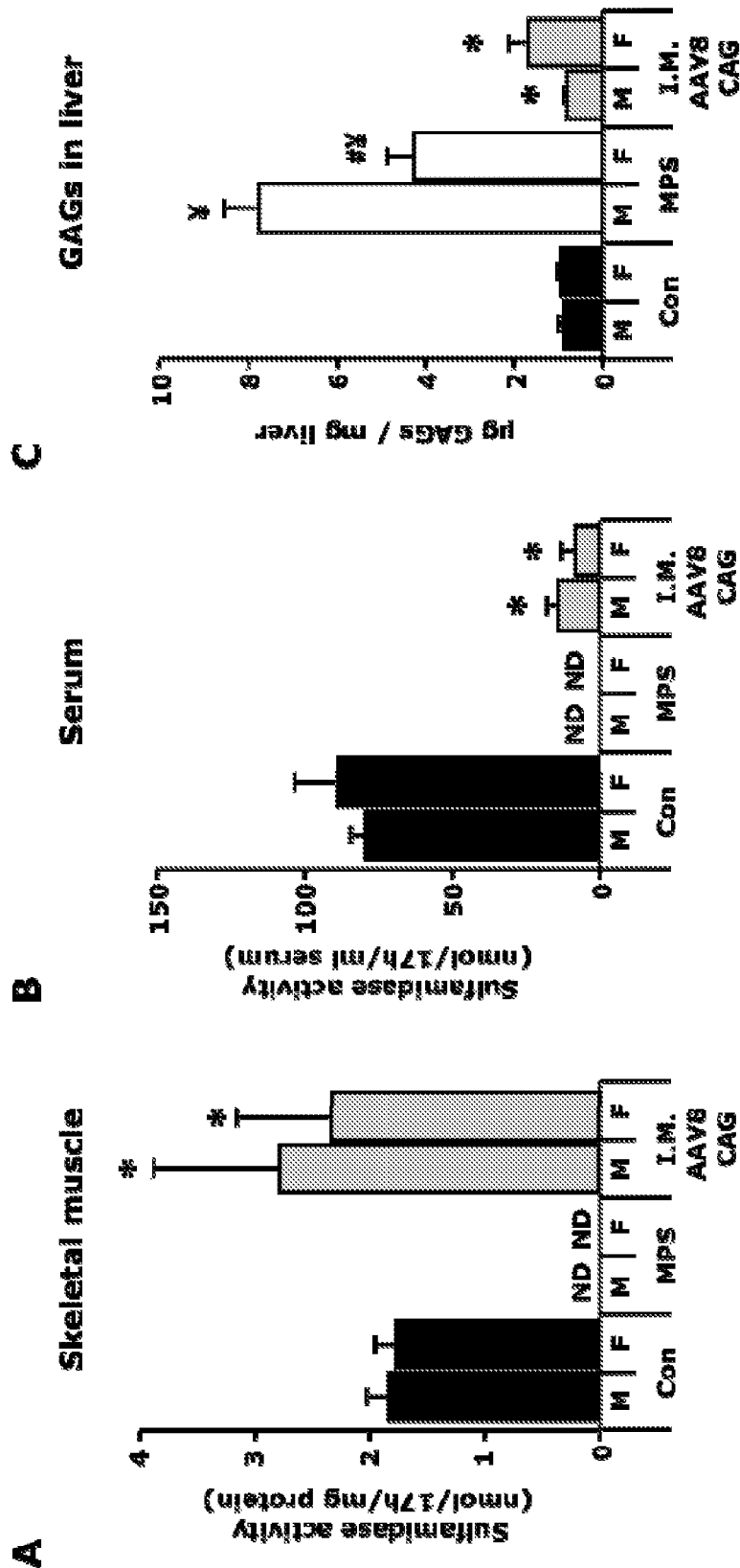
FIG. 2. Intramuscular delivery of AAV8-CAG-mu-SFMD-WPRE. (A) Sulfamidase activity in skeletal muscle of control, MPS and treated mice. (B) Sulfamidase activity in serum of control, MPS and treated mice. (C) Glycosaminoglycan (GAG) quantification in liver of control, MPS and treated mice. Values are means±SEM of 4 to 8 mice per group. ¥P<0.05 vs. control, #P<0.05 vs. males, * P<0.05 vs. untreated MPS. ND: not detected.

Eight months after the administration, the injected muscles displayed sulfamidase activity levels similar to those of a healthy control animal. See FIG. 2A. Low levels of sulfamidase activity were observed in serum (10-15% of control mice). See FIG. 2B. Vector leakage to the liver was also observed, since vector-derived sulfamidase expression and activity was seen in the liver, even at higher levels than in mice treated with intramuscular AAV1. See Example 1. Correction of GAG accumulation was seen in liver and spleen, and a greater reduction was observed in other somatic tissues (heart, pancreas, urinary bladder), but kidney and lungs remained largely uncorrected. See FIG. 2C. No reduction of the GAG storage was achieved in the brain.

Example 3

Intravenous Delivery of
AAV8-CAG-mu-SFMD-WPRE

A total dose of 10$^{12}$ vector genomes of the AAV8-CAG-mu-SFMD-WPRE vector was injected into 2-month-old MPSIIIA mice via tail vein.

Figure 3:
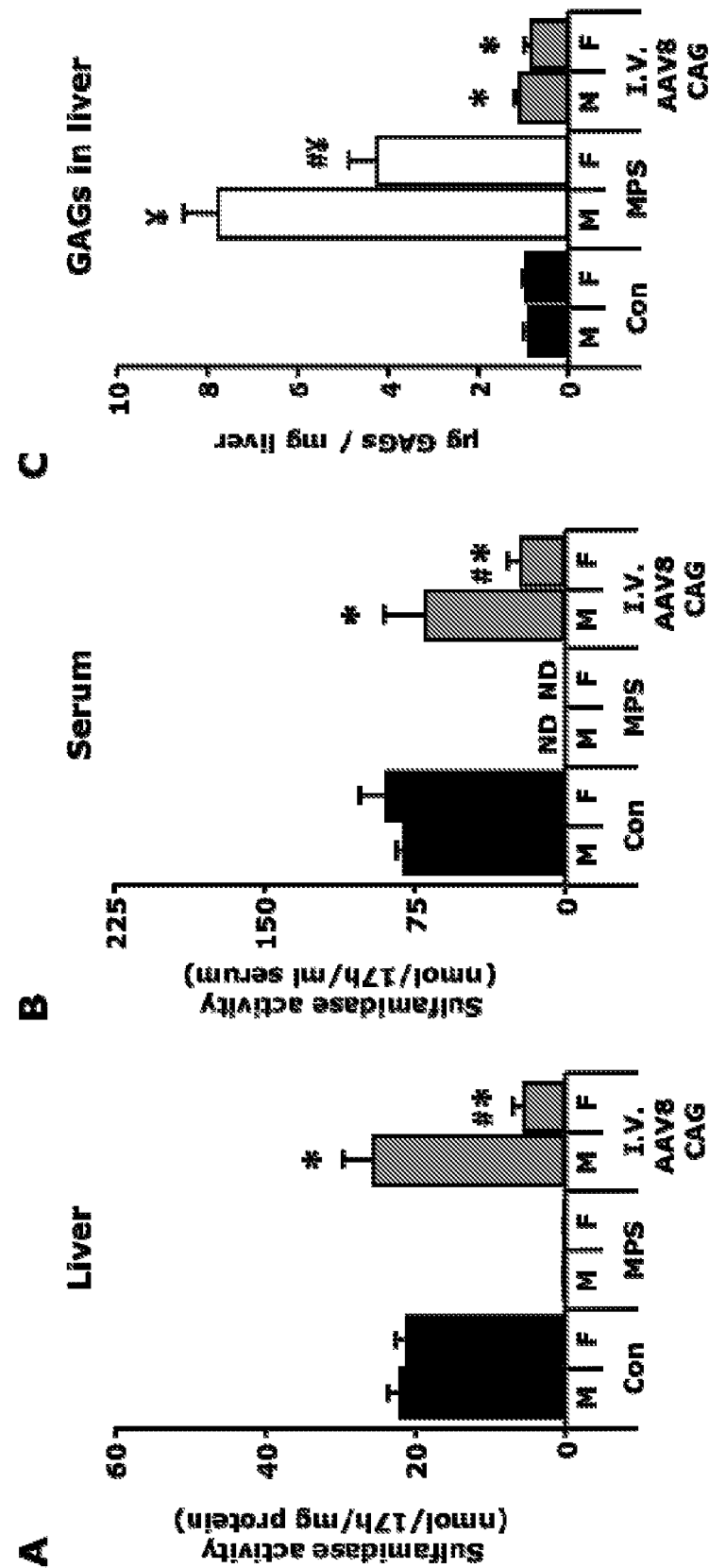
FIG. 3. Intravenous delivery of AAV8-CAG-mu-SFMD-WPRE. (A) Sulfamidase activity in liver of control, MPS and treated mice. (B) Sulfamidase activity in serum of control, MPS and treated mice. (C) Glycosaminoglycan (GAG) quantification in liver of control, MPS and treated mice. Values are means±SEM of 4 to 8 mice per group. ¥P<0.05 vs. control, #P<0.05 vs. males, * P<0.05 vs. untreated MPS. ND: not detected FIG. 4. Intravenous delivery of AAV8-hAAT-mu-SFMD. (A) Sulfamidase activity in liver of control, MPS and treated mice. (B) Sulfamidase activity in serum of control, MPS and treated mice. (C) Glycosaminoglycan (GAG) quantification in liver of control, MPS and treated mice. Values are means±SEM of 4 to 8 mice per group. ¥P<0.05 vs. control, #P<0.05 vs. males, * P<0.05 vs. untreated MPS. ND: not detected.

Eight months after administration, the treated males displayed sulfamidase activity in the liver at levels similar to those of control mice, but 4-fold lower in females. See FIG. 3A. Consistently, circulating sulfamidase activity was high in males (similar levels to those of control mice), and lower in females (25% of control mice). See FIG. 3B. Those high levels of circulating sulfamidase were able to correct GAG accumulation in liver, heart, spleen, pancreas and urinary bladder, and significantly reduce it in lungs, but not in kidney. See FIG. 3C for liver GAG quantification. No reduction of GAG storage was observed in the brain.

Example 4

Intravenous Delivery of AAV8-hAAT-mu-SFMD

A total dose of 10$^{12}$ vector genomes of the AAV8-hAAT-mu-SFMD vector was injected into 2-month-old MPSIIIA mice via tail vein.

Figure 4:
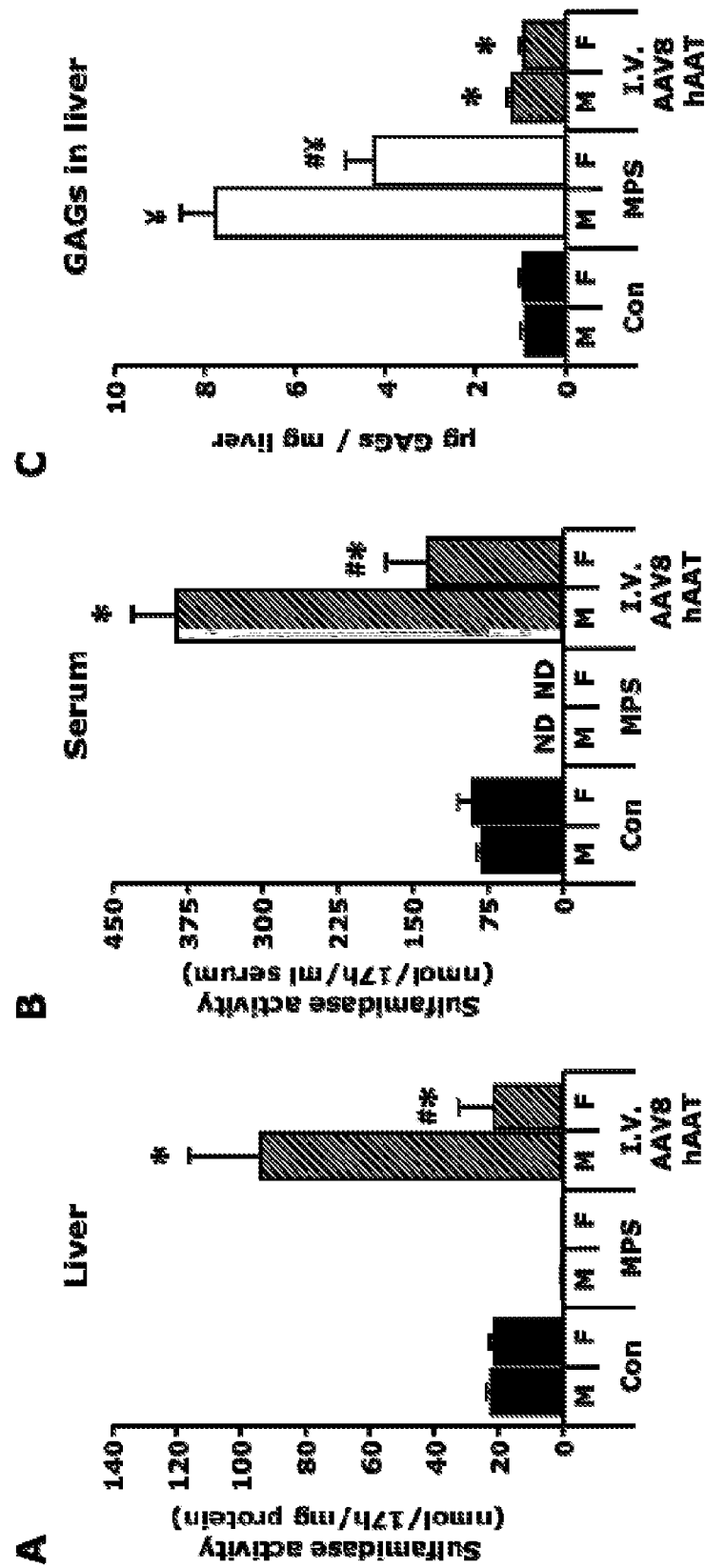

Eight months after administration, the treated males displayed a sulfamidase activity level in the liver 500% higher than in control animals. In the female subjects, the liver sulfamidase level reached the same level of the control subjects. See FIG. 4A. Circulating sulfamidase activity was consistently higher in males than in females (500% in males vs. 160% in females). See FIG. 4B. These supraphysiological levels of circulating sulfamidase were able to correct GAG accumulation in all somatic organs, including the kidney. See FIG. 4C for liver GAG quantification.

Figure 5:
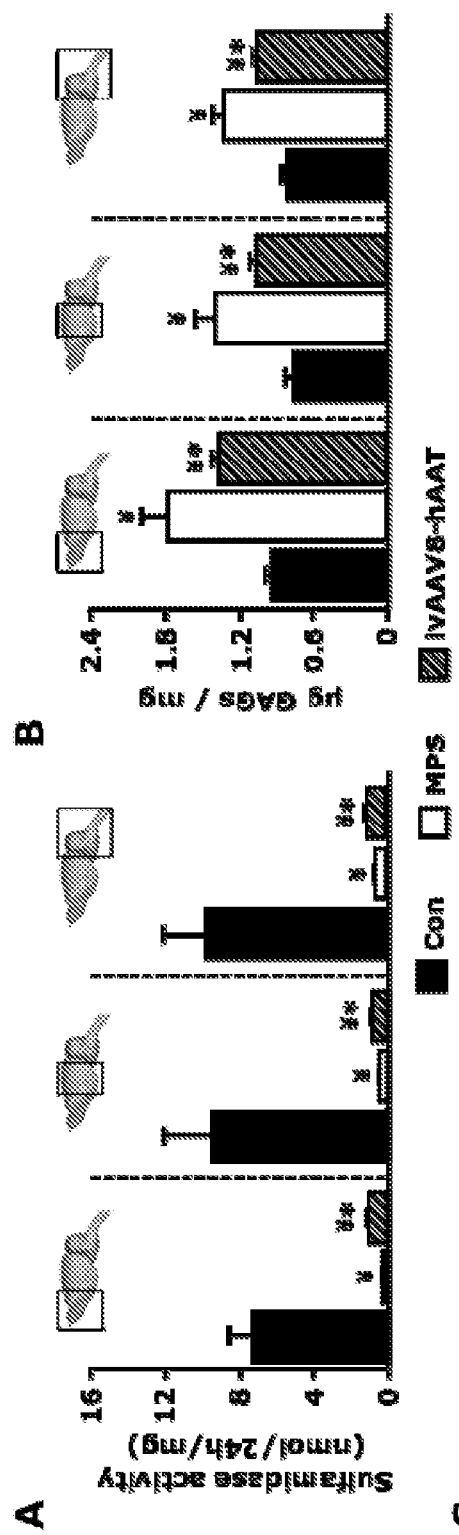
FIG. 5. Amelioration of the neurological pathology of MPSIIIA mice after intravenous delivery of AAV8-hAAT-mu-SFMD. (A) Sulfamidase activity in different parts of the brain (depicted in the diagram) of control, MPS and treated males. (B) Glycosaminoglycan (GAG) quantification in the same parts of the brain. Values are means±SEM of 4 to 8 mice per group. ¥P<0.05 vs. control, * P<0.05 vs. untreated MPS. ND: not detected. (C) Transmission electron microscopy of Purkinje cells in the cerebellum. Somas of Purkinje neurons of non-treated MPSIIIA mice were filled with many large electron-dense inclusions (white arrows), whereas in iv-AAV8-hAAT treated males less and smaller inclusions were found (black arrows).
Figure 5:
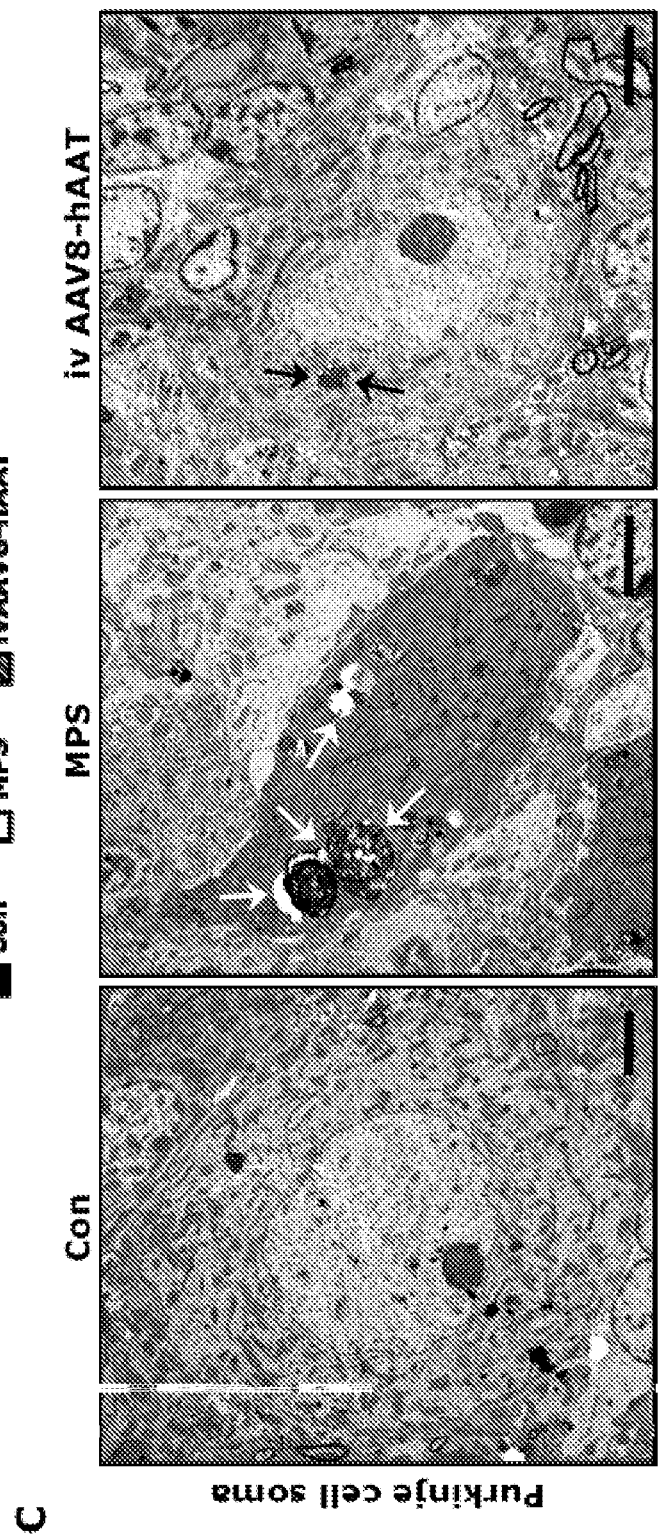

Treated males showed low levels of sulfamidase activity, and reduced GAG accumulation in brain. See FIGS. 5A and B. Purkinje cells of the cerebellum of treated males displayed less electron-dense inclusions when examined by electron microscopy. See FIG. 5C. The intravenous treatment with AAV8-hAAT-mu-SFMD vector ("iv-AAV8-hAAT-mu-SFMD") achieved the correction of the somatic pathology but only ameliorated the neurodegeneration characteristic of MPSIIIA mice.

Figure 10:
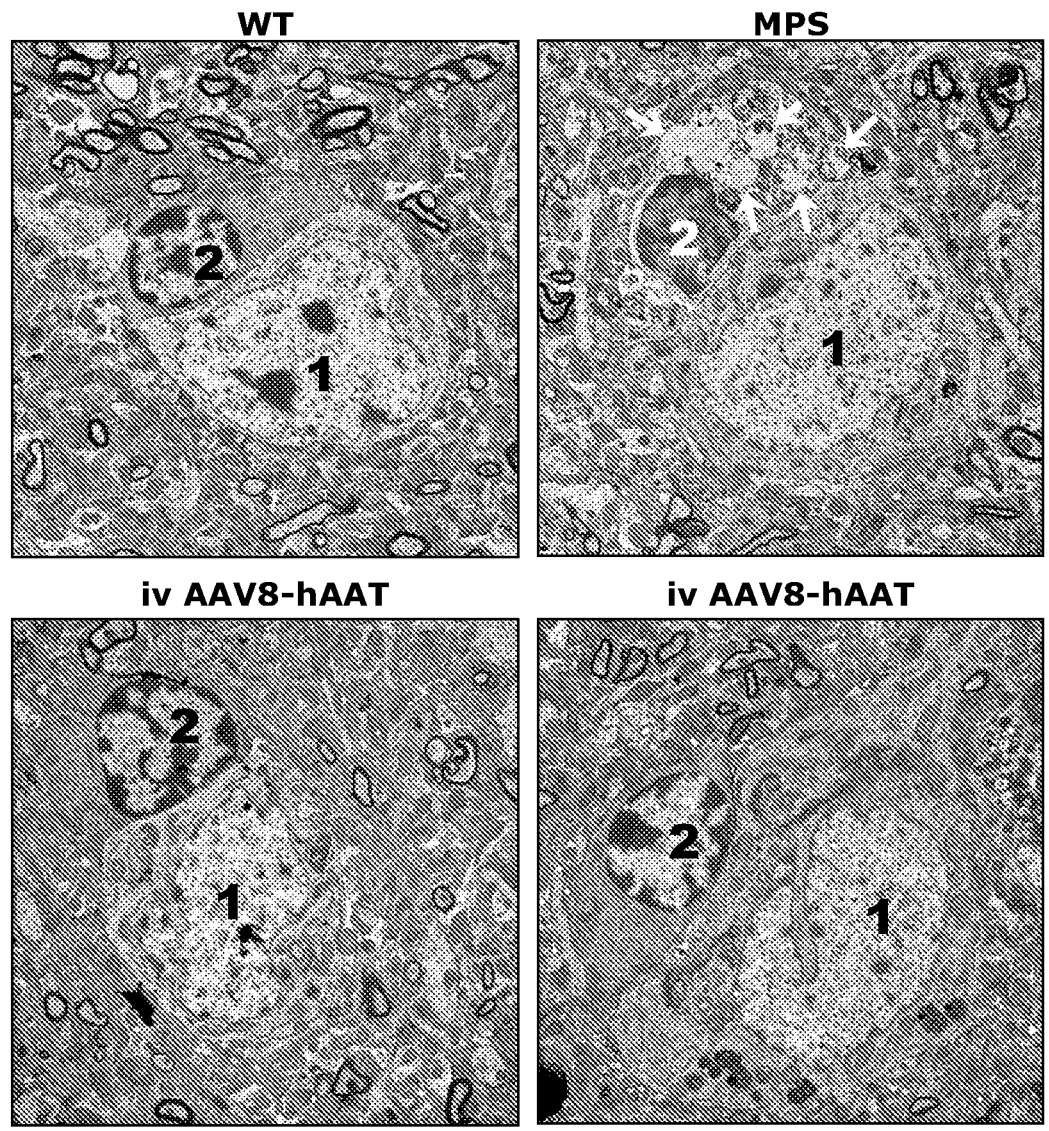
FIG. 10. Reduction of lysosomal pathology in perineuronal glial cells of the occipital cortex. Transmission electron microscopy depicting cortical neurons of the occipital cortex and their associated glial cells. MPSIIIA lysosomal pathology was much more evident in perineuronal glial cells than neurons. The presence of large electro-lucent vacuoles in the glial cells from MPSIIIA untreated male samples (white arrows, upper right panel) and not in WT samples (upper left panel) is shown. This enlargement of the lysosomal compartment was greatly reduced in iv-AAV8hAAT-treated mice, and most of the perineuronal glial cells in these samples presented an aspect similar to that of WTs (bottom panels). (1) neuron, (2) perineuronal glial cell.

The cortex ultrastructure was analyzed by transmission electron microscopy. No distinguishable differences were noted in the ultrastructure of occipital cortical neurons of MPSIIIA treated and untreated subjects. A clear enlargement of the lysosomal compartment was observed in the perineuronal glial cells of the MPSIIIA untreated mice which was practically absent in treated animals. See FIG. 10. These results suggest that sustained high circulating sulfamidase activity prevents neuronal degeneration in MPSIIIA subjects.

Figure 11:
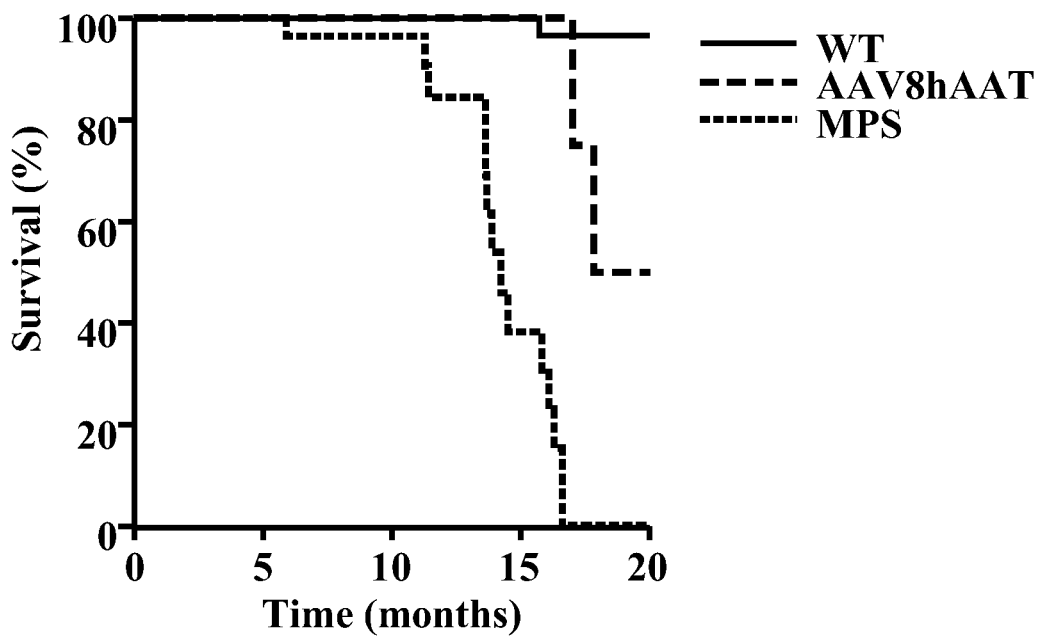
FIG. 11. Survival in intravenous AAV8-hAAT-SFMD treated males and females. (A) Kaplan-Meier survival analysis in WT, MPSIIIA and intravenous AAV8-hAAT-SFMD treated males. Treatment with AAV-mediated liver-directed gene therapy considerably extended the lifespan of MPSIIIA animals (p<0.001). (B) Kaplan-Meier survival analysis in WT, MPSIIIA and iv-AAV8-hAAT-SFMD treated females. Treatment with AAV-mediated liver-directed gene therapy did not extend the lifespan of MPSIIIA females (p=0.467).
Figure 11:
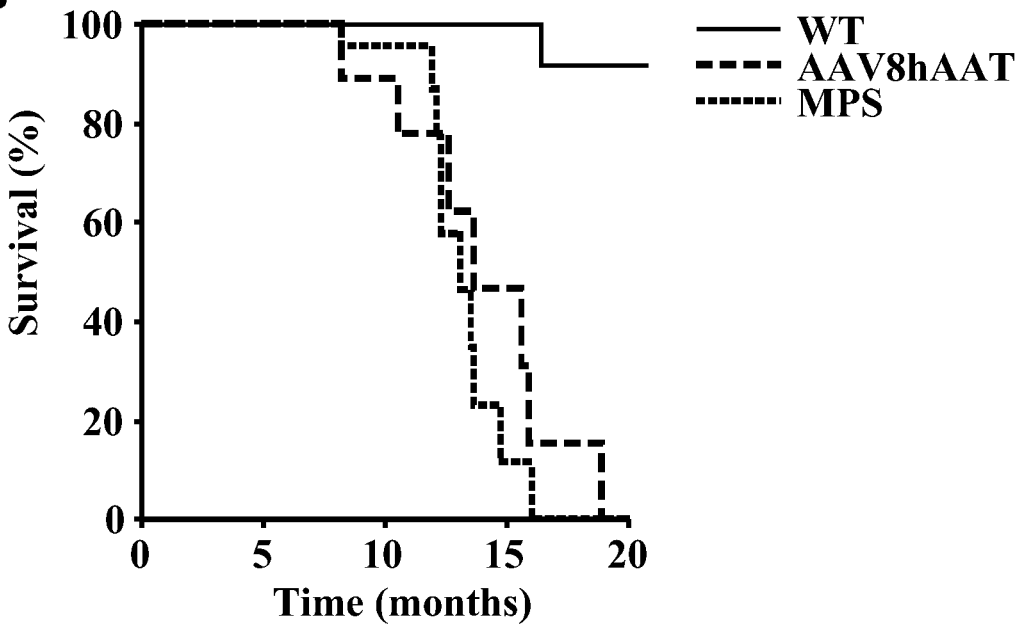

By 17 months of age, all untreated MPSIIIA males had died while 100% of iv-AAV8-hAAT-mu-SFMD treated males were still alive (Median survival=14.2±0.5 vs 18.8±0.9 months for MPSIIIA untreated and treated males respectively, p=0.001) This improvement was not evident in the female group, where both treated and untreated subjects showed similar survival rates (Median survival=13.1±0.5 vs. 13.9±1.2 months for MPSIIIA untreated and treated females, respectively, p=0.467). This result is consistent with the lower levels of sulfamidase activity measured in serum and brain and the lower degree of GAG reduction observed in female animals. See FIG. 11.

The greater survival of iv-AAV8-hAAT-mu-SFMD treated MPSIIIA males further demonstrated the therapeutic potential of sustained supraphysiological levels of circulating sulfamidase obtained through liver-directed gene transfer. Treatment with iv-AAV8-hAAT-mu-SFMD extended the lifespan of MPSIIIA male subjects. See FIG. 11.

Example 5

Intravenous delivery of AAV9-CAG-mu-SFMD

A total dose of $10^{12}$ vector genomes of the AAV9-CAG-mu-SFMD vector was injected into 2-month-old MPSIIIA mice via tail vein.

Figure 6:
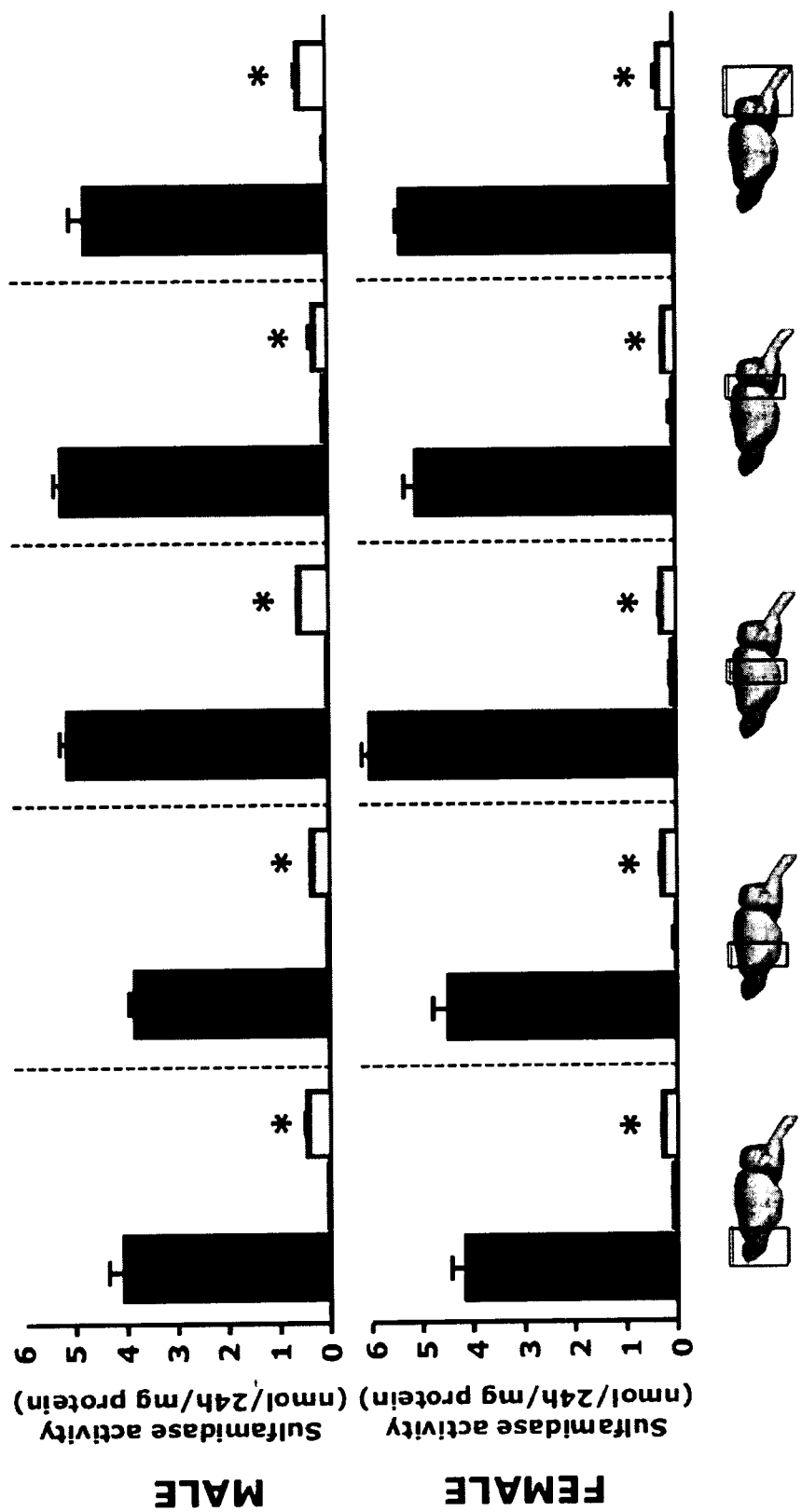
FIG. 6. Intravenous AAV9-CAG-mu-SFMD. (A) Sulfamidase activity in different parts of the brain (depicted in the diagram) of control, MPS and treated mice. (B) Glycosaminoglycan (GAG) quantification in the same parts of the brain. (C) Assessment of motor function by accelerating Rotarod test. Values are means±SEM of 4 to 8 mice per group. ¥P<0.05 vs. control, * P<0.05 vs. untreated MPS.
Figure 6:
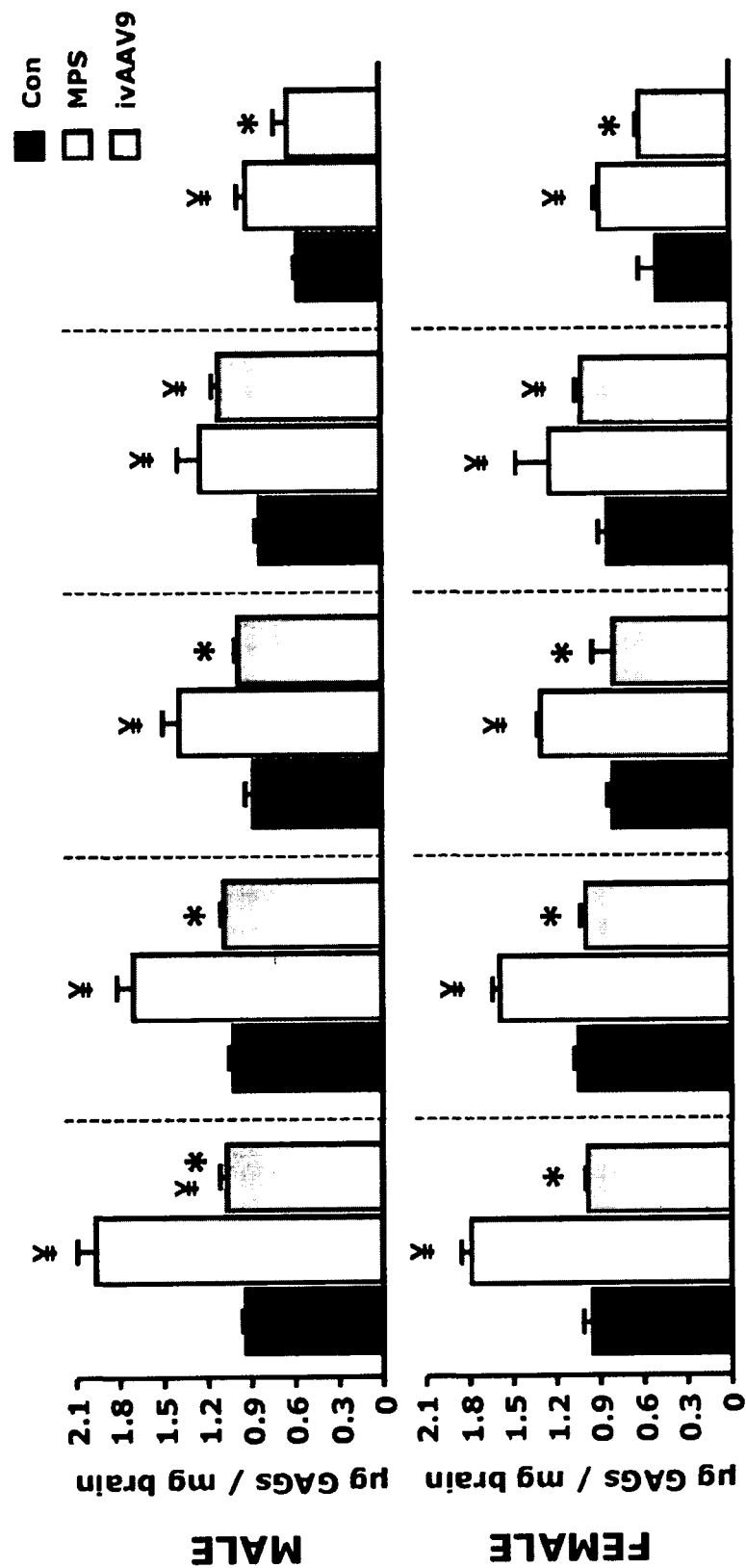
Figure 6:
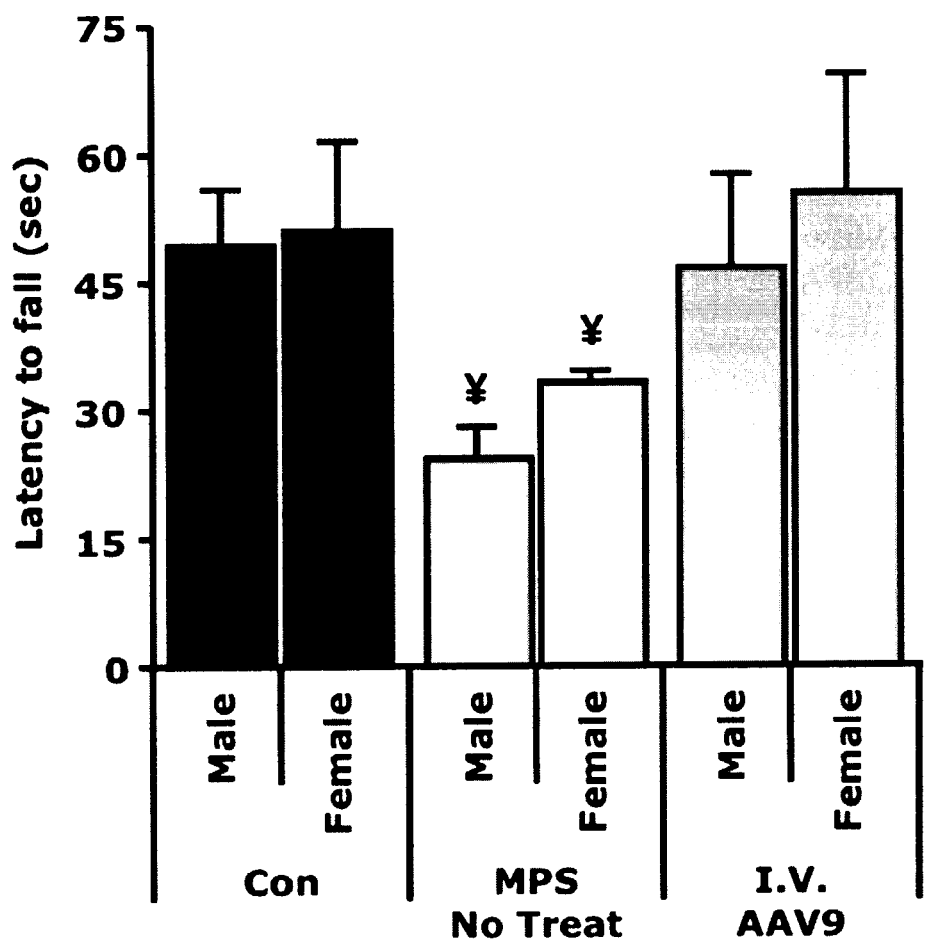

Both treated males and females showed high levels of circulating sulfamidase (500% of control levels in males and 150% in females), which efficiently corrected all somatic tissues in both genders. In addition, given the high efficiency of brain transduction of the AAV serotype 9, significant sulfamidase activity was observed in the brains of both genders, which efficiently corrected GAG storage in all areas of the brain. See FIGS. 6A and 6B. Neuroinflammation (astrogliosis and microgliosis), characteristic of MPSIIIA, was completely normalized in AAV9-treated mice. In addition, AAV9-treated mice performed better in the Rotarod test than untreated animals. See FIG. 6C.

Figure 12:
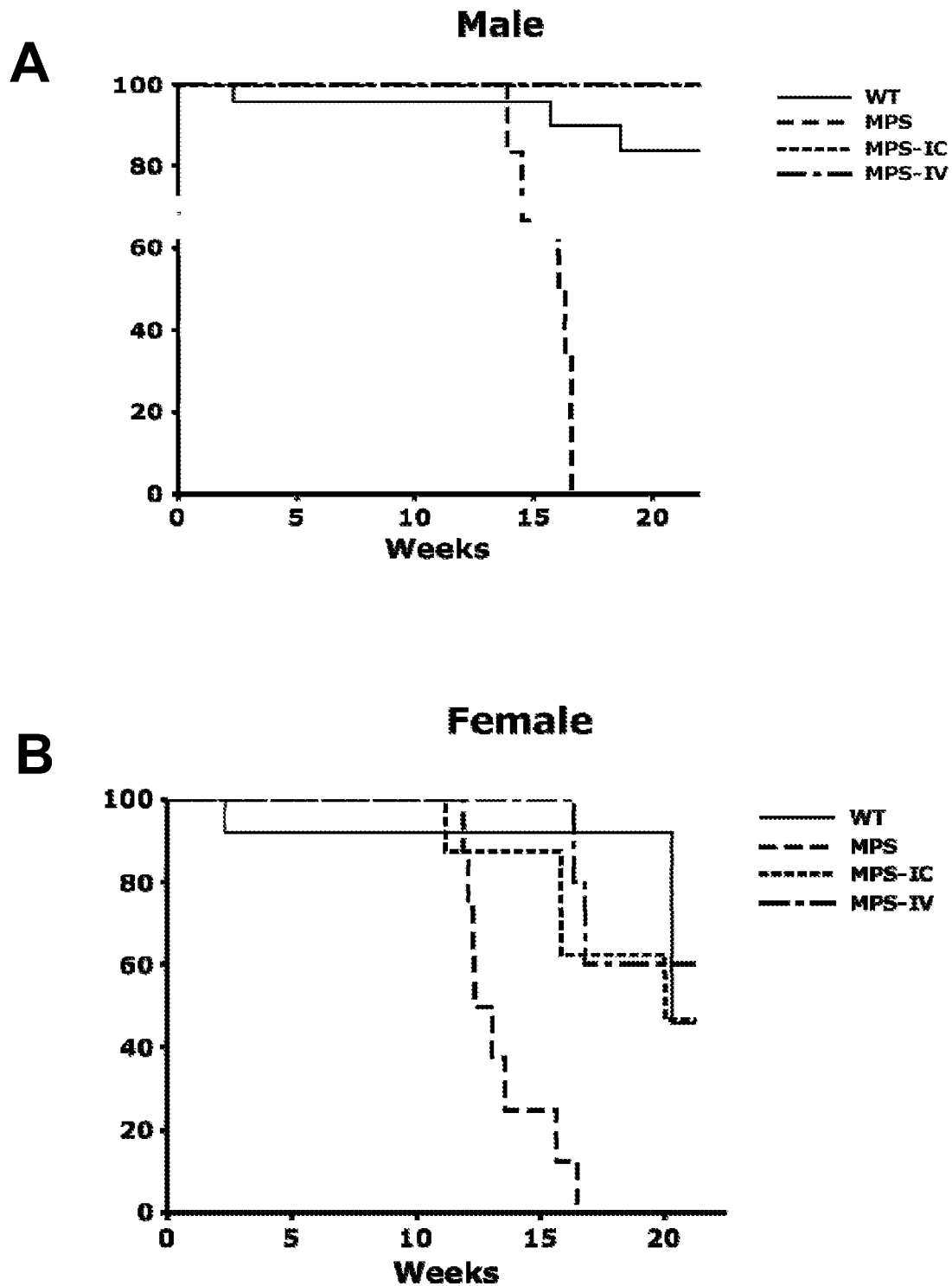
FIG. 12. Survival in intracisternal and intravenous AAV9-CAG-mu-SFMD treated males and females. Kaplan-Meier survival analysis in WT, MPSIIIA and AAV9-treated males (A) and females (B). Both intracisternal and intravenous treatment with AAV-mediated gene therapy extended the lifespan of MPSIIIA animals.

The intravenous treatment with the AAV9-CAG-mu-SFMD vector ("iv-AAV9-CAG-mu-SFMD") extended the lifespan of MPSIIIA animals. See FIG. 12. By 17 months of age, all untreated MPSIIIA males had died while 100% of iv-AAV9-CAG-mu-SFMD treated males were still alive at 20 months of age (p<0.001 and p=0.037 for MPSIIIA treated versus untreated males, respectively). See FIG. 12. The female group showed a similar but less impressive improvement (p=0.063 and p=0.057 for MPSIIIA treated versus untreated females, respectively). This result is consistent with the lower levels of sulfamidase activity measured in serum of female animals after iv-AAV9-CAG-mu-SFMD treatment.

Example 6

Intracisternal Delivery of AAV9-CAG-mu-SFMD

A total dose of $5\times10^{10}$ vector genomes of the AAV9-CAG-mu-SFMD vector was injected into the cisterna magna of 2-month-old anaesthetized MPSIIIA animals in a total volume of 5 μl.

Figure 8:
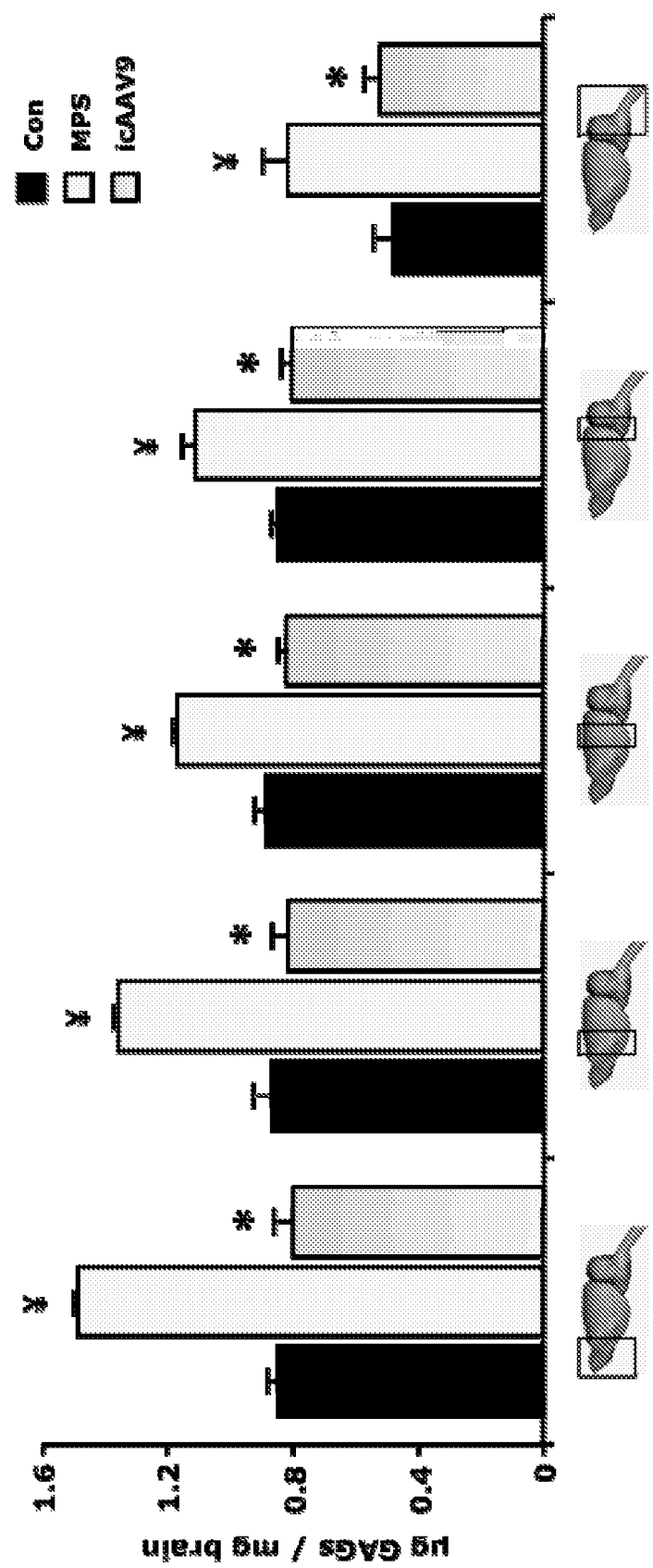
FIG. 8. Intracisternal delivery of AAV9-CAG-mu-SFMD vectors. Glycosaminoglycan (GAG) quantification in different parts of the brain (depicted in the diagram) of control, MPS and treated mice. Values are means±SEM of 3 mice per group. ¥P<0.05 vs. control, * P<0.05 vs. untreated MPS.

Three months after the administration, a complete correction of the GAG accumulation was achieved throughout the entire brain of treated animals. See FIG. 8. Vector-derived sulfamidase expression was also found in the liver of treated animal, suggesting that, after an intracisternal delivery, some vectors reach circulation and are taken up by the liver. In agreement with this result, GAG accumulation was also normalized in the liver.

The intracisternal delivery of the AAV9-CAG-mu-SFMD vector ("ic-AAV9-CAG-mu-SFMD") extended the lifespan of MPSIIIA animals. See FIG. 12. By 17 months of age, all untreated MPSIIIA males had died while 100% of ic-AAV9-CAG-mu-SFMD treated males were still alive at 20 months of age (p<0.001 and p=0.037 for MPSIIIA treated versus untreated males, respectively). See FIG. 12. The female group showed a similar but less impressive improvement (p=0.063 and p=0.057 for MPSIIIA treated versus untreated females, respectively). This result is consistent with the lower levels of sulfamidase activity measured in serum of female animals after ic-AAV9-CAG-mu-SFMD treatment.

Example 7

Intravenous Delivery of AAV9-CAG-co-hu-SFMD (Codon Optimized Human Sulfamidase)

The codon usage of the human sulfamidase was optimized in order to reduce the vector administered dose. The object of this approach was to stabilize the sulfamidase mRNA and increase its translation, thus favoring a higher production of sulfamidase from the same vector dose.

Figure 9:
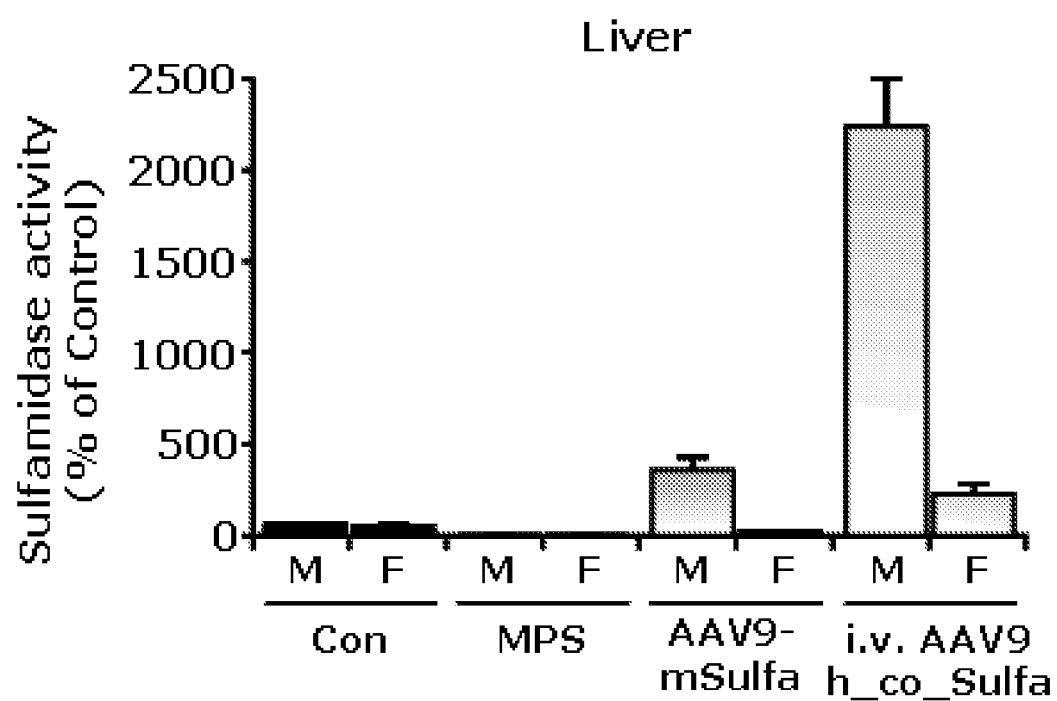
FIG. 9. Intravenous delivery of AAV9-CAG-hu-co-SFMD. Sulfamidase activity in the liver of control mice, MPS mice and mice treated either with AAV9-CAG-mu-SFMD (non-optimized gene) or AAV9-CAG-hu-co-SFMD (optimized gene).

$10^{12}$ viral genomes (vg) of the AAV9-CAG-hu-co-SFMD vector were administered intravenously to 2-month-old MPSIIIA mice via tail vein. At least a 3-fold increase in the sufamidase level in the liver was obtained in comparison with the non-optimized gene. See FIG. 9.

Example 8

Intravenous Delivery of AAV9-hAAT-co-hu-SFMD

Following the same procedure than the one described in example 7, two month-old MPSIIIA mice are treated with $10^{12}$ vg of AAV9-hAAT-co-hu-SFMD vector by intravenous administration into the tail vein. The sulfamidase level is measured in the same way than for example 7. The results show a substantial increase with respect to the non optimized gene.

Example 9

Intracisternal Delivery of Different Serotypes of AAV-CAG-GFP-WPRE

To evaluate the tropism in the brain of the different AAV serotypes when administered into the cerebrospinal fluid, $5\times10^{10}$ vector genomes of AAV1, AAV2, AAV5, AAV7, AAV8 and AAV9 vectors carrying the GFP reporter gene (CAG-GFP-WPRE construct) were administered to MPSIIIA mice intracisternally.

Figure 7:
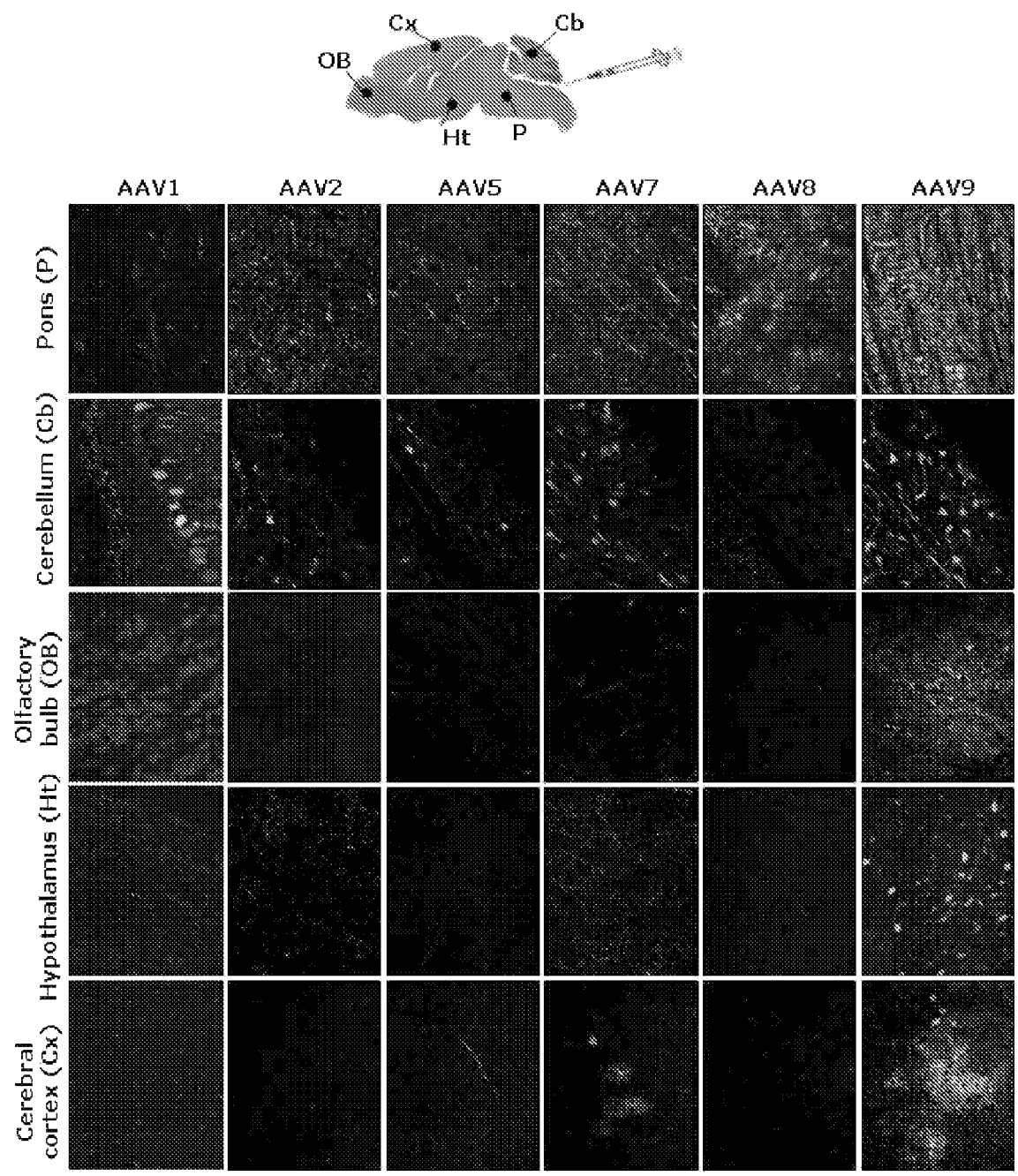
FIG. 7. Brain transduction after intracisternal delivery of adeno-associated virus serotypes 1, 2, 5, 7, 8 and 9 GFP vectors. A dose of $5 \times 10^{10}$ vector genomes of the appropriate vector was administered intracisternally to 2 month old animals, which were sacrificed and analyzed 2 weeks later. Adeno-associated virus serotype 9 demonstrated the highest efficiency of transduction in all analyzed areas. Syringe indicates the route of vector delivery, the cisterna magna. P: Pons, Cb: cerebellum, OB: olfactory bulb, Ht: hypothalamus, Cx: cerebral cortex.

Significant transduction of cells was achieved in the pons by all serotypes, with the highest and lowest efficacies achieved by AAV9 and AAV1, respectively. In the cerebellum, the reporter signal was located mostly in axons identified morphologically as mossy fibers, and especially with AAV1 and AAV9, but also with the other serotypes, except for AAV8, in Purkinje neurons. Greater differences in gene transfer efficiency were observed amongst serotypes in distant brain regions. Many cells were transduced in the cerebral cortex, olfactory bulb and hippocampus in the AAV9-injected group, and to a lesser extent in the AAV7 group, whereas no GFP-positive cell bodies were observed with AAV1, AAV2, AAV5 or AAV8 serotypes in these areas. In the hypothalamus, the AAV9 serotype transduced efficiently neurons, and the AAV1 serotype led to a few scattered GFP+ cells. Occasional GFP-positive axons could be observed throughout the whole brain in all groups, which possibly projected from neurons infected near the cisterna magna. AAV9 vectors showed the highest transduction efficiency among the different serotypes. See FIG. 7.

Example 10

Figure 13:
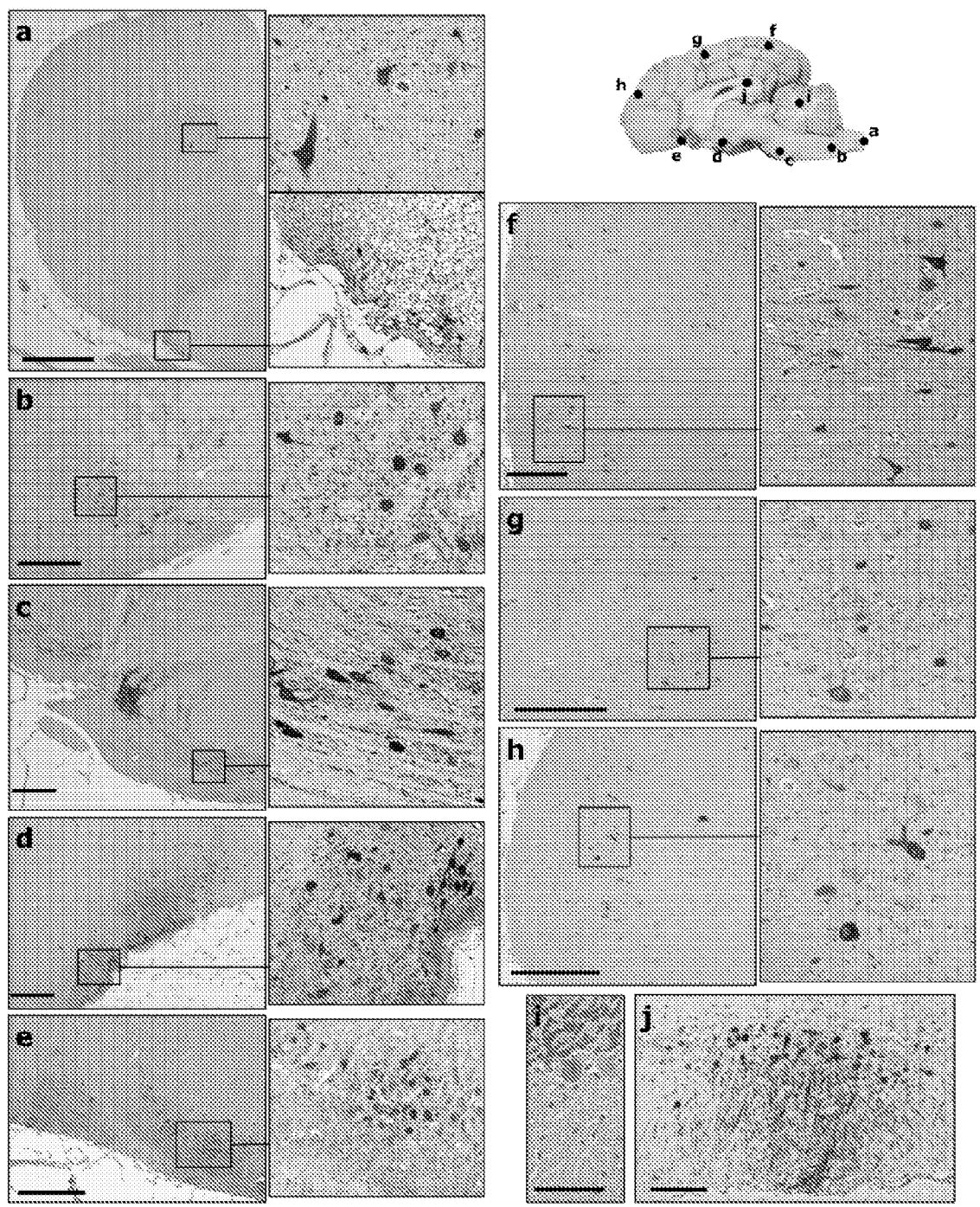
FIG. 13. Intrascisternal administration of AAV9 vectors to dogs leads to transduction of widespread CNS areas and liver. Immunohistochemichal detection of GFP in CNS and liver sections of a dog injected with AAV9-GFP through the cisterna magna. The images correspond to: (a) spinal cord, (b) olivary body of the medulla oblongata, (c) raphe nuclei of the pons, (d) hypothalamic nuclei (e) rhinencephalon (f) occipital cortex, (h) frontal cortex, (i) cerebellum, (j) dentate gyrus of the hippocampus. Scale bar: 1 mm for (a), 500 μm for (b)-(h), 100 μm for (i)-(j).

Scalability of the Intracisternal Delivery of AAV9-CAG-co-hu-SFMD for Clinical use As a first step toward the potential clinical application of AAV9 intracisternal delivery, whether the pattern of transduction observed in mice was maintained in an animal with a more relevant brain size was evaluated. To this end, $1.5 \times 10^{12}$ vg/kg of AAV9-CAG-GFP-WPRE were delivered to the cisterna magna of healthy Beagle dogs. A total of 4 dogs were injected; in two animals (dogs nos. 1 and 4) a pump was used to infuse the viral vector solution at a flux similar to the rate of CFS formation (1 ml/10 minutes), in the other two (dogs nos. 2 and 3) the vector was infused in a few seconds. FIG. 13 shows the immunological detection of GFP in samples from dog 1. A strong labelling was observed in regions close to the cisterna magna, such as the medulla oblongata, the pons and the hypothalamus. See FIGS. 13b, c and d. In the cerebellum, despite being close to the point of injection, only few isolated Purkinje cells were transduced, whereas in the hippocampus, a region far from the cisterna, efficient transduction of the dentate gyrus occurred. See FIG. 13 i and j. The distribution of the virus through the CSF allowed the transduction of areas distant to the point of injection, such as the rhinencephalon and the frontal, parietal and occipital cortex, where more superficial areas showed greater transduction. See FIGS. 13e, h and f. Finally, the vector reached also the spinal cord and GFP signal was detected in ventral motoneurons and astrocytes from the nearby ganglia. See FIG. 13a. The semiquantitative comparison of GFP localization in all four dogs suggested that the rate of infusion of the viral solution did not influence significantly the efficacy or the distribution of the AAV9 vector. See Table 1.

Figure 14:
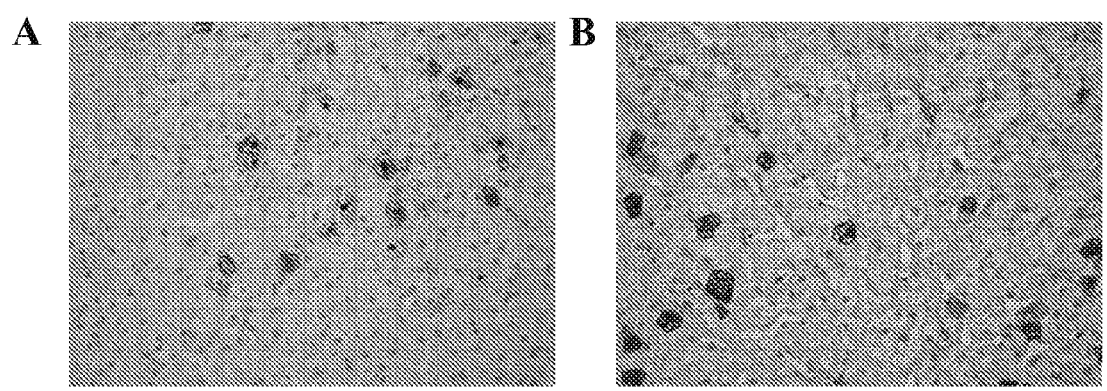
FIG. 14. Liver transduction after intracisternal delivery of AAV9-GFP vector in healthy Beagle dogs. Immunohistochemic detection of GFP in liver sections counterstained with hematoxilin. Representative images of Dog 1 (A) and Dog 2 (B) are shown. Original magnification 200×.

Finally, similar to the observations made in mice after intracisternal delivery of AAV9, GFP was also detected in the liver of Beagle dogs, where an average of 3.7% of hepatocytes was transduced. See FIG. 14. These results suggested systemic distribution of the AAV9 vector after intracisternal delivery.

TABLE 1

Semi-quantitative analysis of brain transduction after ic delivery of AAV9-GFP vectors in healthy beagle dogs. Several pictures of each brain area were counted by three independent observers and the average is represented.

| Brain Area | Dog 1 | Dog 2 | Dog 3 | Dog 4 |
| --- | --- | --- | --- | --- |
| Frontal cortex | +++ | +++ | ++ | +++ |
| Parietal cortex | ++++ | +++ | +++ | +++ |
| Occipital cortex | ++++ | ++++ | ++++ | ++ |
| Hippocampus | ++++ | ++++ | +++ | +++ |
| Hypothalamus | ++++ | N.D. | ++++ | + |
| Cerebelum | + | ++ | ++ | N.D. |
| Brainstem | +++ | +++ | +++ | ++ |
| Medula oblongata | +++ | ++++ | +++ | +++ |
| Spinal cord | +++ | ++ | ++ | N.D. |

The semi-quantitative criteria was the following: (+) less than 10 GFP-positive cells/10X microscopic field; (++) 10-30 GFP-positive cells/10X microscopic field; (+++) 30-60 GFP-positive cells/10X microscopic field and (++++) more than 60 GFP-positive cells/10Xmicroscopic field. N.D. not determined.

Example 11

Functional Efficacy of Codon-Optimized Human Sulfamidase (co-hu-SFMD)

Expression cassettes including a codon optimized version of the human sulfamidase cDNA sequence (co-hu-SFMD) were designed and obtained. Codon optimization was performed to increase the efficiency of SFMD protein production in human beings by utilizing the most abundant tRNAs to the species and by also taking into account its particular translation profile. Mice were utilized for experimental purposes due to their similarity to human beings and the predictive capacity of the mouse animal model.

Figure 15:
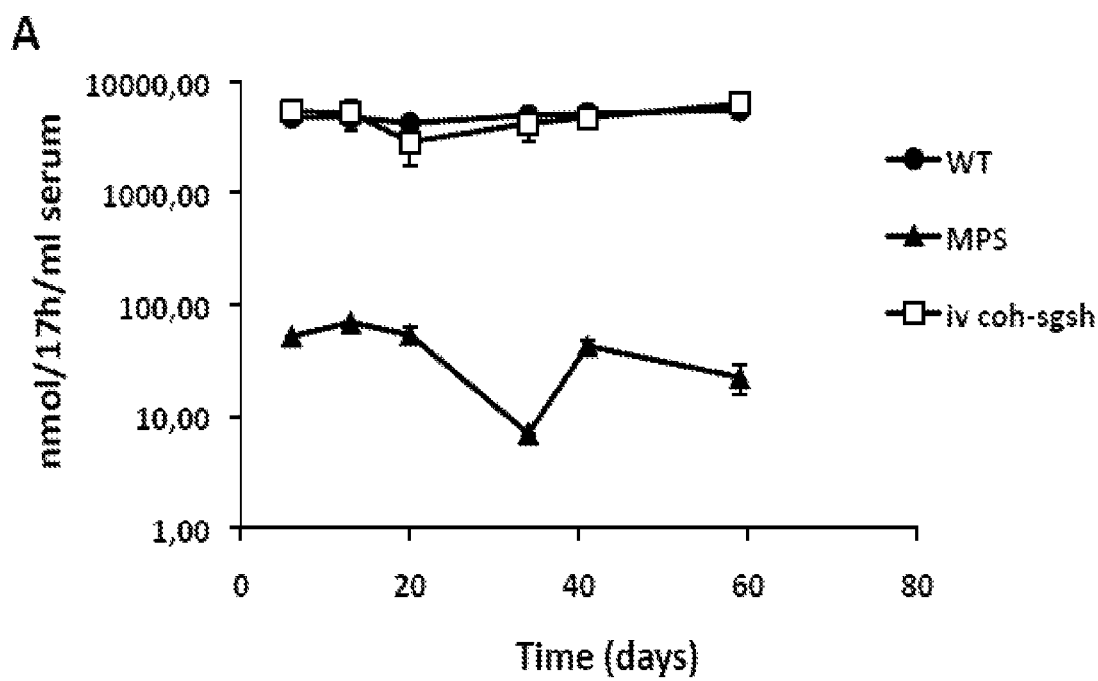
FIG. 15. Serum sulfamidase activity and liver GAG content in intravenous AAV9-co-hu-SFMD injected animals. (A) Sulfamidase activity in the serum measured with a fluorogenic substrate. (B) GAG storage in the liver 2 months after vector administration.
Figure 15:
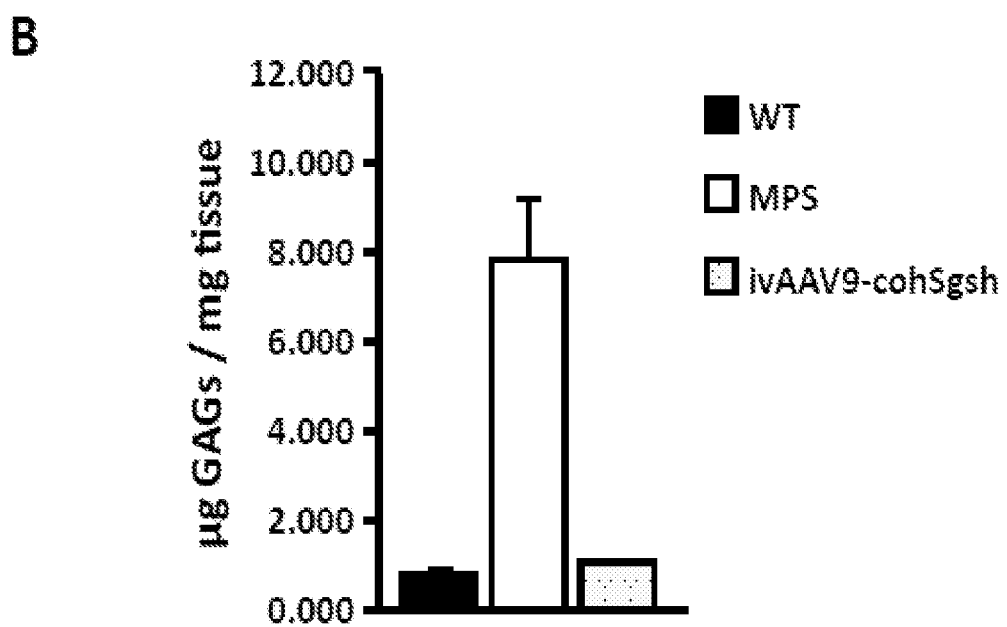

To ensure that this sequence led to the production of active sulfamidase, male MPSIIIA mice were intravenously injected with $1 \times 10^{12}$ vg of an AAV9 vector in which co-hu-SFMD was expressed under the control of the ubiquitous CAG promoter. The activity of sulfamidase in the serum of these mice reached levels similar to that of healthy wild-type animals and was maintained for the duration of the study (2 months). See FIG. 15a. This sustained sulfamidase activity led to the normalization of the GAG content in the livers of these animals, similar to what had been observed with the AAV9-delivered murine transgene. See FIG. 15b.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

The invention claimed is:

1. An isolated nucleotide sequence wherein said sequence is SEQ ID NO: 1.
2. A gene construction comprising the nucleotide sequence according to claim 1.
3. An expression vector comprising the gene construction according to claim 2.
4. The expression vector as defined in claim 3, wherein said vector is an adeno-associated vector.
5. The expression vector according to claim 4, wherein the serotype of die adeno-associated vector is 1, 2, 5, 7, 8 or 9.
6. The expression vector according to claim 5, wherein the serotype is 9.
7. The expression vector according to claim 4, comprising a CAG promoter operably linked to SEQ ID NO: 1.
8. The expression vector according, to claim 7, wherein the expression vector is AAV9-CAG-co-hu-SFMD.
9. A plasmid pAAV-CAG-co-hu-SFMD with accession number DSM 24817, containing the isolated nucleotide sequence according to claim 1.
10. The expression vector according to claim 3 comprising a hAAT promoter operably linked to SEQ ID NO: 1.
11. The expression vector according to claim 10, wherein the expression vector is an adeno-associated virus serotype 9 (AAV9) comprising the codon optimized human sulfamidase gene (co-hu-SFMD) of SEQ ID NO: 1 operably linked to a human alpha1-antitrypsin promoter (hAAT) known as AAV9-hAAT-co-hu-SFMD.

12. A plasmid pAAV-hAAT-co-hu-SFMD comprising the codon optimized human sulfamidase gene (co-hu-SFMD) of SEQ ID NO: 1 according to claim 1 operably linked to a human alpha1-antitrypsin promoter (hAAT).

13. A pharmaceutical composition comprising the nucleotide sequence according to claim 1.

14. A pharmaceutical composition comprising the gene construction according to claim 2.

15. A pharmaceutical composition comprising the expression vector according to claim 3.

16. A method for increasing the sulfamidase activity in the body comprising administering to a subject in need thereof the Pharmaceutical composition according to claim 13, 14, or 15.

17. A method for the treatment of mucopolysaccharidoses comprising administering to a subject having mucopolysaccharidoses the pharmaceutical composition according to claim 13, 14, or 15.

18. A method of producing the expression vectors according to claim 4 comprising the steps of:
   i) providing a first vector comprising SEQ ID NO: 1 interposed between a first AAV terminal repeat and a second AAV terminal repeat, a CAG or hAAT promoter operably linked to SEQ ID NO: 1; a second vector comprising an AAV rep gene and an AAV cap gene; and a third vector comprising an adenovirus helper function;
   ii) co-transfecting competent cells with the vectors of step i);
   iii) culturing the transfected cells of step ii); and
   iv) purifying the expression vectors from the culture of step iii).

19. An isolated cell transfected with the nucleotide sequence according to claim 1.

20. An isolated cell transfected with the gene construction according to claim 2.

21. An isolated cell transfected with the expression vector according to claim 3.

* * * * *

SEQUENCE LISTING

<160> NUMBER OF SEQ ID NOS: 11

<210> SEQ ID NO 1
<211> LENGTH: 1515
<212> TYPE: DNA
<213> ORGANISM: artificial sequence
<220> FEATURE:
<223> OTHER INFORMATION: codon-optimized sequence of human sulfamidase

<400> SEQUENCE: 1

```
gccaccatga gctgccctgt gcccgcctgt tgtgccctgc tgctggtgct gggactgtgc      60
agagccagac cccggaacgc tctgctgctg ctggccgacg atggcggatt tgagagcggc     120
gcctacaaca cagcgccat tgccacccct catctggacg ccctggccag aagaagcctg     180
ctgttccgga acgccttcac cagcgtgtcc agctgcagcc tagcagagc ttccctgctg     240
acaggcctgc cccagcatca gaatggcatg tacggcctgc accaggatgt gcatcacttc     300
aacagcttcg acaaagtgcg gagcctgcca ctgctcctgt cacaggctgg cgtgagaacc     360
ggcatcatcg gcaagaaaca cgtgggcccc gagacagtgt accccttcga cttcgcctac     420
accgaagaga cggcagcgt gctgcaggtc ggccggaaca tcacccggat caagctgctc     480
gtgcggaagt ttctccagac ccaggacgac cggcccttct tcctgtacgt ggccttccac     540
gaccctcaca gatgcggcca cagccagccc cagtacggca ccttctgcga agttcggc       600
aacggcgaga gcggcatggg cagaatcccc gactggaccc ccaggcata cgaccctctg     660
gacgtgctgg tgccctactt cgtgcccaac accctgccg ccagagctga tctggccgcc     720
cagtacacca ccgtgggcag aatggatcag ggcgtgggcc tggtgctgca ggaactgagg     780
gacgctggcg tgctgaacga caccctggtc atcttcacct ccgacaacgg catcccattc     840
cccagcggcc ggaccaatct gtactggccc ggcacagccg aacctctgct ggtgtccagc     900
cccgagcacc ctaagagatg gggccaggtg tccgaggcct acgtgtccct gctggacctg     960
acccccacca tcctggactg gttcagcatc ccctacccca gctacgccat ctttggaagc    1020
aagaccatcc acctgaccgg cagatctctg ctgcctgccc tggaagctga gcctctgtgg    1080
gccaccgtgt cggcagcca gagccaccac gaagtgacca tgagctaccc catgcggagc    1140
gtgcagcacc ggcacttccg gctggtgcac aacctgaact tcaagatgcc cttcccaatc    1200
gaccaggact tttacgtgtc ccccaccttc caggacctgc tgaacagaac cacagccggc    1260
cagcccaccg ctggtacaa ggacctgcgg cactactact accgggccag atgggagctg    1320
tacgacagaa gccgggaccc ccacgagaca cagaacctgg ccaccgaccc cagattcgcc    1380
cagctcctgg aaatgctgcg ggaccagctg gccaagtggc agtgggagac acacgacct    1440
tgggtctgcg ctcccgacgg cgtgctggaa gagaagctgt ccccccagtg ccagccactg    1500
cacaacgagc tgtga                                                    1515
```

<210> SEQ ID NO 2
<211> LENGTH: 502
<212> TYPE: PRT
<213> ORGANISM: Homo sapiens

<400> SEQUENCE: 2

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
```

```
               35                  40                  45
His Leu Asp Ala Leu Ala Arg Arg Ser Leu Leu Phe Arg Asn Ala Phe
 50                  55                  60

Thr Ser Val Ser Ser Cys Ser Pro Ser Arg Ala Ser Leu Leu Thr Gly
 65                  70                  75                  80

Leu Pro Gln His Gln Asn Gly Met Tyr Gly Leu His Gln Asp Val His
                 85                  90                  95

His Phe Asn Ser Phe Asp Lys Val Arg Ser Leu Pro Leu Leu Leu Ser
                100                 105                 110

Gln Ala Gly Val Arg Thr Gly Ile Ile Gly Lys Lys His Val Gly Pro
                115                 120                 125

Glu Thr Val Tyr Pro Phe Asp Phe Ala Tyr Thr Glu Glu Asn Gly Ser
                130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
                180                 185                 190

Phe Cys Glu Lys Phe Gly Asn Gly Glu Ser Gly Met Gly Arg Ile Pro
                195                 200                 205

Asp Trp Thr Pro Gln Ala Tyr Asp Pro Leu Asp Val Leu Val Pro Tyr
                210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                    245                 250                 255

Leu Arg Asp Ala Gly Val Leu Asn Asp Thr Leu Val Ile Phe Thr Ser
                260                 265                 270

Asp Asn Gly Ile Pro Phe Pro Ser Gly Arg Thr Asn Leu Tyr Trp Pro
                275                 280                 285

Gly Thr Ala Glu Pro Leu Leu Val Ser Ser Pro Glu His Pro Lys Arg
                290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                    325                 330                 335

Gly Ser Lys Thr Ile His Leu Thr Gly Arg Ser Leu Leu Pro Ala Leu
                340                 345                 350

Glu Ala Glu Pro Leu Trp Ala Thr Val Phe Gly Ser Gln Ser His His
                355                 360                 365

Glu Val Thr Met Ser Tyr Pro Met Arg Ser Val Gln His Arg His Phe
                370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                    405                 410                 415

Ala Gly Gln Pro Thr Gly Trp Tyr Lys Asp Leu Arg His Tyr Tyr Tyr
                420                 425                 430

Arg Ala Arg Trp Glu Leu Tyr Asp Arg Ser Asp Pro His Glu Thr
                435                 440                 445

Gln Asn Leu Ala Thr Asp Pro Arg Phe Ala Gln Leu Leu Glu Met Leu
                450                 455                 460
```

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 3
<211> LENGTH: 1726
<212> TYPE: DNA
<213> ORGANISM: Artificial Sequence
<220> FEATURE:
<223> OTHER INFORMATION: CAG Promoter.

<400> SEQUENCE: 3

| | | | | | |
|---|---|---|---|---|---|
| tcgacattga | ttattgacta | gttattaata | gtaatcaatt | acggggtcat | tagttcatag | 60 |
| cccatatatg | gagttccgcg | ttacataact | tacggtaaat | ggcccgcctg | gctgaccgcc | 120 |
| caacgacccc | cgcccattga | cgtcaataat | gacgtatgtt | cccatagtaa | cgccaatagg | 180 |
| gactttccat | tgacgtcaat | gggtggagta | tttacggtaa | actgcccact | tggcagtaca | 240 |
| tcaagtgtat | catatgccaa | gtacgccccc | tattgacgtc | aatgacggta | aatggcccgc | 300 |
| ctggcattat | gcccagtaca | tgaccttatg | ggactttcct | acttggcagt | acatctacgt | 360 |
| attagtcatc | gctattacca | tggtcgaggt | gagccccacg | ttctgcttca | ctctccccat | 420 |
| ctccccccc | tccccacccc | caattttgta | tttatttatt | ttttaattat | tttgtgcagc | 480 |
| gatggggcg | gggggggggg | ggggcgcgc | gccaggcggg | gcgggcggg | gcgagggcg | 540 |
| gggcggggcg | aggcggagag | gtgcggcggc | agccaatcag | agcggcgcgc | tccgaaagtt | 600 |
| tccttttatg | gcgaggcggc | ggcggcggcg | gccctataaa | aagcgaagcg | cgcggcgggc | 660 |
| gggagtcgct | gcgttgcctt | cgccccgtgc | cccgctccgc | cgcgctcgc | ccgcccgcc | 720 |
| ccggctctga | ctgaccgcgt | tactcccaca | ggtgagcggg | cgggacgcc | cttctcctcc | 780 |
| gggctgtaat | tagcgcttgg | tttaatgacg | gcttgtttct | tttctgtggc | tgcgtgaaag | 840 |
| ccttgagggg | ctccgggagg | gccctttgtg | cgggggagc | ggctcggggg | gtgcgtgcgt | 900 |
| gtgtgtgtgc | gtgggagcg | ccgcgtgcgg | ctccgcgctg | cccggcggct | gtgagcgctg | 960 |
| cgggcgcggc | gcgggctttt | gtgcgctccg | cagtgtgcgc | gaggggagcg | cggccggggg | 1020 |
| cggtgccccg | cggtgcgggg | ggctgcgagg | ggaacaaagg | ctgcgtgcgg | ggtgtgtgcg | 1080 |
| tggggggggtg | agcaggggt | gtgggcgcgt | cggtcgggct | gcaacccccc | ctgcacccc | 1140 |
| ctccccgagt | tgctgagcac | ggcccggctt | cgggtgcggg | gctccgtacg | gggcgtggcg | 1200 |
| cggggctcgc | cgtgccgggc | gggggtggc | ggcaggtggg | ggtgccggc | ggggcggggc | 1260 |
| cgcctcgggc | cgggagggc | tcgggggagg | ggcgcggcgg | ccccggagc | gccggcggct | 1320 |
| gtcgaggcgc | ggcgagccgc | agccattgcc | ttttatggta | atcgtgcgag | agggcgcagg | 1380 |
| gacttccttt | gtcccaaatc | tgtgcggagc | cgaaatctgg | gaggcgccgc | cgcaccccct | 1440 |
| ctagcgggcg | cggggcgaag | cggtgcggcg | ccggcaggaa | ggaaatgggc | ggggagggcc | 1500 |
| ttcgtgcgtc | gccgcgccgc | cgtccccttc | tccctctcca | gcctcggggc | tgtccgcggg | 1560 |
| gggacggctg | ccttcggggg | ggacggggca | gggcggggtt | cggcttctgg | cgtgtgaccg | 1620 |
| gcggctctag | agcctctgct | aaccatgttc | atgccttctt | cttttttccta | cagctcctgg | 1680 |
| gcaacgtgct | ggttattgtg | ctgtctcatc | atttttggcaa | agaatt | 1726 |

```
<210> SEQ ID NO 4
<211> LENGTH: 981
<212> TYPE: DNA
<213> ORGANISM: Artificial Sequence
<220> FEATURE:
<223> OTHER INFORMATION: Liver-specific human alpha1-antitrypsin
      Promoter.

<400> SEQUENCE: 4
cagagaggtc tctgacctct gccccagctc caaggtcagc aggcagggag ggctgtgtgt      60
ttgctgtttg ctgcttgcaa tgtttgccca ttttagggac atgagtaggc tgaagtttgt     120
tcagtgtgga cttcagaggc agcacacaaa cagcaagctt gcgaattcca gtctacagag     180
aggtctctga cctctgcccc agctccaagg tcagcaggca gggagggctg tgtgtttgct     240
gtttgctgct tgcaatgttt gcccatttta gggacatgag taggctgaag tttgttcagt     300
gtggacttca gaggcagcac acaaacagca agcttgcgaa ttccagtcta cagagaggtc     360
tctgacctct gccccagctc caaggtcagc aggcagggag gctgtgtgt ttgctgtttg     420 ctgcttgcaa tgtttgccca ttttagggac atgagtaggc tgaagtttgt tcagtgtgga     480
cttcagaggc agcacacaaa cagcaagctt tgctctagac tggaattcgt cgacgagctc     540
cctatagtga gtcgtattag aggccgactg acccggtacc cggggatctt gctaccagtg     600
gaacagccac taaggattct gcagtgagag cagagggcca gctaagtggt actctcccag     660
agactgtctg actcacgcca ccccctccac cttggacaca ggacgctgtg gtttctgagc     720
caggtacaat gactcctttc ggtaagtgca gtggaagctg tacactgccc aggcaaagcg     780
tccgggcagc gtaggcgggc gactcagatc ccagccagtg gacttagccc ctgtttgctc     840
ctccgataac tggggtgacc ttggttaata ttcaccagca gcctccccg ttgcccctct     900 ggatccactg cttaaatacg gacgaggaca gggccctgtc tcctcagctt caggcaccac     960
cactgacctg ggacagtgaa t                                              981

<210> SEQ ID NO 5
<211> LENGTH: 34
<212> TYPE: DNA
<213> ORGANISM: Mus musculus

<400> SEQUENCE: 5
cttacttatg acgcgtatgc actgcccggg actg                                  34

<210> SEQ ID NO 6
<211> LENGTH: 39
<212> TYPE: DNA
<213> ORGANISM: Mus musculus

<400> SEQUENCE: 6
tatcctatcg acgcgttcag agttcattgt gaagcggtc                             39

<210> SEQ ID NO 7
<211> LENGTH: 8445
<212> TYPE: DNA
<213> ORGANISM: Artificial Sequence
<220> FEATURE:
<223> OTHER INFORMATION: pAAV-CAG-mu-SFMD-WPRE.
<220> FEATURE:
<221> NAME/KEY: misc_feature
<222> LOCATION: (3466)..(3470)
<223> OTHER INFORMATION: n is a, c, g, or t

<400> SEQUENCE: 7
atgcagctgc gcgctcgctc gctcactgag gcccagctgc gcgctcgctc gctcactgag      60
```

| | |
|---|---|
| gccgcccggg caaagcccgg gcgtcgggcg acctttggtc gcccggcctc agtgagcgag | 120 |
| cgagcgcgca gagagggagt ggccaactcc atcactaggg gttccttgta gttaatgatt | 180 |
| aacccgccat gctacttatc tactcgacat tgattattga ctagttatta atagtaatca | 240 |
| attacggggt cattagttca tagcccatat atggagttcc gcgttacata acttacggta | 300 |
| aatggcccgc ctggctgacc gcccaacgac ccccgcccat tgacgtcaat aatgacgtat | 360 |
| gttcccatag taacgccaat agggactttc cattgacgtc aatgggtgga gtatttacgg | 420 |
| taaactgccc acttggcagt acatcaagtg tatcatatgc caagtacgcc ccctattgac | 480 |
| gtcaatgacg gtaaatggcc cgcctggcat tatgcccagt acatgacctt atgggacttt | 540 |
| cctacttggc agtacatcta cgtattagtc atcgctatta ccatggtcga ggtgagcccc | 600 |
| acgttctgct tcactctccc catctccccc cctccccac ccccaattttt gtatttattt | 660 |
| attttttaat tattttgtgc agcgatgggg gcggggggg ggggggggcg cgcgccaggc | 720 |
| ggggcgggc ggggcgaggg gcggggcggg gcgaggcgga gaggtgcggc ggcagccaat | 780 |
| cagagcggcg cgctccgaaa gtttcctttt atggcgaggc ggcggcggcg gcggccctat | 840 |
| aaaaagcgaa gcgcgcggcg gcgggagtc gctgcgttgc cttcgccccg tgccccgctc | 900 |
| cgcgccgcct cgcgccgccc gccccggctc tgactgaccg cgttactccc acaggtgagc | 960 |
| gggcgggacg gcccttctcc tccgggctgt aattagcgct tggtttaatg acggcttgtt | 1020 |
| tcttttctgt ggctgcgtga aagccttgag gggctccggg agggccctt gtgcgggggg | 1080 |
| agcggctcgg ggggtgcgtg cgtgtgtgtg tgcgtgggga gcgccgcgtg cggctccgcg | 1140 |
| ctgcccggcg gctgtgagcg ctgcgggcgc ggcgcggggc tttgtgcgct ccgcagtgtg | 1200 |
| cgcgagggga gcgcggccgg gggcggtgcc ccgcggtgcg gggggctgcg aggggaacaa | 1260 |
| aggctgcgtg cggggtgtgt gcgtgggggg gtgagcaggg ggtgtgggcg cgtcggtcgg | 1320 |
| gctgcaaccc cccctgcacc cccctccccg agttgctgag cacgccgg cttcgggtgc | 1380 |
| ggggctccgt acgggcgtg gcgcggggct cgccgtgccg gcgggggt ggcggcaggt | 1440 |
| ggggtgccg ggcggggcgg ggccgcctcg ggccggggag ggctcggggg aggggcgcgg | 1500 |
| cggcccccgg agcgccggcg gctgtcgagg gcgggcgagc cgcagccatt gccttttatg | 1560 |
| gtaatcgtgc gagagggcgc agggacttcc tttgtcccaa atctgtgcgg agccgaaatc | 1620 |
| tgggaggcgc cgccgcaccc cctctagcgg gcgcgggggcg aagcggtgcg cgcgccggcag | 1680 |
| gaaggaaatg ggcggggagg gccttcgtgc gtcgccgcgc cgccgtcccc ttctccctct | 1740 |
| ccagcctcgg ggctgtccgc gggggacgg ctgccttcgg ggggacggg gcagggcggg | 1800 |
| gttcggcttc tggcgtgtga ccggcggctc tagagcctct gctaaccatg ttcatgcctt | 1860 |
| cttcttttc ctacagctcc tgggcaacgt gctggttatt gtgctgtctc atcattttgg | 1920 |
| caaagaattg attaattcga gcgaacgcgt atgcactgcc cggggactggc ctgctgcaca | 1980 |
| attctgttgg tcctgggact ctgcggcgcg cactcgcgca acgtgctact gatagttgcg | 2040 |
| gatgacggag gctttgagag tggtgtatac aacaacactg ccatcgccac ccctcacctg | 2100 |
| gatgccctgt cccgccacag ccttatcttc cgtaacgcct tcacgtctgt cagcagctgt | 2160 |
| tccccgagcc gtgccagcct cctcaccggc ctgcccagc atcagaatgg catgtatggg | 2220 |
| ctgcaccagg atgtgcatca cttcaactct tttgacaagg tacagagcct tccgctgctg | 2280 |
| ctcaaccagg ccggagtgcg cacaggcatc attgggaaga agcacgtggg tccggagacg | 2340 |
| gtgtatccct ttgactttgc attcacagag gagaacagct ctgtgatgca ggtggggcgg | 2400 |

```
aacatcacta gaattaagca actggtccag aaatttctgc agactcagga tgacaggccc    2460
ttcttcctgt acgtggcttt ccatgacccg caccgctgtg ggcactctca gccccagtat    2520
ggaaccttct gtgagaagtt tggcaacgga gagagtggaa tggggtacat tccagactgg    2580
acacccccaga tctacgaccc tcaggatgtg atggtgccct actttgtccc ggacacacca    2640
gcagcccgag cagacctagc tgctcagtac accaccatcg ggcggatgga ccaaggggta    2700
ggtctggtgc tccaggagct gcgaggtgct ggtgtgctga cgacaccct catcatcttc    2760
acatctgaca atggtatccc tttcccagc ggcaggacca acctgtactg gcccggtaca    2820
gccgagcctt tgctggtgtc atctccagag cacccacagc gctggggcca ggtcagcgac    2880
gcctacgtga gccttctaga cctcacccct accatcctgg actggttctc catcccgtac    2940
cccagctatg ccatctttgg ctcaaagacg atccagctca caggccgatc cctcctgccg    3000
gcgctggagg cagagcccct ttgggccact gtcttcagca gccagagcca ccacgaggtc    3060
accatgtcct acccgatgcg ctcggtgtac caccagaact tccgcctcat tcacaacctg    3120
agcttcaaga tgccatttcc catcgaccaa gatttctatg tctcgccgac cttccaggac    3180
ctcctgaacc gaaccaccac aggccggccc acgggctggt acaaggacct ccaccgttac    3240
tactaccggg aacgctggga actctacgac atcagccggg accctcgaga gacacggaac    3300
ctggccgctg acccagactt ggctcaagtg ctggagatgc tgaaagctca gcttgtcaag    3360
tggcaatggg agacacatga cccctgggtg tgcgccccag atggagtcct ggaggaaaag    3420
ctcacacccc agtgccgacc gcttcacaat gaactctgaa cgcgtnnnnn gctagctcga    3480
tatcggccta ggctggatcc gcgcggccgc aagaattccc gataatcaac ctctggatta    3540
caaaatttgt gaaagattga ctggtattct taactatgtt gctccttttta cgctatgtgg    3600
atacgctgct ttaatgcctt tgtatcatgc tattgcttcc cgtatggctt tcattttctc    3660
ctccttgtat aaatcctggt tgctgtctct ttatgaggag ttgtggcccg ttgtcaggca    3720
acgtggcgtg gtgtgcactg tgtttgctga cgcaaccccc actggttggg gcattgccac    3780
cacctgtcag ctcctttccg ggactttcgc tttccccctc cctattgcca cggcggaact    3840
catcgccgcc tgccttgccc gctgctggac agggggtcgg ctgttgggca ctgacaattc    3900
cgtggtgttg tcggggaagc tgacgtcctt tccatggctg ctcgcctgtg ttgccacctg    3960
gattctgcgc gggacgtcct tctgctacgt cccttcggcc ctcaatccag cggaccttcc    4020
ttcccgcggc ctgctgccgg ctctgcggcc tcttccgcgt cttcgccttc gccctcagac    4080
gagtcggatc tcccctttggg ccgcctcccc gcatcgggaa ttcgagctcg tacccggga    4140
atcaattcac tcctcaggtg caggctgcct atcagaaggt ggtggctggt gtggccaatg    4200
ccctggctca caataccac tgagatcttt ttccctctgc caaaaattat ggggacatca    4260
tgaagcccct tgagcatctg acttctggct aataaaggaa atttattttc attgcaatag    4320
tgtgttggaa ttttttgtgt ctctcactcg gaaggacata tgggagggca aatcatttaa    4380
aacatcagaa tgagtatttg gtttagagtt tggcaacata tgcccatatg ctggctgcca    4440
tgaacaaagg ttggctataa agaggtcatc agtatatgaa acagccccct gctgtccatt    4500
ccttattcca tagaaaagcc ttgacttgag gttagatttt ttttatattt tgttttgtgt    4560
tattttttc tttaacatcc ctaaaatttt ccttacatgt tttactagcc agattttcc    4620
tcctctcctg actactccca gtcatagctg tccctcttct cttatggaga tccctcgacc    4680
tgcagcccaa gctgtagata agtagcatgg cgggttaatc attaactaca aggaacccct    4740
agtgatggag ttggccactc cctctctgcg cgctcgctcg ctcactgagg ccgggcgacc    4800
```

```
aaaggtcgcc cgacgcccgg gctttgcccg ggcggcctca gtgagcgagc gagcgcgcag   4860
ctggcgtaat agcgaagagg cccgcaccga tcgcccttcc caacagttgc gcagcctgaa   4920
tggcgaatgg cgattccgtt gcaatggctg gcggtaatat tgttctggat attaccagca   4980
aggccgatag tttgagttct tctactcagg caagtgatgt tattactaat caagaagta    5040 ttgcgacaac ggttaatttg cgtgatggac agactctttt actcggtggc ctcactgatt   5100
ataaaaacac ttctcaggat tctggcgtac cgttcctgtc taaaatccct ttaatcggcc   5160
tcctgtttag ctcccgctct gattctaacg aggaaagcac gttatacgtg ctcgtcaaag   5220
caaccatagt acgcgccctg tagcggcgca ttaagcgcgg cgggtgtggt ggttacgcgc   5280
agcgtgaccg ctacacttgc cagcgcccta gcgcccgctc ctttcgcttt cttcccttcc   5340
tttctcgcca cgttcgccgg ctttccccgt caagctctaa atcgggggct ccctttaggg   5400
ttccgattta gtgctttacg gcacctcgac cccaaaaaac ttgattaggg tgatggttca   5460
cgtagtgggc catcgccctg atagacggtt tttcgccctt tgacgttgga gtccacgttc   5520
tttaatagtg actcttgtt ccaaactgga acaacactca accctatctc ggtctattct    5580
tttgatttat aagggatttt gccgatttcg gcctattggt taaaaaatga gctgatttaa   5640
caaaaattta acgcgaattt taacaaaata ttaacgctta caatttaaat atttgcttat   5700
acaatcttcc tgttttggg gcttttctga ttatcaaccg ggtacatat gattgacatg     5760 ctagttttac gattaccgtt catcgattct cttgtttgct ccagactctc aggcaatgac   5820
ctgatagcct ttgtagagac ctctcaaaaa tagctaccct ctccggcatg aatttatcag   5880
ctagaacggt tgaatatcat attgatggtg atttgactgt ctccggcctt tctcacccgt   5940
ttgaatcttt acctacacat tactcaggca ttgcatttaa aatatatgag ggttctaaaa   6000 attttatcc ttgcgttgaa ataaaggctt ctcccgcaaa agtattacag ggtcataatg    6060
tttttggtac aaccgattta gctttatgct ctgaggcttt attgcttaat tttgctaatt   6120 cttttgccttg cctgtatgat ttattggatg ttggaatcgc ctgatgcggt attttctcct   6180
tacgcatctg tgcggtattt cacaccgcat atggtgcact ctcagtacaa tctgctctga   6240
tgccgcatag ttaagccagc cccgacaccc gccaacaccc gctgacgcgc cctgacgggc   6300
ttgtctgctc ccggcatccg cttacagaca agctgtgacc gtctccggga gctgcatgtg   6360
tcagaggttt tcaccgtcat caccgaaacg cgcgagacga agggcctcg tgatacgcct    6420 attttttatag gttaatgtca tgataataat ggtttcttag acgtcaggtg cacttttcg   6480 gggaaatgtg cgcggaaccc ctatttgttt atttttctaa atacattcaa atatgtatcc   6540
gctcatgaga caataaccct gataaatgct tcaataatat tgaaaaagga agagtatgag   6600
tattcaacat ttccgtgtcg cccttattcc cttttttgcg cattttgcc ttcctgttttt   6660 tgctcaccca gaaacgctgg tgaaagtaaa agatgctgaa gatcagttgg gtgcacgagt   6720
gggttacatc gaactggatc tcaacagcgg taagatcctt gagagttttc gccccgaaga   6780
acgttttcca atgatgagca cttttaaagt tctgctatgt ggcgcggtat tatcccgtat   6840
tgacgccggg caagagcaac tcggtcgccg catacactat tctcagaatg acttggttga   6900
gtactcacca gtcacagaaa agcatcttac ggatggcatg acagtaagag aattatgcag   6960
tgctgccata accatgagtg ataacactgc ggccaactta cttctgacaa cgatcggagg   7020
accgaaggag ctaaccgctt ttttgcacaa catgggggat catgtaactc gccttgatcg   7080
ttgggaaccg gagctgaatg aagccatacc aaacgacgag cgtgacacca cgatgcctgt   7140
```

-continued

| | |
|---|---|
| agcaatggca acaacgttgc gcaaactatt aactggcgaa ctacttactc tagcttcccg | 7200 |
| gcaacaatta atagactgga tggaggcgga taaagttgca ggaccacttc tgcgctcggc | 7260 |
| ccttccggct ggctggttta ttgctgataa atctggagcc ggtgagcgtg gtctcgcgg | 7320 |
| tatcattgca gcactggggc cagatggtaa gccctcccgt atcgtagtta tctacacgac | 7380 |
| ggggagtcag gcaactatgg atgaacgaaa tagacagatc gctgagatag gtgcctcact | 7440 |
| gattaagcat tggtaactgt cagaccaagt ttactcatat atactttaga ttgatttaaa | 7500 |
| acttcatttt taatttaaaa ggatctaggt gaagatcctt tttgataatc tcatgaccaa | 7560 |
| aatcccttaa cgtgagtttt cgttccactg agcgtcagac cccgtagaaa agatcaaagg | 7620 |
| atcttcttga tccttttt ttctgcgcgt aatctgctgc ttgcaaacaa aaaaaccacc | 7680 |
| gctaccagcg gtggtttgtt tgccggatca agagctacca actctttttc cgaaggtaac | 7740 |
| tggcttcagc agagcgcaga taccaaatac tgttcttcta gtgtagccgt agttaggcca | 7800 |
| ccacttcaag aactctgtag caccgcctac atacctcgct ctgctaatcc tgttaccagt | 7860 |
| ggctgctgcc agtggcgata gtcgtgtct taccgggttg gactcaagac gatagttacc | 7920 |
| ggataaggcg cagcggtcgg gctgaacggg gggttcgtgc acacagccca gcttggagcg | 7980 |
| aacgacctac accgaactga gatacctaca gcgtgagcta tgagaaagcg ccacgcttcc | 8040 |
| cgaagggaga aaggcggaca ggtatccggt aagcggcagg gtcggaacag gagagcgcac | 8100 |
| gagggagctt ccagggggaa acgcctggta tctttatagt cctgtcgggt ttcgccacct | 8160 |
| ctgacttgag cgtcgatttt tgtgatgctc gtcaggggg cggagcctat ggaaaaacgc | 8220 |
| cagcaacgcg gcctttttac ggttcctggc cttttgctgg ccttttgctc acatgttctt | 8280 |
| tcctgcgtta tcccctgatt ctgtggataa ccgtattacc gcctttgagt gagctgatac | 8340 |
| cgctcgccgc agccgaacga ccgagcgcag cgagtcagtg agcgaggaag cggaagagcg | 8400 |
| cccaatacgc aaaccgcctc tccccgcgcg ttggccgatt catta | 8445 |

<210> SEQ ID NO 8
<211> LENGTH: 7843
<212> TYPE: DNA
<213> ORGANISM: Artificial Sequence
<220> FEATURE:
<223> OTHER INFORMATION: pAAV-CAG-mu-SFMD.
<220> FEATURE:
<221> NAME/KEY: misc_feature
<222> LOCATION: (3469)..(3473)
<223> OTHER INFORMATION: n is a, c, g, or t

<400> SEQUENCE: 8

| | |
|---|---|
| atgcagctgc gcgctcgctc gctcactgag gcccagctgc gcgctcgctc gctcactgag | 60 |
| gccgcccggg caaagcccgg gcgtcgggcg acctttggtc gcccggcctc agtgagcgag | 120 |
| cgagcgcgca gagagggagt ggccaactcc atcactaggg gttccttgta gttaatgatt | 180 |
| aacccgccat gctacttatc tactcgacat tgattattga ctagttatta atagtaatca | 240 |
| attacggggt cattagttca tagcccatat atggagttcc gcgttacata acttacggta | 300 |
| aatggcccgc ctggctgacc gcccaacgac ccccgcccat tgacgtcaat aatgacgtat | 360 |
| gttcccatag taacgccaat agggactttc cattgacgtc aatgggtgga gtatttacgg | 420 |
| taaactgccc acttggcagt acatcaagtg tatcatatgc caagtacgcc ccctattgac | 480 |
| gtcaatgacg gtaaatggcc cgcctggcat tatgcccagt acatgacctt atgggacttt | 540 |
| cctacttggc agtacatcta cgtattagtc atcgctatta ccatggtcga ggtgagcccc | 600 |
| acgttctgct tcactctccc catctccccc ccctccccac cccaattttt gtatttattt | 660 |

```
attttttaat tattttgtgc agcgatgggg gcggggggg ggggggggcg cgcgccaggc    720
ggggcgggc ggggcgaggg gcgggcgggg gcgaggcgga gaggtgcggc ggcagccaat    780
cagagcggcg cgctccgaaa gtttccttt atggcgaggc ggcggcggcg gcggccctat    840
aaaaagcgaa gcgcgcggcg ggcgggagtc gctgcgttgc cttcgcccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg ggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc ccgcggtgc ggggggggct gcgaggggaa    1260
caaaggctgc gtgcggggtg tgtgcgtggg ggggtgagca gggggtgtgg gcgcgtcggt   1320
cgggctgcaa ccccccctgc acccccctcc ccgagttgct gagcacgcc cggcttcggg    1380
tgcggggctc cgtacggggc gtggcgcggg gctcgccgtg ccggcgggg ggtggcggca    1440
ggtgggggtg ccgggcgggg cggggccgcc tcgggccggg gagggctcgg gggaggggcg   1500
cggcggcccc cggagcgccg gcggctgtcg aggcgcggcg agccgcagcc attgccttt    1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cggggggac ggggcagggc    1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttgattaatt cgagcgaacg cgtatgcact gcccgggact ggcctgctgc   1980
acaattctgt tggtcctggg actctgcggc gcgcactcgc gcaacgtgct actgatagtt   2040
gcggatgacg gaggctttga gagtggtgta taacaacaa ctgccatcgc cacccctcac    2100
ctggatgccc tgtcccgcca cagccttatc ttccgtaacg ccttcacgtc tgtcagcagc   2160
tgttccccga ccgtgccag cctcctcacc ggcctgcccc agcatcagaa tggcatgtat    2220
gggctgcacc aggatgtgca tcacttcaac tcttttgaca aggtacagag ccttccgctg   2280
ctgctcaacc aggccggagt gcgcacaggc atcattggga agaagcacgt gggtccggag   2340
acggtgtatc cctttgactt tgcattcaca gaggagaaca gctctgtgat gcaggtgggg   2400
cggaacatca ctagaattaa gcaactggtc cagaaatttc tgcagactca ggatgacagg   2460
cccttcttcc tgtacgtggc tttccatgac ccgcaccgct gtgggcactc tcagcccag    2520
tatggaacct tctgtgagaa gtttggcaac ggagagagtg gaatggggta cattccagac   2580
tggacacccc agatctacga ccctcaggat gtgatggtgc cctactttgt cccggacaca   2640
ccagcagccc gagcagacct agctgctcag tacaccacca tcgggcggat ggaccaaggg   2700
gtaggtctgg tgctccagga gctgcgaggt gctggtgtgc tgaacgacac cctcatcatc   2760
ttcacatctg acaatggtat ccctttcccc agcggcagga ccaacctgta ctggccggt    2820
acagccgagc ctttgctggt gtcatctcca gagcacccac agcgctgggg ccaggtcagc   2880
gacgcctacg tgagccttct agacctcacc cctaccatcc tggactggtt ctccatcccg   2940
taccccagct atgccatctt tggctcaaag acgatccagc tcacaggccg atccctcctg   3000
```

```
ccggcgctgg aggcagagcc cctttgggcc actgtcttca gcagccagag ccaccacgag    3060
gtcaccatgt cctacccgat gcgctcggtg taccaccaga acttccgcct cattcacaac    3120
ctgagcttca agatgccatt tcccatcgac caagatttct atgtctcgcc gaccttccag    3180
gacctcctga accgaaccac cacaggccgg cccacgggct ggtacaagga cctccaccgt    3240
tactactacc gggaacgctg ggaactctac gacatcagcc gggaccctcg agagacacgg    3300
aacctggccg ctgacccaga cttggctcaa gtgctggaga tgctgaaagc tcagcttgtc    3360
aagtggcaat gggagacaca tgacccctgg gtgtgcgccc cagatggagt cctggaggaa    3420
aagctcacac cccagtgccg accgcttcac aatgaactct gaacgcgtnn nnngctagct    3480
cgatatcggc ctaggctgga tccgcgcggc cgcaagaatt cgagctcggt acccgggaat    3540
caattcactc ctcaggtgca ggctgcctat cagaaggtgg tggctggtgt ggccaatgcc    3600
ctggctcaca ataccactg agatcttttt ccctctgcca aaaattatgg ggacatcatg    3660
aagccccttg agcatctgac ttctggctaa taaaggaaat ttattttcat tgcaatagtg    3720
tgttggaatt ttttgtgtct ctcactcgga aggacatatg ggagggcaaa tcatttaaaa    3780
catcagaatg agtatttggt ttagagtttg gcaacatatg cccatatgct ggctgccatg    3840
aacaaaggtt ggctataaag aggtcatcag tatatgaaac agcccctgc tgtccattcc     3900 ttattccata gaaaagcctt gacttgaggt tagattttt ttatatttg ttttgtgtta    3960 ttttttttctt taacatccct aaaattttcc ttacatgttt tactagccag attttcctc    4020 ctctcctgac tactcccagt catagctgtc cctcttctct tatggagatc cctcgacctg    4080
cagcccaagc tgtagataag tagcatggcg ggttaatcat taactacaag gaaccccctag   4140 tgatggagtt ggccactccc tctctgcgcg ctcgctcgct cactgaggcc gggcgaccaa    4200
aggtcgcccg acgcccgggc tttgcccggg cggcctcagt gagcgagcga gcgcgcagct    4260
ggcgtaatag cgaagaggcc cgcaccgatc gcccttccca acagttgcgc agcctgaatg    4320
gcgaatggcg attccgttgc aatggctggc ggtaatattg ttctggatat taccagcaag    4380
gccgatagtt tgagttcttc tactcaggca agtgatgtta ttactaatca agaagtatt    4440 gcgacaacgg ttaatttgcg tgatggacag actcttttac tcggtggcct cactgattat    4500
aaaaacactt ctcaggattc tggcgtaccg ttcctgtcta aaatcccttt aatcggcctc    4560
ctgtttagct cccgctctga ttctaacgag gaaagcacgt tatacgtgct cgtcaaagca    4620
accatagtac gcgccctgta gcggcgcatt aagcgcggcg ggtgtggtgg ttacgcgcag    4680
cgtgaccgct acacttgcca gcgccctagc gcccgctcct ttcgctttct tcccttcctt    4740
tctcgccacg ttcgccggct ttccccgtca agctctaaat cggggctcc ctttagggtt    4800 ccgatttagt gctttacggc acctcgaccc caaaaaactt gattagggtg atggttcacg    4860
tagtgggcca tcgccctgat agacggtttt tcgccctttg acgttggagt ccacgttctt    4920
taatagtgga ctcttgttcc aaactggaac aacactcaac cctatctcgg tctattcttt    4980
tgatttataa gggattttgc cgatttcggc ctattggtta aaaatgagc tgatttaaca    5040 aaaatttaac gcgaatttta acaaaatatt aacgcttaca atttaaatat tgcttatac    5100 aatcttcctg ttttgggggc ttttctgatt atcaaccggg gtacatatga ttgacatgct    5160
agttttacga ttaccgttca tcgattctct tgtttgctcc agactctcag gcaatgacct    5220
gatagccttt gtagagacct ctcaaaaata gctaccctct ccggcatgaa tttatcagct    5280
agaacggttt aatatcatat tgatggtgat ttgactgtct ccggcctttc tcacccgttt    5340
gaatctttac ctacacatta ctcaggcatt gcatttaaaa tatatgaggg ttctaaaaat    5400
```

```
ttttatcctt gcgttgaaat aaaggcttct cccgcaaaag tattacaggg tcataatgtt    5460
tttggtacaa ccgatttagc tttatgctct gaggctttat tgcttaattt tgctaattct    5520
ttgccttgcc tgtatgattt attggatgtt ggaatcgcct gatgcggtat tttctcctta    5580
cgcatctgtg cggtatttca caccgcatat ggtgcactct cagtacaatc tgctctgatg    5640
ccgcatagtt aagccagccc cgacacccgc caacacccgc tgacgcgccc tgacgggctt    5700
gtctgctccc ggcatccgct tacagacaag ctgtgaccgt ctccgggagc tgcatgtgtc    5760
agaggttttc accgtcatca ccgaaacgcg cgagacgaaa gggcctcgtg atacgcctat    5820
ttttataggt taatgtcatg ataataatgg tttcttagac gtcaggtggc acttttcggg    5880
gaaatgtgcg cggaacccct atttgtttat ttttctaaat acattcaaat atgtatccgc    5940
tcatgagaca taaccctga taaatgcttc aataatattg aaaaaggaag agtatgagta    6000
ttcaacattt ccgtgtcgcc cttattccct tttttgcggc attttgcctt cctgtttttg    6060
ctcacccaga aacgctggtg aaagtaaaag atgctgaaga tcagttgggt gcacgagtgg    6120
gttacatcga actggatctc aacagcggta agatccttga gttttcgc cccgaagaac    6180 gttttccaat gatgagcact tttaaagttc tgctatgtgg cgcggtatta tcccgtattg    6240
acgccgggca agagcaactc ggtcgccgca tacactattc tcagaatgac ttggttgagt    6300
actcaccagt cacagaaaag catcttacgg atggcatgac agtaagagaa ttatgcagtg    6360
ctgccataac catgagtgat aacactgcgg ccaacttact tctgacaacg atcggaggac    6420
cgaaggagct aaccgctttt ttgcacaaca tgggggatca tgtaactcgc cttgatcgtt    6480
gggaaccgga gctgaatgaa gccataccaa acgacgagcg tgacaccacg atgcctgtag    6540
caatggcaac aacgttgcgc aaactattaa ctggcgaact acttactcta gcttcccggc    6600
aacaattaat agactggatg gaggcggata agttgcagg accacttctg cgctcggccc    6660
ttccggctgg ctggtttatt gctgataaat ctggagccgg tgagcgtggg tctcgcggta    6720
tcattgcagc actggggcca gatggtaagc cctcccgtat cgtagttatc tacacgacgg    6780
ggagtcaggc aactatggat gaacgaaata gacagatcgc tgagataggt gcctcactga    6840
ttaagcattg gtaactgtca gaccaagttt actcatatat actttagatt gatttaaaac    6900 ttcatttta atttaaaagg atctaggtga agatccttt tgataatctc atgaccaaaa    6960
tcccttaacg tgagttttcg ttccactgag cgtcagaccc cgtagaaaag atcaaaggat    7020
cttcttgaga tccttttttt ctgcgcgtaa tctgctgctt gcaaacaaaa aaaccaccgc    7080
taccagcggt ggtttgtttg ccggatcaag agctaccaac tcttttttcg aaggtaactg    7140
gcttcagcag agcgcagata ccaaatactg ttcttctagt gtagccgtag ttaggccacc    7200
acttcaagaa ctctgtagca ccgcctacat acctcgctct gctaatcctg ttaccagtgg    7260
ctgctgccag tggcgataag tcgtgtctta ccgggttgga ctcaagacga tagttaccgg    7320
ataaggcgca gcggtcgggc tgaacggggg gttcgtgcac acagcccagc ttggagcgaa    7380
cgacctacac cgaactgaga tacctacagc gtgagctatg agaaagcgcc acgcttcccg    7440
aagggagaaa ggcggacagg tatccggtaa gcggcagggt cggaacagga gagcgcacga    7500
gggagcttcc agggggaaac gcctggtatc tttatagtcc tgtcgggttt cgccacctct    7560
gacttgagcg tcgatttttg tgatgctcgt caggggggcg gagcctatgg aaaaacgcca    7620
gcaacgcggc cttttacgg ttcctggcct tttgctggcc ttttgctcac atgttctttc    7680
ctgcgttatc ccctgattct gtggataacc gtattaccgc ctttgagtga gctgataccg    7740
```

<210> SEQ ID NO 9
<211> LENGTH: 7796
<212> TYPE: DNA
<213> ORGANISM: Artificial Sequence
<220> FEATURE:
<223> OTHER INFORMATION: pAAV-CAG-co-hu-SFMD.

<400> SEQUENCE: 9

```
ctcgccgcag ccgaacgacc gagcgcagcg agtcagtgag cgaggaagcg gaagagcgcc      7800
caatacgcaa accgcctctc cccgcgcgtt ggccgattca tta                        7843 atgcagctgc gcgctcgctc gctcactgag gcccagctgc gcgctcgctc gctcactgag       60
gccgcccggg caaagcccgg gcgtcgggcg acctttggtc gcccggcctc agtgagcgag      120
cgagcgcgca gagagggagt ggccaactcc atcactaggg gttccttgta gttaatgatt      180
aacccgccat gctacttatc tactcgacat tgattattga ctagttatta atagtaatca      240
attacgggt cattagttca tagcccatat atggagttcc gcgttacata acttacggta       300
aatggcccgc ctggctgacc gcccaacgac ccccgcccat tgacgtcaat aatgacgtat      360
gttcccatag taacgccaat agggactttc cattgacgtc aatgggtgga gtatttacgg      420
taaactgccc acttggcagt acatcaagtg tatcatatgc caagtacgcc ccctattgac      480
gtcaatgacg gtaaatggcc cgcctggcat tatgcccagt acatgacctt atgggacttt      540
cctacttggc agtacatcta cgtattagtc atcgctatta ccatggtcga ggtgagcccc      600
acgttctgct tcactctccc catctccccc cctccccac ccccaatttt gtatttattt       660
atttttaat tattttgtgc agcgatgggg gcggggggg gggggggcg cgcgccaggc         720
ggggcgggc ggggcgaggg gcggggcggg gcgaggcgga gaggtgcggc ggcagccaat       780
cagagcggcg cgctccgaaa gtttcctttt atggcgaggc ggcggcggcg gcggccctat      840
aaaaagcgaa gcgcgcggcg gcgggagtc gctgcgttgc cttcgccccg tgccccgctc       900
cgcgccgcct cgcgccgccc gccccggctc tgactgaccg cgttactccc acaggtgagc      960
gggcgggacg gcccttctcc tccgggctgt aattagcgct tggtttaatg acggcttgtt     1020
tcttttctgt ggctgcgtga aagccttgag gggctccggg agggccctt gtgcgggggg      1080
agcggctcgg ggggtgcgtg cgtgtgtgtg tgcgtgggga gcgccgcgtg cggctccgcg     1140
ctgcccggcg gctgtgagcg ctgcgggcgc ggcgcgggc tttgtgcgct ccgcagtgtg     1200
cgcgaggga gcgcggccgg gggcggtgcc ccgcggtgcg gggggctgcg aggggaacaa      1260
aggctgcgtg cgggggtgtgt gcgtgggggg gtgagcaggg ggtgtgggcg cgtcggtcgg     1320
gctgcaaccc cccctgcacc cccctccccg agttgctgag cacggcccgg cttcgggtgc     1380
ggggctccgt acggggcgtg gcgcggggct cgccgtgccg gcgggggggt ggcggcaggt     1440
gggggtgccg ggcggggcgg ggccgcctcg ggccgggag ggctcggggg aggggcgcgg      1500
cggccccgg agcgccggcg gctgtcgagg cgcggcgagc cgcagccatt gccttttatg     1560
gtaatcgtgc gagagggcgc agggacttcc tttgtcccaa atctgtgcgg agccgaaatc     1620
tgggaggcgc cgccgcaccc cctctagcgg gcgcgggcg aagcggtgcg gcgccggcag     1680
gaaggaaatg ggcgggagg gccttcgtgc gtcgccgcgc cgccgtcccc ttctccctct     1740
ccagcctcgg ggctgtccgc gggggacgg ctgccttcgg ggggacggg gcagggcggg     1800
gttcggcttc tggcgtgtga ccggcggctc tagagcctct gctaaccatg ttcatgcctt     1860
cttctttttc ctacagctcc tgggcaacgt gctggttatt gtgctgtctc atcatttgg     1920
caaagaattg attaattcga cgaacgcgt gccaccatga gctgccctgt gccgcctgt     1980
```

```
tgtgccctgc tgctggtgct gggactgtgc agagccagac cccggaacgc tctgctgctg    2040
ctggccgacg atggcggatt tgagagcggc gcctacaaca cagcgccat tgccaccct      2100 catctggacg ccctggccag aagaagcctg ctgttccgga acgccttcac cagcgtgtcc    2160
agctgcagcc ctagcagagc ttccctgctg acaggcctgc cccagcatca gaatggcatg    2220
tacggcctgc accaggatgt gcatcacttc aacagcttcg acaaagtgcg gagcctgcca    2280
ctgctcctgt cacaggctgg cgtgagaacc ggcatcatcg gcaagaaaca cgtgggcccc    2340
gagacagtgt accccttcga cttcgcctac accgaagaga acggcagcgt gctgcaggtc    2400
ggccggaaca tcacccggat caagctgctc gtgcggaagt tctccagac ccaggacgac     2460 cggcccttct tcctgtacgt ggccttccac gaccctcaca gatgcggcca cagccagccc    2520
cagtacggca ccttctgcga aagttcggc aacggcgaga gcggcatggg cagaatcccc     2580
gactggaccc cccaggcata cgaccctctg acgtgctgg tgccctactt cgtgcccaac     2640
acccctgccg ccagagctga tctggccgcc cagtacacca ccgtgggcag aatggatcag    2700
ggcgtgggcc tggtgctgca ggaactgagg gacgctggcg tgctgaacga caccctggtc    2760
atcttcacct ccgacaacgg catcccattc cccagcggcc ggaccaatct gtactggccc    2820
ggcacagccg aacctctgct ggtgtccagc cccgagcacc ctaagagatg gggccaggtg    2880
tccgaggcct acgtgtccct gctggacctg accccaccag tcctggactg gttcagcatc    2940
ccctacccca gctacgccat ctttggaagc aagaccatcc acctgaccgg cagatctctg    3000
ctgcctgccc tggaagctga gcctctgtgg gccaccgtgt tcggcagcca gagccaccac    3060
gaagtgacca tgagctaccc catgcggagc gtgcagcacc ggcacttccg gctggtgcac    3120
aacctgaact tcaagatgcc cttcccaatc gaccaggact tttacgtgtc ccccaccttc    3180
caggacctgc tgaacagaac cacagccggc cagcccaccg gctggtacaa ggacctgcgg    3240
cactactact accgggccag atgggagctg tacgacagaa gccggacccc cacgagaca    3300 cagaacctgg ccaccgaccc cagattcgcc cagctcctgg aaatgctgcg ggaccagctg    3360
gccaagtggc agtgggagac acacgaccct tgggtctgcg ctcccgacgg cgtgctggaa    3420
gagaagctgt cccccccagtg ccagccactg cacaacgagc tgtgatgaga attcgagctc    3480
ggtacccggg aatcaattca ctcctcaggt gcaggctgcc tatcagaagg tggtggctgg    3540
tgtggccaat gccctggctc acaaatacca ctgagatctt tttccctctg ccaaaaatta    3600
tggggacatc atgaagcccc ttgagcatct gacttctggc taataaagga aatttatttt    3660
cattgcaata gtgtgttgga attttttgtg tctctcactc ggaaggacat atgggagggc    3720
aaatcattta aaacatcaga atgagtattt ggtttagagt ttggcaacat atgcccatat    3780
gctggctgcc atgaacaaag gttggctata aagaggtcat cagtatatga acagccccc    3840 tgctgtccat tccttattcc atagaaaagc cttgacttga ggttagattt tttttatatt    3900
ttgttttgtg ttatttttt ctttaacatc cctaaaattt tccttacatg ttttactagc     3960 cagattttc ctcctctcct gactactccc agtcatagct gtccctcttc tcttatggag     4020
atccctcgac ctgcagccca agctgtgat aagtagcatg gcgggttaat cattaactac     4080
aaggaacccc tagtgatgga gttggccact ccctctctgc gcgctcgctc gctcactgag    4140
gccgggcgac caaaggtcgc ccgacgcccg ggctttgccc gggcggcctc agtgagcgag    4200
cgagcgcgca gctggcgtaa tagcgaagag gcccgcaccg atcgcccttc ccaacagttg    4260
cgcagcctga atggcgaatg gcgattccgt tgcaatggct ggcggtaata ttgttctgga    4320
```

```
tattaccagc aaggccgata gtttgagttc ttctactcag gcaagtgatg ttattactaa      4380
tcaaagaagt attgcgacaa cggttaattt gcgtgatgga cagactcttt tactcggtgg      4440
cctcactgat tataaaaaca cttctcagga ttctggcgta ccgttcctgt ctaaaatccc      4500
tttaatcggc ctcctgttta gctcccgctc tgattctaac gaggaaagca cgttatacgt      4560
gctcgtcaaa gcaaccatag tacgcgccct gtagcggcgc attaagcgcg gcgggtgtgg      4620
tggttacgcg cagcgtgacc gctacacttg ccagcgccct agcgcccgct cctttcgctt      4680
tcttcccttc ctttctcgcc acgttcgccg gctttccccg tcaagctcta atcgggggc       4740 tcccttagg gttccgattt agtgctttac ggcacctcga ccccaaaaaa cttgattagg       4800
gtgatggttc acgtagtggg ccatcgccct gatagacggt ttttcgccct ttgacgttgg      4860
agtccacgtt ctttaatagt ggactcttgt tccaaactgg aacaacactc aaccctatct      4920
cggtctattc ttttgattta aagggatttt gccgatttc ggcctattgg ttaaaaatg       4980 agctgattta acaaaaattt aacgcgaatt ttaacaaaat attaacgctt acaatttaaa      5040
tatttgctta tacaatcttc ctgttttgg ggcttttctg attatcaacc ggggtacata      5100
tgattgacat gctagtttta cgattaccgt tcatcgattc tcttgtttgc tccagactct      5160
caggcaatga cctgatagcc tttgtagaga cctctcaaaa atagctaccc tctccggcat      5220
gaatttatca gctagaacgg ttgaatatca tattgatggt gatttgactg tctccggcct      5280
ttctcacccg tttgaatctt tacctacaca ttactcaggc attgcattta aaatatatga      5340
gggttctaaa aatttttatc cttgcgttga aataaaggct tctcccgcaa agtattaca       5400 gggtcataat gttttggta caaccgattt agctttatgc tctgaggctt tattgcttaa       5460
ttttgctaat tctttgcctt gcctgtatga tttattggat gttggaatcg cctgatgcgg      5520
tattttctcc ttacgcatct gtgcggtatt tcacaccgca tatggtgcac tctcagtaca      5580
atctgctctg atgccgcata gttaagccag ccccgacacc cgccaacacc cgctgacgcg      5640
ccctgacggg cttgtctgct cccggcatcc gcttacagac aagctgtgac cgtctccggg      5700
agctgcatgt gtcagaggtt ttcaccgtca tcaccgaaac gcgcgagacg aaagggcctc      5760
gtgatacgcc tatttttata ggttaatgtc atgataataa tggtttctta gacgtcaggt      5820 ggcactttc ggggaaatgt gcgcggaacc cctatttgtt tatttttcta aatacattca       5880
aatatgtatc cgctcatgag acaataaccc tgataaatgc ttcaataata ttgaaaaagg      5940
aagagtatga gtattcaaca tttccgtgtc gcccttattc ccttttttgc ggcattttgc      6000
cttcctgttt ttgctcaccc agaaacgctg gtgaaagtaa aagatgctga agatcagttg      6060
ggtgcacgag tgggttacat cgaactggat ctcaacagcg gtaagatcct tgagagtttt      6120
cgccccgaag aacgttttcc aatgatgagc acttttaaag ttctgctatg tggcgcggta      6180
ttatcccgta ttgacgccgg gcaagagcaa ctcggtcgcc gcatacacta ttctcagaat      6240
gacttggttg agtactcacc agtcacagaa aagcatctta cggatggcat gacagtaaga      6300
gaattatgca gtgctgccat aaccatgagt gataacactg cggccaactt acttctgaca      6360
acgatcggag gaccgaagga gctaaccgct tttttgcaca acatggggga tcatgtaact      6420
cgccttgatc gttgggaacc ggagctgaat gaagccatac caaacgacga gcgtgacacc      6480
acgatgcctg tagcaatggc aacaacgttg cgcaaactat taactggcga actacttact      6540
ctagcttccc ggcaacaatt aatagactgg atggaggcgg ataaagttgc aggaccactt      6600
ctgcgctcgg cccttccggc tggctggttt attgctgata aatctggagc cggtgagcgt      6660
gggtctcgcg gtatcattgc agcactgggg ccagatggta agccctcccg tatcgtagtt      6720
```

-continued

```
atctacacga cggggagtca ggcaactatg gatgaacgaa atagacagat cgctgagata      6780
ggtgcctcac tgattaagca ttggtaactg tcagaccaag tttactcata tatactttag      6840
attgatttaa aacttcattt ttaatttaaa aggatctagg tgaagatcct ttttgataat      6900
ctcatgacca aaatccctta acgtgagttt tcgttccact gagcgtcaga ccccgtagaa      6960
aagatcaaag gatcttcttg agatcctttt tttctgcgcg taatctgctg cttgcaaaca      7020
aaaaaaccac cgctaccagc ggtggtttgt ttgccggatc aagagctacc aactcttttt      7080
ccgaaggtaa ctggcttcag cagagcgcag ataccaaata ctgttcttct agtgtagccg      7140
tagttaggcc accacttcaa gaactctgta gcaccgccta catacctcgc tctgctaatc      7200
ctgttaccag tggctgctgc cagtggcgat aagtcgtgtc ttaccgggtt ggactcaaga      7260
cgatagttac cggataaggc gcagcggtcg ggctgaacgg ggggttcgtg cacacagccc      7320
agcttggagc gaacgaccta caccgaactg agatacctac agcgtgagct atgagaaagc      7380
gccacgcttc ccgaagggag aaaggcggac aggtatccgg taagcggcag ggtcggaaca      7440
ggagagcgca cgagggagct tccaggggga aacgcctggt atctttatag tcctgtcggg      7500
tttcgccacc tctgacttga gcgtcgattt ttgtgatgct cgtcaggggg gcggagccta      7560
tggaaaaacg ccagcaacgc ggccttttta cggttcctgg ccttttgctg gccttttgct      7620
cacatgttct ttcctgcgtt atcccctgat tctgtggata accgtattac cgcctttgag      7680
tgagctgata ccgctcgccg cagccgaacg accgagcgca gcgagtcagt gagcgaggaa      7740
gcggaagagc gcccaatacg caaaccgcct ctccccgcgc gttggccgat tcatta          7796
```

<210> SEQ ID NO 10
<211> LENGTH: 7193
<212> TYPE: DNA
<213> ORGANISM: Artificial Sequence
<220> FEATURE:
<223> OTHER INFORMATION: pGG2-hAAT-mu-SFMD.

<400> SEQUENCE: 10

```
cgcgtatgca ctgcccggga ctggcctgct gcacaattct gttggtcctg ggactctgcg        60
gcgcgcactc gcgcaacgtg ctactgatag ttgcggatga cggaggcttt gagagtggtg       120
tatacaacaa cactgccatc gccacccctc acctggatgc cctgtcccgc acagccttta       180
tcttccgtaa cgccttcacg tctgtcagca gctgttcccc gagccgtgcc agcctcctca       240
ccggcctgcc ccagcatcag aatggcatgt atgggctgca ccaggatgtg catcacttca       300
actcttttga caaggtacag agccttccgc tgctgctcaa ccaggccgga gtgcgcacag       360
gcatcattgg gaagaagcac gtgggtccgg agacggtgta tcccctttga ctttgcattca     420
cagaggagaa cagctctgtg atgcaggtgg ggcggaacat cactagaatt aagcaactgg       480
tccagaaatt tctgcagact caggatgaca ggcccttctt cctgtacgtg gctttccatg       540
acccgcaccg ctgtgggcac tctcagcccc agtatgaac cttctgtgag aagtttggca       600
acggagagag tggaatgggg tacattccag actggacacc ccagatctac gaccctcagg       660
atgtgatggt gccctacttt gtcccggaca caccagcagc ccgagcagac ctagctgctc       720
agtacaccac catcgggcgg atggaccaag gggtaggtct ggtgctccag gagctgcgag       780
gtgctggtgt gctgaacgac accctcatca tcttcacatc tgacaatggt atccctttcc       840
ccagcggcag gaccaacctg tactggcccg gtacagccga gcctttgctg gtgtcatctc       900
cagagcaccc acagcgctgg ggccaggtca gcgacgccta cgtgagcctt ctagacctca       960
```

| | |
|---|---|
| cccctaccat cctggactgg ttctccatcc cgtaccccag ctatgccatc tttggctcaa | 1020 |
| agacgatcca gctcacaggc cgatccctcc tgccggcgct ggaggcagag cccctttggg | 1080 |
| ccactgtctt cagcagccag agccaccacg aggtcaccat gtcctacccg atgcgctcgg | 1140 |
| tgtaccacca gaacttccgc ctcattcaca acctgagctt caagatgcca tttcccatcg | 1200 |
| accaagattt ctatgtctcg ccgaccttcc aggacctcct gaaccgaacc accacaggcc | 1260 |
| ggcccacggg ctggtacaag gacctccacc gttactacta ccgggaacgc tgggaactct | 1320 |
| acgacatcag ccgggaccct cgagagacac ggaacctggc cgctgaccca gacttggctc | 1380 |
| aagtgctgga gatgctgaaa gctcagcttg tcaagtggca atgggagaca catgacccct | 1440 |
| gggtgtgcgc cccagatgga gtcctggagg aaaagctcac accccagtgc cgaccgcttc | 1500 |
| acaatgaact ctgaacgcgt gatatcggat cccggccggc ggccgcttcc ctttagtgag | 1560 |
| ggttaatgct tcgagcagac atgataagat acattgatga gtttggacaa accacaacta | 1620 |
| gaatgcagtg aaaaaaatgc tttatttgtg aaatttgtga tgctattgct ttatttgtaa | 1680 |
| ccattataag ctgcaataaa caagttaaca acaacaattg cattcatttt atgtttcagg | 1740 |
| ttcaggggga gatgtgggag gttttttaaa gcaagtaaaa cctctacaaa tgtggtaaaa | 1800 |
| tccgataagg gactagagca tggctacgta gataagtagc atggcgggtt aatcattaac | 1860 |
| tacaaggaac ccctagtgat ggagttggcc actccctctc tgcgcgctcg ctcgctcact | 1920 |
| gaggccgggc gaccaaaggt cgcccgacgc ccgggctttg cccgggcggc ctcagtgagc | 1980 |
| gagcgagcgc gccagctggc gtaatagcga agaggcccgc accgatcgcc cttcccaaca | 2040 |
| gttgcgcagc ctgaatggcg aatggaattc cagacgattg agcgtcaaaa tgtaggtatt | 2100 |
| tccatgagcg ttttttccgtt gcaatggctg cggtaatat tgttctggat attaccagca | 2160 |
| aggccgatag tttgagttct tctactcagg caagtgatgt tattactaat caaagaagta | 2220 |
| ttgcgacaac ggttaatttg cgtgatggac agactctttt actcggtggc ctcactgatt | 2280 |
| ataaaaacac ttctcaggat tctggcgtac cgttcctgtc taaatccct ttaatcggcc | 2340 |
| tcctgtttag ctcccgctct gattctaacg aggaaagcac gttatacgtg ctcgtcaaag | 2400 |
| caaccatagt acgcgccctg tagcggcgca ttaagcgcgg cgggtgtggt ggttacgcgc | 2460 |
| agcgtgaccg ctacacttgc cagcgcccta gcgcccgctc ctttcgcttt cttcccttcc | 2520 |
| tttctcgcca cgttcgccgg ctttccccgt caagctctaa atcggggggct ccctttaggg | 2580 |
| ttccgattta gtgctttacg gcacctcgac cccaaaaaac ttgattaggg tgatggttca | 2640 |
| cgtagtgggc catcgccctg atagacggtt tttcgccctt gacgttgga gtccacgttc | 2700 |
| gcacctcgac cccaaaaaac ttgattaggg tgatggttca cgtagtgggc catcgccctg | 2760 |
| atagacggtt tttcgccctt gacgttgga gtccacgttc taaaaaatga gctgatttaa | 2820 |
| caaaaattta acgcgaattt taacaaaata ttaacgtcta caatttaaat atttgcttat | 2880 |
| acaatcttcc tgttttttggg gcttttctga ttatcaaccg ggtacatat gattgacatg | 2940 |
| ctagttttac gattaccgtt catcgattct cttgtttgct ccagactctc aggcaatgac | 3000 |
| ctgatagcct ttgtagagac ctctcaaaaa tagctaccct ctccggcatg aatttatcag | 3060 |
| ctagaacggt tgaatatcat attgatgtg atttgactgt ctccggcctt tctcacccgt | 3120 |
| ttgaatcttt acctacacat tactcaggca ttgcatttaa aatatatgag ggttctaaaa | 3180 |
| atttttatcc ttgcgttgaa ataaaggctt ctcccgcaaa agtattacag gtcataatg | 3240 |
| ttttttggtac aaccgattta gctttatgct ctgaggcttt attgcttaat tttgctaatt | 3300 |
| cttttgccttg cctgtatgat ttattggatg ttggaatcgc ctgatgcggt attttctcct | 3360 |

```
tacgcatctg tgcggtattt cacaccgcat atggtgcact ctcagtacaa tctgctctga    3420
tgccgcatag ttaagccagc cccgacaccc gccaacaccc gctgacgcgc cctgacgggc    3480
ttgtctgctc ccggcatccg cttacagaca agctgtgacc gtctccggga gctgcatgtg    3540
tcagaggttt tcaccgtcat caccgaaacg cgcgagacga aagggcctcg tgatacgcct    3600
atttttatag gttaatgtca tgataataat ggtttcttag acgtcaggtg cacttttcg     3660 gggaaatgtg cgcggaaccc ctatttgttt attttctaa atacattcaa atatgtatcc     3720
gctcatgaga caataaccct gataaatgct tcaataatat tgaaaaagga gagtatgag     3780 tattcaacat ttccgtgtcg cccttattcc cttttttgcg gcattttgcc ttcctgtttt    3840
tgctcaccca gaaacgctgg tgaaagtaaa agatgctgaa gatcagttgg gtgcacgagt    3900
gggttacatc gaactggatc tcaacagcgg taagatcctt gagagttttc gccccgaaga    3960
acgttttcca atgatgagca cttttaaagt tctgctatgt ggcgcggtat tatcccgtat    4020
tgacgccggg caagagcaac tcggtcgccg catacactat tctcagaatg acttggttga    4080
gtactcacca gtcacagaaa agcatcttac ggatggcatg acagtaagag aattatgcag    4140
tgctgccata accatgagtg ataacactgc ggccaactta cttctgacaa cgatcggagg    4200
accgaaggag ctaaccgctt ttttgcacaa catgggggat catgtaactc gccttgatcg    4260
ttgggaaccg gagctgaatg aagccatacc aaacgacgag cgtgacacca cgatgcctgt    4320
agcaatggca acaacgttgc gcaaactatt aactggcgaa ctacttactc tagcttcccg    4380
gcaacaatta atagactgga tggaggcgga taaagttgca ggaccacttc tgcgctcggc    4440
ccttccggct ggctggttta ttgctgataa atctggagcc ggtgagcgtg ggtctcgcgg    4500
tatcattgca gcactggggc cagatggtaa gccctcccgt atcgtagtta tctacacgac    4560
ggggagtcag gcaactatgg atgaacgaaa tagacagatc gctgagatag gtgcctcact    4620
gattaagcat tggtaactgt cagaccaagt ttactcatat atactttaga ttgatttaaa    4680
acttcatttt taatttaaaa ggatctaggt gaagatcctt tttgataatc tcatgaccaa    4740
aatcccttaa cgtgagtttt cgttccactg agcgtcagac cccgtagaaa agatcaaagg    4800
atcttcttga tccttttttt ttctgcgcgt aatctgctgc ttgcaaacaa aaaaaccacc    4860
gctaccagcg gtggtttgtt tgccggatca agagctacca actctttttc cgaaggtaac    4920
tggcttcagc agagcgcaga taccaaatac tgtccttcta gtgtagccgt agttaggcca    4980
ccacttcaag aactctgtag caccgcctac atacctcgct ctgctaatcc tgttaccagt    5040
ggctgctgcc agtggcgata gtcgtgtct taccgggttg gactcaagac gatagttacc     5100
ggataaggcg cagcggtcgg gctgaacggg gggttcgtgc acacagccca gcttggagcg    5160
aacgacctac accgaactga gatacctaca gcgtgagcta tgagaaagcg ccacgcttcc    5220
cgaagggaga aaggcggaca ggtatccggt aagcggcagg gtcggaacag gagagcgcac    5280
gagggagctt ccaggggaa acgcctggta tctttatagt cctgtcgggt ttcgccacct     5340
ctgacttgag cgtcgatttt tgtgatgctc gtcaggggg cggagcctat ggaaaaacgc     5400
cagcaacgcg gcctttttac ggttcctggc cttttgctgg ccttttgctc acatgttctt    5460
tcctgcgtta tcccctgatt ctgtggataa ccgtattacc gcctttgagt gagctgatac    5520
cgctcgccgc agccgaacga ccgagcgcag cgagtcagtg agcgaggaag cggaagagcg    5580
cccaatacgc aaaccgcctc tccccgcgcg ttggccgatt cattaatgca gcagctgcgc    5640
gctcgctcgc tcactgaggc cgcccgggca aagcccgggc gtcgggcgac ctttggtcgc    5700
```

```
ccggcctcag tgagcgagcg agcgcgcaga gagggagtgg ccaactccat cactagggt      5760 tccttgtagt taatgattaa cccgccatgc tacttatcta ccggcctcag tgagcgagcg     5820
agcgcgcaga gagggagtgg ccaactccat cactagggt tccttgtagt taatgattaa    5880
cccgccatgc tacttatcta cactagtaag cttgcgaatt ccagtctaca gagaggtctc    5940
tgacctctgc cccagctcca aggtcagcag gcagggaggg ctgtgtgttt gctgtttgct    6000
gcttgcaatg tttgcccatt ttagggacat gagtaggctg aagtttgttc agtgtggact    6060
tcagaggcag cacacaaaca gcaagcttgc gaattccagt ctacagagag gtctctgacc    6120
tctgccccag ctccaaggtc agcaggcagg gagggctgtg tgtttgctgt ttgctgcttg    6180
caatgtttgc ccattttagg gacatgagta ggctgaagtt tgttcagtgt ggacttcaga    6240
ggcagcacac aaacagcaag cttgcgaatt ccagtctaca gagaggtctc tgacctctgc    6300
cccagctcca aggtcagcag gcagggaggg ctgtgtgttt gctgtttgct gcttgcaatg    6360
tttgcccatt ttagggacat gagtaggctg aagtttgttc agtgtggact tcagaggcag    6420
cacacaaaca gcaagctttg ctctagactg gaattcgtcg acgagctccc tatagtgagt    6480
cgtattagag ccgactgac ccggtacccg gggatcttgc taccagtgga acagccacta    6540
aggattctgc agtgagagca gagggccagc taagtggtac tctcccagag actgtctgac    6600
tcacgccacc ccctccacct tggacacagg acgctgtggt ttctgagcca ggtacaatga    6660
ctcctttcgg taagtgcagt ggaagctgta cactgcccag gcaaagcgtc cgggcagcgt    6720
aggcgggcga ctcagatccc agccagtgga cttagcccct gtttgctcct ccgataactg    6780
gggtgacctt ggttaatatt caccagcagc ctccccgtt gccctctgg atccactgct     6840 taaatacgga cgaggacagg gccctgtctc ctcagcttca ggcaccacca ctgacctggg    6900
acagtgaatg tcccctgat ctgcggccgt gactctctta aggtagcctt gcagaagttg    6960
gtcgtgaggc actgggcagg taagtatcaa ggttacaaga caggtttaag gagaccaata    7020
gaaactgggc ttgtcgagac agagaagact cttgcgtttc tgataggcac ctattggtct    7080
tactgacatc cactttgcct ttctctccac aggtgtccac tcccagttca attacagctc    7140
ttaaggctag agtacttaat acgactcact ataggctagc ctcgacctcg aga            7193
```

<210> SEQ ID NO 11
<211> LENGTH: 7199
<212> TYPE: DNA
<213> ORGANISM: Artificial Sequence
<220> FEATURE:
<223> OTHER INFORMATION: pGG2-hAAT-co-hu-SFMD.

<400> SEQUENCE: 11

```
cattaatgca gcagctgcgc gctcgctcgc tcactgaggc cgcccgggca aagcccgggc      60
gtcgggcgac ctttggtcgc ccggcctcag tgagcgagcg agcgcgcaga gagggagtgg    120
ccaactccat cactagggt tccttgtagt taatgattaa cccgccatgc tacttatcta    180
cgtagccatg ctctagacat ggctcgacag atctgatatc atcgatgaat tcgagctcgg    240
tacccggccg cagatttagg tgacactata gaatatgcat cactagtaag cttgcgaatt    300
ccagtctaca gagaggtctc tgacctctgc cccagctcca aggtcagcag gcagggaggg    360
ctgtgtgttt gctgtttgct gcttgcaatg tttgcccatt ttagggacat gagtaggctg    420
aagtttgttc agtgtggact tcagaggcag cacacaaaca gcaagcttgc gaattccagt    480
ctacagagag gtctctgacc tctgccccag ctccaaggtc agcaggcagg gagggctgtg    540
tgtttgctgt ttgctgcttg caatgtttgc ccattttagg gacatgagta ggctgaagtt    600
```

```
tgttcagtgt ggacttcaga ggcagcacac aaacagcaag cttgcgaatt ccagtctaca    660
gagaggtctc tgacctctgc cccagctcca aggtcagcag gcagggaggg ctgtgtgttt    720
gctgtttgct gcttgcaatg tttgcccatt ttagggacat gagtaggctg aagtttgttc    780
agtgtggact tcagaggcag cacacaaaca gcaagctttg ctctagactg gaattcgtcg    840
acgagctccc tatagtgagt cgtattagag gccgactgac ccggtacccg ggatcttgc     900 taccagtgga acagccacta aggattctgc agtgagagca gagggccagc taagtggtac    960
tctcccagag actgtctgac tcacgccacc ccctccacct tggacacagg acgctgtggt   1020
ttctgagcca ggtacaatga ctcctttcgg taagtgcagt ggaagctgta cactgcccag   1080
gcaaagcgtc cgggcagcgt aggcgggcga ctcagatccc agccagtgga cttagcccct   1140
gtttgctcct ccgataactg gggtgacctt ggttaatatt caccagcagc ctcccccgtt   1200
gcccctctgg atccactgct taaatacgga cgaggacagg gccctgtctc ctcagcttca   1260
ggcaccacca ctgacctggg acagtgaatg tcccccctgat ctgcggccgt gactctctta   1320
aggtagcctt gcagaagttg gtcgtgaggc actgggcagg taagtatcaa ggttacaaga   1380
caggtttaag gagaccaata gaaactgggc ttgtcgagac agagaagact cttgcgtttc   1440
tgataggcac ctattggtct tactgacatc cactttgcct ttctctccac aggtgtccac   1500
tcccagttca attacagctc ttaaggctag agtacttaat acgactcact ataggctagc   1560
ctcgacctcg agacgcgtgc caccatgagc tgccctgtgc ccgcctgttg tgccctgctg   1620
ctggtgctgg gactgtgcag agccagaccc cggaacgctc tgctgctgct ggccgacgat   1680
ggcggatttg agagcggcgc ctacaacaac agcgccattg ccaccccctca tctggacgcc   1740 ctggccagaa gaagcctgct gttccggaac gccttcacca gcgtgtccag ctgcagccct   1800
agcagagctt ccctgctgac aggcctgccc cagcatcaga atggcatgta cggcctgcac   1860
caggatgtgc atcacttcaa cagcttcgac aaagtgcgga gcctgccact gctcctgtca   1920
caggctggcg tgagaaccgg catcatcggc aagaaacacg tgggccccga cagtgtac    1980 cccttcgact cgcctacac cgaagagaac ggcagcgtgc tgcaggtcgg ccggaacatc   2040
acccggatca agctgctcgt gcggaagttt ctccagaccc aggacgaccg gcccttcttc   2100
ctgtacgtgg ccttccacga ccctcacaga tgcggccaca gccagcccca gtacggcacc   2160
ttctgcgaga gttcggcaa cggcgagagc ggcatgggca gaatcccccga ctggaccccc   2220 caggcatacg accctctgga cgtgctggtg ccctacttcg tgcccaacac ccctgccgcc   2280
agagctgatc tggccgccca gtacaccacc gtgggcagaa tggatcaggg cgtgggcctg   2340
gtgctgcagg aactgaggga cgctggcgtg ctgaacgaca ccctggtcat cttcacctcc   2400
gacaacggca tccattccc cagcggccgg accaatctgt actggccgg cacagccgaa   2460 cctctgctgg tgtccagccc cgagcaccct aagagatggg gccaggtgtc cgaggcctac   2520
gtgtccctgc tggacctgac ccccaccatc ctggactggt cagcatccc ctaccccagc   2580 tacgccatct ttggaagcaa gaccatccac ctgaccggca gatctctgct gcctgccctg   2640
gaagctgagc ctctgtgggc caccgtgttc ggcagccaga gccaccacga agtgaccatg   2700
agctacccca tgcggagcgt gcagcaccgg cacttccggg tggtgcacaa cctgaacttc   2760
aagatgccct tcccaatcga ccaggacttt tacgtgtccc ccaccttcca ggacctgctg   2820
aacagaacca cagccggcca gcccaccggc tggtacaagg acctgcggca ctactactac   2880
cgggccagat gggagctgta cgacagaagc cgggaccccc acgagacaca gaacctggcc   2940
```

```
accgacccca gattcgccca gctcctggaa atgctgcggg accagctggc caagtggcag   3000
tgggagacac acgacccttg ggtctgcgct cccgacggcg tgctggaaga gaagctgtcc   3060
ccccagtgcc agccactgca caacgagctg tgaacgcgtg atatcggatc ccggccggcg   3120
gccgcttccc tttagtgagg gttaatgctt cgagcagaca tgataagata cattgatgag   3180
tttggacaaa ccacaactag aatgcagtga aaaaaatgct ttatttgtga aatttgtgat   3240
gctattgctt tatttgtaac cattataagc tgcaataaac aagttaacaa caacaattgc   3300
attcatttta tgtttcaggt tcaggggagag atgtgggagg ttttttaaag caagtaaaac   3360
```

```
gaaaaaggaa gagtatgagt attcaacatt tccgtgtcgc ccttattccc tttttttgcgg    5400 cattttgcct tcctgttttt gctcacccag aaacgctggt gaaagtaaaa gatgctgaag    5460
atcagttggg tgcacgagtg ggttacatcg aactggatct caacagcggt aagatccttg    5520
agagttttcg ccccgaagaa cgttttccaa tgatgagcac ttttaaagtt ctgctatgtg    5580
gcgcggtatt atcccgtatt gacgccggc aagagcaact cggtcgccgc atacactatt    5640
ctcagaatga cttggttgag tactcaccag tcacagaaaa gcatcttacg gatggcatga    5700
cagtaagaga attatgcagt gctgccataa ccatgagtga taacactgcg gccaacttac    5760
ttctgacaac gatcggagga ccgaaggagc taaccgcttt tttgcacaac atgggggatc    5820
atgtaactcg ccttgatcgt tgggaaccgg agctgaatga agccatacca aacgacgagc    5880
gtgacaccac gatgcctgta gcaatggcaa caacgttgcg caaactatta actggcgaac    5940
tacttactct agcttcccgg caacaattaa tagactggat ggaggcggat aaagttgcag    6000
gaccacttct gcgctcggcc cttccggctg gctggtttat tgctgataaa tctggagccg    6060
gtgagcgtgg gtctcgcggt atcattgcag cactggggcc agatggtaag ccctcccgta    6120
tcgtagttat ctacacgacg gggagtcagg caactatgga tgaacgaaat agacagatcg    6180
ctgagatagg tgcctcactg attaagcatt ggtaactgtc agaccaagtt tactcatata    6240
tactttagat tgatttaaaa cttcattttt aatttaaaag gatctaggtg aagatccttt    6300
ttgataatct catgaccaaa atcccttaac gtgagttttc gttccactga gcgtcagacc    6360
ccgtagaaaa gatcaaagga tcttcttgag atcctttttt tctgcgcgta atctgctgct    6420
tgcaaacaaa aaaaccaccg ctaccagcgg tggtttgttt gccggatcaa gagctaccaa    6480
ctcttttccc gaaggtaact ggcttcagca gagcgcagat accaaatact gtccttctag    6540
tgtagccgta gttaggccac cacttcaaga actctgtagc accgcctaca tacctcgctc    6600
tgctaatcct gttaccagtg gctgctgcca gtggcgataa gtcgtgtctt accgggttgg    6660
actcaagacg atagttaccg gataaggcgc agcggtcggg ctgaacgggg ggttcgtgca    6720
cacagcccag cttggagcga acgacctaca ccgaactgag atacctacag cgtgagctat    6780
gagaaagcgc cacgcttccc gaagggagaa aggcggacag gtatccggta agcggcaggg    6840
tcggaacagg agagcgcacg agggagcttc caggggggaaa cgcctggtat ctttatagtc    6900
ctgtcgggtt tcgccacctc tgacttgagc gtcgatttt gtgatgctcg tcaggggggc    6960
ggagcctatg gaaaaacgcc agcaacgcgg cctttttacg gttcctggcc ttttgctggc    7020
cttttgctca catgttcttt cctgcgttat cccctgattc tgtggataac cgtattaccg    7080
cctttgagtg agctgatacc gctcgccgca gccgaacgac cgagcgcagc gagtcagtga    7140
gcgaggaagc ggaagagcgc ccaatacgca aaccgcctct ccccgcgcgt tggccgatt    7199
```